(12) United States Patent
Biagetti et al.

(10) Patent No.: US 9,745,308 B2
(45) Date of Patent: Aug. 29, 2017

(54) PYRIDAZINONE DERIVATIVES AS PHOSHOINOSITIDE 3-KINASES INHIBITORS

(71) Applicant: CHIESI FARMACEUTICI S.p.A., Parma (IT)

(72) Inventors: Matteo Biagetti, Parma (IT); Anna Maria Capelli, Parma (IT); Matilde Guala, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 14 days.

(21) Appl. No.: 14/840,420

(22) Filed: Aug. 31, 2015

(65) Prior Publication Data

US 2016/0075710 A1  Mar. 17, 2016

(30) Foreign Application Priority Data

Sep. 12, 2014 (EP) .................... 14184586

(51) Int. Cl.
| | |
|---|---|
| *C07D 473/34* | (2006.01) |
| *C07D 403/12* | (2006.01) |
| *A61K 31/5377* | (2006.01) |
| *A61K 31/52* | (2006.01) |
| *A61K 31/519* | (2006.01) |
| *A61K 31/506* | (2006.01) |
| *C07D 487/04* | (2006.01) |

(52) U.S. Cl.
CPC .......... *C07D 487/04* (2013.01); *A61K 31/506* (2013.01); *A61K 31/519* (2013.01); *A61K 31/52* (2013.01); *A61K 31/5377* (2013.01); *C07D 403/12* (2013.01); *C07D 473/34* (2013.01)

(58) Field of Classification Search
CPC .... A61K 31/506; A61K 31/519; A61K 31/52; A61K 31/5377; C07D 403/12; C07D 473/34; C07D 487/04
See application file for complete search history.

(56) References Cited

U.S. PATENT DOCUMENTS 4,863,948 A  9/1989 Arrowsmith et al.

FOREIGN PATENT DOCUMENTS

| WO | WO 2005/103039 | 11/2005 |
| WO | WO 2009/080314 | 7/2009 |

OTHER PUBLICATIONS

Neumajer, et al., Novel ion-binding C3 symmetric tripodal triazoles: synthesis and characterization, Central European Journal of Chemistry, 12(1), 115-125 (2014).*
European Search Report in Application No. 14184586.7 issued Nov. 20, 2014.
Timothy D. Cushing et al., Journal of Medicinal Chemistry, vol. 55, No. 20 (2012) pp. 8559-8581.
Omar R'Kyek et al., Heterocycles, vol. 60, No. 11, (2003) pp. 2471-2483.
M.A.F. El-Kaschef et al., Egyptian Journal of Chemistry, vol. 20, No. 1, (1977) pp. 117-123.
Fatima Al-Omran et al.,Tetrahedron, vol. 52, No. 36, (1996) pp. 11915-11928.

* cited by examiner

*Primary Examiner* — Erich A Leeser
(74) *Attorney, Agent, or Firm* — Oblon, McClelland, Maier & Neustadt, L.L.P.

(57) ABSTRACT

Compounds of formula (I) described herein inhibit phosphoinositide 3-kinases (PI3K) and useful for the treatment of disorders associated with PI3K enzymes.

11 Claims, No Drawings

PYRIDAZINONE DERIVATIVES AS PHOSHOINOSITIDE 3-KINASES INHIBITORS

CROSS REFERENCES TO RELATED APPLICATIONS

This application claims priority to European Patent Application No. 14184586.7, filed on Sep. 12, 2014, which is incorporated herein by reference in its entirety.

BACKGROUND OF THE INVENTION

Field of the Invention

The present invention relates to compounds which inhibit phosphoinositide 3-kinases (hereinafter PI3K). In particular, the present invention relates to pyridazinone compounds, methods of preparing such a compound, pharmaceutical compositions which contain such a compound, and therapeutic uses of such a compound.

Discussion of the Background

In biochemistry, a kinase is a type of enzyme that transfers phosphate groups from high-energy donor molecules, such as ATP, to specific substrates, a process referred to as phosphorylation. Specifically, PI3K enzymes are lipid enzyme kinases that can phosphorylate phosphoinositides (PIs) at the 3'-hydroxyl group of the inositol ring (see Panayotou et al, Trends Cell Biol 2:358-60 (1992), which is incorporated herein by reference in its entirety). It is well known that PIs, localized in the plasma membranes, can act as second messengers in signaling cascades by docking proteins containing pleckstrin-homology (PH), FYVE, PX and other phospholipid-binding domains (see Vanhaesebroeck B et al, Annu. Rev. Biochem 70, 535-602, 2001; Katso R et al, Annu. Rev. Cell Dev. Biol. 17, 615-675, 2001, both of which are incorporated herein by reference in their entireties). Therefore, PIs can act as second messengers in many cellular processes including signal transduction, regulation of membrane trafficking and transport, cytoskeleton organization, cell survival and death, and many other functions.

PIs may be bound to the lipid bilayer of the cell membrane via two fatty acids that are attached to the cytosolic inositol ring via a glycerol phosphate linker. PIs inositol ring can be phosphorylated by PI3K enzymes, leading to the regulation of cellular growth, survival and proliferation. For this reason, PIs phosphorylation by PI3K enzymes is one of the most relevant signal transduction events associated with mammalian cell surface receptor activation (see Cantley L C, Science 296, 1655-7, 2002; Vanhaesebroeck B et al, Annu. Rev. Biochem 70, 535-602, 2001, both of which are incorporated herein by reference in their entireties).

The PI3K enzymes have been divided into three classes: Class I PI3K, Class II PI3K and Class III PI3K, on the basis of sequence homology, structure, binding partners, mode of activation, and substrate preference (see Vanhaesebroeck B et al, Exp. Cell Res. 253(1), 239-54, 1999; and Leslie N R et al, Chem. Rev. 101(8), 2365-80, 2001, both of which are incorporated herein by reference in their entireties).

Class I PI3K convert phosphoinositide-(4,5)-diphosphate (PI(4,5)P2) to phosphoinositide-(3,4,5)-triphosphate (PI(3,4,5)P3), which functions as a second messenger. The signaling cascade activated by the increase in intracellular levels of PI(3,4,5)P3 is negatively regulated through the action of 5'-specific and 3'-specific phosphatases (see Vanhaesebroeck B et al., Trends Biochem. Sci. 22(7), 267-72, 1997; Katso R et al, Annu. Rev. Cell Dev. Biol. 17, 615-75, 2001; and Toker A, Cell. Mol. Life Sci. 59(5), 761-79, 2002, all of which are incorporated herein by reference in their entireties).

Class II PI3K enzymes are the most recently identified class of PI3K and their exact function is still unclear. Class III PI3K enzymes consist of a single family member which is structurally related to Class I PI3K enzymes and appears to be important in endocytosis and vesicular trafficking. However, there is some evidence showing that Class III PI3K may be relevant in immune cell processes, such as phagocytosis and Toll-like receptor (TLR) signaling. Class I PI3K enzymes can be further divided in class IA and class IB on the basis of their activation mechanisms.

In more detail, Class IA PI3K enzymes comprise three closely related isoforms: PI3Kα, PI3Kβ and PI3Kδ, while Class IB comprises only the PI3Kγ isoform. These enzymes are heterodimers composed of a catalytic subunit known as p110, with four types: alpha (α), beta (β), delta (δ) and gamma (γ) isoforms, constitutively associated with a regulatory subunit. The first two p110 isoforms (α and β) are ubiquitously expressed and involved in cellular differentiation and proliferation. Consequently, PI3Kα and PI3Kβ enzymes have been extensively studied as targets for the development of new chemotherapeutic agents.

Otherwise, p110δ and p110γ isoforms are mainly expressed in leukocytes and are important in the activation of the immune response, such as leukocytes migration, B and T cells activation and mast cells degranulation. Therefore, PI3Kδ and PI3Kγ isoforms are very relevant in inflammatory respiratory diseases and in cancer.

Presently, the inhibitors of PI3K enzymes known in the art could generally inhibit said isoforms (alpha α, beta β, delta δ and gamma γ isoforms) and they could act on the individual roles played in various diseases by said specific isoforms.

Therefore, specific activity assays of Class IA inhibitors for one specific PI3Kα, PI3Kβ, PI3Kδ and PI3Kγ isoform over another have been extensively developed in order to discern the suitable profile for the treatment of disorders associated with PI3K enzymes mechanisms. Such disorders could, for example, include respiratory diseases selected from idiopathic chronic cough, cough-variant asthma, cough associated with thoracic tumour or lung cancer, viral or post-viral cough, upper airways cough syndrome (UACS) or post nasal drip cough, or cough associated with gastro-oesophageal reflux disease both acid and non-acid, asthma, chronic bronchitis, chronic obstructive pulmonary disease (COPD), interstitial lung disease, idiopathic pulmonary fibrosis (IPF), congestive heart disease, sarcoidosis, infections (such as whooping cough), viral infections including viral respiratory tract infections and viral exacerbation of respiratory diseases; non-viral respiratory infections including aspergillosis and leishmaniasis; allergic diseases including allergic rhinitis and atopic dermatitis; autoimmune diseases including systemic lupus erythematous, rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and central pain.

In view of the number of pathological responses which are mediated by PI3K enzymes, there is a continuing need for inhibitors of PI3K enzymes which can be useful in the treatment of many disorders. Thus, the present invention relates to novel compounds which are inhibitors of PI3Kα, PI3Kβ, PI3Kδ, and PI3Kγ isoforms of Class I PI3K enzymes that, for the above reasons, may often have therapeutically desirable characteristics. Particularly, compounds of the present invention may have much more selectivity for the δ isoform of PI3K enzyme over other isoforms of the same enzyme.

SUMMARY OF THE INVENTION

Accordingly, it is one object of the present invention to provide novel compounds which inhibit phosphoinositide 3-kinases (hereinafter PI3K).

It is another object of the present invention to provide novel pyridazinone compounds which inhibit phosphoinositide 3-kinases (hereinafter PI3K).

It is another object of the present invention to provided novel methods of preparing such a compound.

It is another object of the present invention to provide novel pharmaceutical compositions which contain such a compound.

It is another object of the present invention to provide novel therapeutic uses of such a compound.

These and other objects, which will become apparent during the following detailed description, have been achieved by the inventors' discovery of compounds of formula (I):

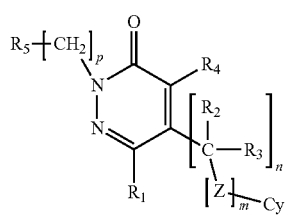

wherein $R_1$, $R_2$, $R_3$, $R_4$, $R_5$, Cy, Z, m, n, and p are as defined below in the detailed description of the invention, which act as inhibitors of phosphoinositide 3-kinases; processes for the preparation of such compounds; and pharmaceutical compositions containing such a compound, either alone or in combination with one or more active ingredients, in admixture with one or more pharmaceutically acceptable carriers.

Thus, in one aspect, the present invention provides the use of a compound of the invention for the manufacture of a medicament.

In a further aspect, the present invention provides the use of a compound of the present invention for the preparation of a medicament for the prevention and/or treatment of any disease characterized by phosphoinositide-3-kinase (PI3K) enzyme over-activity and/or wherein an inhibition of PI3K activity is desirable and in particular through the selective inhibition of the delta or of both the delta and the gamma enzyme isoforms over the alpha and beta ones.

Moreover the present invention provides a method for prevention and/or treatment of any disease wherein a PI3K enzyme inhibition is desirable, said method comprising administering to a patient in need of such treatment a therapeutically effective amount of a compound of the present invention.

In particular the compounds of the present invention, alone or combined with other active ingredients, may be administered for the prevention and/or treatment of a disease of the respiratory tract characterized by inflammatory airway obstruction such as, for example, cough, asthma, COPD and IPF.

PI3K inhibitors are widely known in the art as disclosed, for instance, in "PI3Kδ and PI3Kγ as Targets for Autoimmune and Inflammatory Diseases", Timothy D. Cushing, Daniela P. Metz, Douglas A. Whittington, and Lawrence R. McGee; Journal of Medicinal Chemistry 2012 55 (20), 8559-8581, which is incorporated herein by reference in its entirety. In addition, isocoumarines and indolizines derivatives are disclosed as PI3K inhibitors in European Patent Application Nos. EP 13197986.6 and EP 14172764.4, both of which are incorporated herein by reference in their entireties.

The compounds of the present invention are inhibitors of the activity or function of the Class I of PI3K and more specifically, they are inhibitors of the activity or function of PI3Kα, PI3Kβ, PI3Kδ, and/or PI3Kγ isoforms of the Class I PI3K.

Therefore, the compounds of the present invention may be useful in the treatment of many disorders associated with PI3K enzymes mechanisms, such as respiratory diseases including asthma, chronic obstructive pulmonary disease (COPD), idiopathic pulmonary fibrosis (IPF) and cough; allergic diseases including allergic rhinitis and atopic dermatitis; autoimmune diseases including systemic lupus erythematous, rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; organ transplantation and in particular in transplant rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain, trigeminal neuralgia, and central pain.

DETAILED DESCRIPTION OF THE PREFERRED EMBODIMENTS

The invention is directed to a class of compounds which act as inhibitors of phosphoinositide 3 kinases (PI3K). Said class of compounds inhibits the activity or function of the Class I of PI3K and more specifically, they are inhibitors derivatives of the activity or function of PI3Kα, PI3Kβ, PI3Kγ, and/or PI3Kδ isoforms of the Class I PI3K. The compounds of the present invention have the following formula (I):

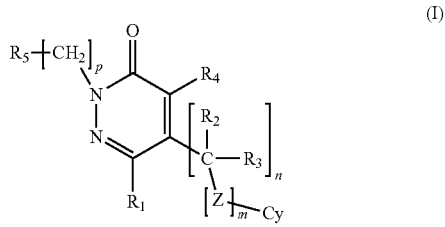

wherein:

$R_1$ and $R_4$ may be the same or different and are each independently selected from the group consisting of: H, halogen, —CN, —$(CH_2)_p NR_6R_7$, $(C_1-C_6)$ alkyl, $(C_1-C_6)$ haloalkyl, $(C_1-C_6)$ hydroxyalkyl, $(C_1-C_6)$ aminoalkyl, $(C_1-C_6)$ alkanoyl, $(C_3-C_7)$ cycloalkyl, $(C_2-C_6)$ alkenyl, $(C_2-C_6)$ alkynyl, aryl, heteroaryl, and heterocycloalkyl, said aryl, heteroaryl, and heterocycloalkyl being optionally and independently substituted by one or more groups selected from halogen, —OH, —$(CH_2)_p NR_6R_7$, —CN, $(C_1-C_6)$ alkyl, $(C_1-C_6)$ haloalkyl, $(C_1-C_6)$ hydroxyalkyl, $(C_2-C_6)$ alkenyl, $(C_2-C_6)$ alkynyl, and $(C_2-C_6)$ hydroxyalkynyl;

$R_2$ and $R_3$ may be the same or different and are selected from the group consisting of: H; $(C_1-C_6)$ alkyl; and $(C_1-C_6)$ haloalkyl;

$R_5$ is selected from the group consisting of: —$NR_6R_7$, $(C_1-C_6)$ alkyl, $(C_1-C_6)$ haloalkyl, $(C_1-C_6)$ hydroxyalkyl, $(C_1-C_6)$ aminoalkyl, $(C_1-C_6)$ alkanoyl, $(C_3-C_7)$ cycloalkyl, (C5-C7) cycloalkenyl, $(C_2-C_6)$ alkenyl, $(C_2-C_6)$ alkynyl, aryl, heteroaryl, and heterocycloalkyl; said aryl, heteroaryl, and heterocycloalkyl being optionally and independently substituted by one or more groups selected from halogen, —OH, —CN, $(C_1-C_6)$ alkyl, $(C_1-C_6)$ haloalkyl, $(C_1-C_6)$ hydroxyalkyl, $(C_2-C_6)$ alkenyl, $(C_2-C_6)$ alkynyl, and $(C_2-C_6)$ hydroxyalkynyl;

Cy is a heteroaryl which can be optionally and independently substituted by one or more groups selected from halogen, —OH, —$(CH_2)_p NR_6R_7$; —CN, —CH=NOH, —$C(O)NR_6R_7$, —$C(O)OR_6$, $(C_1-C_6)$ alkyl, $(C_1-C_6)$ haloalkyl, $(C_1-C_6)$ hydroxyalkyl, $(C_1-C_6)$ alkanoyl, $(C_2-C_6)$ alkenyl, $(C_2-C_6)$ alkynyl, $(C_2-C_6)$ hydroxyalkynyl, aryl, heteroaryl, and heterocycloalkyl, said aryl, heteroaryl, and heterocycloalkyl can be optionally and independently substituted with one or more groups selected from —OH, halogen, —CN, —$S(O)_2NR_6R_7$, —$NR_6S(O)_2R_7$, —$NR_6R_7$, $(C_1-C_6)$ alkyl, $(C_1-C_6)$ haloalkyl, $(C_1-C_6)$ hydroxyalkyl, and $(C_1-C_6)$alkoxy;

$R_6$, $R_7$ may be the same or different at each occurrence, and are each independently selected from the group consisting of —H, $(C_1-C_6)$ alkyl, $(C_1-C_6)$ haloalkyl, $(C_1-C_6)$ hydroxyalkyl, $(C_1-C_6)$ aminoalkyl, $(C_1-C_6)$ alkanoyl, and aryl $(C_1-C_6)$ alkanoyl or, when $R_6$ and $R_7$ are both linked to a nitrogen atom, they may form, together with the nitrogen atom they are linked to, a 4 to 6 membered heterocycle optionally containing one or more additional heteroatom or heteroatomic group selected from O, S, N, NH;

Z, when present, is an atom or a group selected from —O—, —NH—, —C(O)—, —NHC(O)—, —C(O)NH—, —S—, —S(O)—, and —$S(O)_2$—;

m is zero or 1;

n is 1 or 2; and p is zero or an integer ranging from 1 to 3;

or pharmaceutically acceptable salts and or solvates thereof.

DEFINITIONS

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts within the invention may comprise ions of alkali or alkaline earth metals such as potassium, sodium, calcium or magnesium or even ammonium salts.

Those obtained by reacting the compound of formula (I), functioning as a base, with an inorganic or organic acid to form a salt comprise, include, for example, salts of hydrochloric acid, hydrobromic acid, sulfuric acid, phosphoric acid, methane sulfonic acid, toluene sulfonic acid, camphor sulfonic acid, acetic acid, oxalic acid, maleic acid, fumaric acid, succinic acid and citric acid.

Likewise, the compounds of the invention bearing acidic or basic groups can be suitably salified as above reported with amino acids.

In the present description, unless otherwise provided, the term "halogen" or "halogen atom" includes fluorine, chlorine, bromine and iodine, preferably chlorine or fluorine.

The term "$(C_1-C_6)$ alkyl" refers to straight-chained or branched-chained alkyl groups wherein the number of constituent carbon atoms is in the range 1 to 6. Particularly preferred alkyl groups are methyl, ethyl, n-propyl, isopropyl, and t-butyl.

The expression "$(C_1-C_6)$ haloalkyl" refers to the above defined "$(C_1-C_6)$ alkyl" groups wherein one or more hydrogen atoms are replaced by one or more halogen atoms, which can be the same or different from each other.

Examples of said $(C_1-C_6)$ haloalkyl groups may thus include halogenated, poly-halogenated, and fully halogenated alkyl groups wherein, in these latter, all of the hydrogen atoms are replaced by halogen atoms. Preferred examples of $(C_1-C_6)$ haloalkyl groups may be thus represented by trifluoromethyl or difluoro methyl groups.

By way of analogy, the terms "$(C_1-C_6)$ hydroxyalkyl" or "$(C_1-C_6)$ aminoalkyl" refer to the above defined "$(C_1-C_6)$ alkyl" groups wherein one or more hydrogen atoms are replaced by one or more hydroxy or amino groups respectively.

The term "$(C_3-C_7)$ cycloalkyl" refers to saturated cyclic hydrocarbon groups containing from 3 to 7 ring carbon atoms such as, for instance, cyclopropyl, cyclobutyl, cyclopentyl, cyclohexyl, and cycloheptyl.

The term "$(C_2-C_6)$ alkenyl" refers to straight or branched carbon chains with one or more double bonds, conjugated or not conjugated, in cis or trans configuration, wherein the number of carbon atoms is from 2 to 6.

By way of analogy, the term "$(C_5-C_7)$ cycloalkenyl" refers to cyclic hydrocarbon groups containing from 5 to 7 ring carbon atoms and one or two double bonds.

The term "$(C_2-C_6)$ alkynyl" refers to straight or branched carbon chains with one or more triple bonds wherein the number of carbon atoms is from 2 to 6.

Likewise, the expression "$(C_2-C_6)$ hydroxyalkynyl" refers to the above alkynyl moieties wherein one or more hydrogen atoms are replaced by one or more hydroxyl groups.

The expression "aryl" refers to mono, bi-, or tri-cyclic carbon ring systems which have 6 to 20, preferably from 6 to 15 ring atoms, wherein at least one ring is aromatic. The expression "heteroaryl" refers to mono-, bi-, or tri-cyclic ring systems with 5 to 20, preferably 5 to 15 ring atoms, in which at least one ring is aromatic and in which at least one ring atom is a heteroatom or heteroaromatic group (e.g. N, NH, S, or O).

Examples of suitable aryl or heteroaryl monocyclic ring systems include, for instance, phenyl, thienyl, pyrrolyl, pyrazolyl, imidazolyl, isoxazolyl, oxazolyl, isothiazolyl, thiazolyl, pyridinyl, pyrimidinyl, pyrazinyl, triazinyl, furanyl groups, and the like.

Examples of suitable aryl or heteroaryl bicyclic ring systems include naphthalenyl, biphenyl-yl, purinyl, pteridinyl, pyrazolopyrimidinyl, benzotriazolyl, quinolinyl, isoquinolinyl, indolyl, isoindolyl, benzothiophenyl, benzodioxinyl, dihydrobenzodioxinyl, indenyl, dihydro-indenyl, dihydrobenzodioxepinyl, benzooxazinyl groups, and the like.

Examples of suitable aryl or heteroaryl tricyclic ring systems include fluorenyl as well as benzocondensed derivatives of the aforementioned heteroaryl bicyclic ring systems.

The expression "heterocycloalkyl" refers to saturated or partially unsaturated monocyclic cycloalkyl groups in which at least one ring carbon atom is replaced by at least one heteroatom or hetero-group (e.g. N, NH, S, or O). Particularly preferred are "($C_3$-$C_6$) heterocycloalkyl" referring to monocyclic cycloalkyl groups which have 3 to 6 ring atoms in which at least one ring carbon atom is replaced by at least one heteroatom or hetero-group. Examples of ($C_3$-$C_6$) heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydropyranyl, pyranyl, 2H- or 4H-pyranyl, dihydro- or tetrahydrofuranyl, dihydroisoxazolyl groups, and the like.

From all of the above, it is clear to the skilled person that any group or substituent being defined through a composite name has to be intended as construed from the moieties from which it derives. Therefore, just as an example, the term "aryl ($C_1$-$C_6$) alkyl" refers to any ($C_1$-$C_6$) alkyl group as above defined, further substituted by an aryl group or ring as above defined. Suitable examples of the above aryl ($C_1$-$C_6$) alkyl groups may thus include phenylmethyl, better known as benzyl, phenylethyl, or phenylpropyl.

The term "($C_1$-$C_6$) alkanoyl", refers to HC(O)— (i.e. formyl) or to alkylcarbonyl groups (e.g. ($C_1$-$C_6$) alkylC(O)— wherein the group "alkyl" has the meanings above reported). Examples of ($C_1$-$C_6$) alkanoyl may thus include formyl, acetyl, propanoyl, butanoyl, isobutyryl, and the like.

The term "($C_1$-$C_6$)alkoxy" refers to a straight or branched hydrocarbon of from 1 to 6 carbon atoms, attached to the rest of the molecule through an oxygen bridge (e.g. alkyloxy groups). Suitable examples of ($C_1$-$C_6$)alkoxy groups may thus include methoxy, ethoxy, n-propoxy, isopropoxy, n-butoxy, and the like.

The term "aryl ($C_1$-$C_6$) alkanoyl" refers to the above ($C_1$-$C_6$) alkanoyl groups wherein the alkyl moiety is further substituted by an aryl group, wherein aryl and alkyl have the meaning above defined. Examples are represented by benzoyl, phenylacetyl, phenylpropanoyl, and phenylbutanoyl groups.

As used herein, the expression "ring system" refers to monocyclic, bicyclic, or tricyclic ring systems which may be saturated, partially unsaturated or unsaturated, such as aryl, ($C_3$-$C_7$) cycloalkyl, ($C_3$-$C_6$) heterocycloalkyl, or heteroaryl.

The terms "group", "radical" or "fragment" or "substituent" are synonymous and are intended to indicate functional groups or fragments of molecules attachable to a bond or other fragments or molecules. A dash ("-") that is not between two letters or symbols is meant to represent the point of attachment for a substituent. When graphically represented the point of attachment in a cyclic functional group (e.g. formulae I-1 to I-9) is indicated with a dot ("•") localized in one of the available ring atoms where the functional group is attachable to a bond or other fragment of molecules.

An oxo moiety is represented by (O) as an alternative to the other common representation, e.g. (=O). Thus, in terms of general formula, the carbonyl group is herein preferably represented as —C(O)— as an alternative to the other common representations such as —CO—, —(CO)— or —C(=O)—. In general, the group in parentheses is a lateral group, not included into the chain, and parentheses are used, when deemed useful, to help clarify linear chemical formulas; e.g. the sulfonyl group —$SO_2$— might be also represented as —$S(O)_2$— to distinguish e.g. with respect to the sulfinic group —S(O)O—.

It will be apparent to those skilled in the art that compounds of formula (I) may contain one or more stereogenic centers, for instance as represented in formula (IA) by the carbon atom (*) with an asterisk, wherein $R_2$ and $R_3$ have different meanings, and therefore may exist as optical stereoisomers.

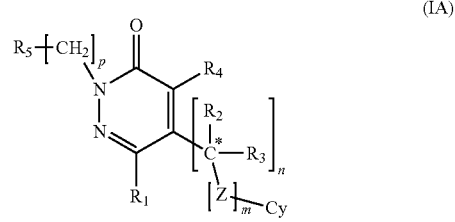

(IA)

Where the compounds according to the invention have at least one stereogenic center, they may accordingly exist as enantiomers. Where the compounds according to the invention possess two or more stereogenic centers, they may additionally exist as diastereoisomers. It is to be understood that all such single enantiomers, diastereoisomers and mixtures thereof in any proportion are encompassed within the scope of the present invention. The absolute configuration (R) or (S) for carbon (*) is assigned on the basis of Cahn-Ingold-Prelog nomenclature rules based on groups' priorities.

Atropisomers are stereoisomers resulting from hindered rotation about single bonds where the steric strain barrier to rotation is high enough to allow for the isolation of the conformers (see Bringmann G et al, *Angew. Chemie Int. Ed.*, 44 (34), 5384-5427, 2005, which is incorporated herein by reference in its entirety).

Oki defined atropisomers as conformers that interconvert with a half-life of more than 1000 seconds at a given temperature (see Oki M, Topics in Stereochemistry 14, 1-82, 1983, which is incorporated herein by reference in its entirety).

Atropisomers differ from other chiral compounds in that in many cases they can be equilibrated thermally whereas in the other forms of chirality isomerization is usually only possible chemically.

Separation of atropisomers is possible by chiral resolution methods such as selective crystallization. In an atropo-enantioselective or atroposelective synthesis one atropisomer is formed at the expense of the other. Atroposelective synthesis may be carried out by use of chiral auxiliaries like a Corey Bakshi Shibata (CBS) catalyst, an asymmetric catalyst derived from proline, or by approaches based on thermodynamic equilibration when an isomerization reaction favors one atropisomer over the other.

Racemic forms of compounds of formula (I) as well as the individual atropisomers if present (substantially free of its corresponding enantiomer) and stereoisomer-enriched atropisomers mixtures are included in the scope of the invention.

In a preferred embodiment, the invention is directed to compounds of formula (I) as above defined wherein n=1, $R_2$ has the same meaning as above except H, $R_3$ is H, and the absolute configuration of the chiral carbon (*) is (R).

In another embodiment the preferred configuration of the carbon (*) is (S).

In a preferred embodiment, the compounds of formula (I) are present as mixtures of enantiomers or diastereoisomers.

It is to be understood that all preferred groups or embodiments described herein below for compounds of formula (I) may be combined among each other and apply as well mutatis mutandis.

A first preferred group of compounds is that of formula (I) wherein:
$R_2$ is selected from H and $(C_1-C_6)$ alkyl;
$R_3$ is H;
$R_1$, $R_4$, $R_5$, m, n, p, Z, and CY are as defined above or pharmaceutically acceptable salts and or solvates thereof.

A more preferred group of compounds is that of formula (I) wherein:
$R_2$ is selected from H and $(C_1-C_6)$ alkyl;
$R_3$ is H;
Cy is a heteroaryl selected from the group consisting of I-1 to I-9 wherein (I-1) is 3H-purin-3-yl, (I-2) is 9H-purin-9-yl, (I-3) is 9H-purin-6-yl, (I-4) is 1H-pyrazolo[3,4-d]pyrimidin-1-yl, (I-5) is 6-oxo-5H-,6H,7H-pyrrolo[2,3-d]pyrimidin4-yl, (I-6) is pyrimidin-4-yl, (I-7) is pyrimidin-2-yl, (I-8) is pyrazin-2-yl, and (I-9) is 1,3,5-triazin-2-yl; which can be optionally and independently substituted by one or more groups selected from halogen, —OH, —$(CH_2)_p$NR$_6$R$_7$; —CN, —CH=NOH, —C(O)NR$_6$R$_7$, —C(O)OR$_6$, $(C_1-C_6)$ alkyl, $(C_1-C_6)$ haloalkyl, $(C_1-C_6)$ hydroxyalkyl, $(C_1-C_6)$ alkanoyl, $(C_2-C_6)$ alkenyl, $(C_2-C_6)$ alkynyl, and $(C_2-C_6)$ hydroxyalkynyl, or by a group selected from aryl, heteroaryl, and heterocycloalkyl which can be optionally and independently substituted with one or more groups selected from —OH, halogen, —CN, —S(O)$_2$NR$_6$R$_7$, —NR$_6$S(O)$_2$R$_7$, —NR$_6$R$_7$, $(C_1-C_6)$ alkyl, $(C_1-C_6)$ haloalkyl, $(C_1-C_6)$ hydroxyalkyl, $(C_1-C_6)$alkoxy; wherein all the other variables are as defined above;
or pharmaceutically acceptable salts and or solvates thereof.

A first class of preferred compounds of formula (I) for use as a medicament is that wherein Cy is 1H-pyrazolo[3,4-d]pyrimidin-1-yl, optionally and independently substituted by one or more groups selected from halogen, —OH, —$(CH_2)_p$NR$_6$R$_7$; —CN, —CH=NOH, —C(O)NR$_6$R$_7$, —C(O)OR$_6$, $(C_1-C_6)$ alkyl, $(C_1-C_6)$ haloalkyl, $(C_1-C_6)$ hydroxyalkyl, $(C_1-C_6)$ alkanoyl, $(C_2-C_6)$ alkenyl, $(C_2-C_6)$ alkynyl, and $(C_2-C_6)$ hydroxyalkynyl, or by a group selected from aryl, heteroaryl, and heterocycloalkyl, which can be optionally and independently substituted with one or more groups selected from —OH, halogen, —CN, —S(O)$_2$NR$_6$R$_7$, —NR$_6$S(O)$_2$R$_7$, —NR$_6$R$_7$, $(C_1-C_6)$ alkyl, $(C_1-C_6)$ haloalkyl, $(C_1-C_6)$ hydroxyalkyl, $(C_1-C_6)$alkoxy;
wherein m is zero and all the other variables are as defined above;
or pharmaceutically acceptable salts and or solvates thereof.

A further preferred embodiment in this first class is represented by compounds of formula I wherein:
$R_1$ and $R_4$ may be the same or different and are independently selected from the group consisting of: H, $(C_3-C_7)$ cycloalkyl, which is cyclopentyl, and aryl, which is phenyl;
$R_2$ is selected from H and $(C_1-C_6)$ alkyl, which is methyl;
$R_3$ is H;
$R_5$ is selected from the group consisting of $(C_1-C_6)$ alkyl, which is methyl, isopropyl or tert-butyl, $(C_3-C_7)$ cycloalkyl, which is cyclopropyl, aryl, which is phenyl, heteroaryl, which is pyridinyl, and heterocycloalkyl, which is morpholinyl;

Cy is a heteroaryl which is 1H-pyrazolo[3,4-d]pyrimidin-1-yl, optionally and independently substituted by one or more groups selected from halogen, which is iodine, —$(CH_2)_p$NR$_6$R$_7$, which is —NH$_2$, aryl, which is phenyl, heteroaryl, which is pyridinyl, said aryl and heteroaryl can be optionally and independently substituted with one or more groups selected from —OH and halogen which is fluorine;
wherein $R_6$ and $R_7$ are —H
m is zero;
n is 1;
p is in each occurrence independently 0 or 1 or 2;
or pharmaceutically acceptable salts and or solvates thereof.

Another class of preferred compounds of formula (I) for use as a medicament is that wherein Cy is (I-6) is pyrimidin-4-yl, optionally substituted by one or more groups selected from halogen, —OH, —$(CH_2)_p$NR$_6$R$_7$; —CN, —CH=NOH, —C(O)NR$_6$R$_7$, —C(O)OR$_6$, $(C_1-C_6)$ alkyl, $(C_1-C_6)$ haloalkyl, $(C_1-C_6)$ hydroxyalkyl, $(C_1-C_6)$ alkanoyl, $(C_2-C_6)$ alkenyl, $(C_2-C_6)$ alkynyl, and $(C_2-C_6)$ hydroxyalkynyl, or by a group selected from aryl, heteroaryl and heterocycloalkyl which can be optionally and independently substituted with one or more groups selected from —OH, halogen, —CN, —S(O)$_2$NR$_6$R$_7$, —NR$_6$S(O)$_2$R$_7$, —NR$_6$R$_7$, $(C_1-C_6)$ alkyl, $(C_1-C_6)$ haloalkyl, $(C_1-C_6)$ hydroxyalkyl, and $(C_1-C_6)$alkoxy;
m is 1 and all the other variables are as defined above;
or pharmaceutically acceptable salts and or solvates thereof.

A further preferred embodiment in this class is represented by compounds of formula I wherein:
$R_1$ is aryl, which is phenyl, and $R_4$ is H;
$R_2$ is $(C_1-C_6)$ alkyl, which is methyl;
$R_3$ is H;
$R_5$ is selected from the group consisting of $(C_1-C_6)$ alkyl, which is methyl or isopropyl, $(C_3-C_7)$ cycloalkyl, which is cyclopropyl, and aryl, which is phenyl;
Cy is (I-6) is pyrimidin-4-yl substituted by —$(CH_2)_p$NR$_6$R$_7$ which is —NH$_2$, and —CN;
m is 1;
$R_6$, $R_7$ are —H;
Z is —NH—;
n is 1;
p is at each occurrence independently zero or 1;
or pharmaceutically acceptable salts and or solvates thereof.

I-1 to I-9 can be graphically represented as follows:

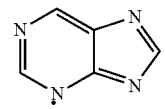
I-1

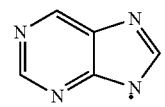
I-2

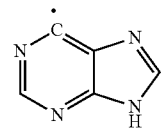
I-3

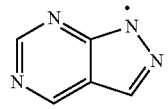
I-4

-continued

I-5
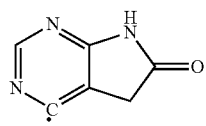

I-6
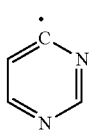

I-7
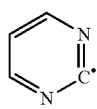

I-8
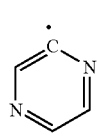

I-9
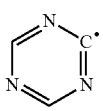

As explained above when graphically represented the monoradical symbol "•" is localized in one of the available ring atoms indicating where the functional group is attachable to a bond or other fragment of molecules. This is not limiting the scope solely to the graphically represented structures; the invention includes also other chemically acceptable localization of the point of attachment in the functional group.

Examples of preferred aryl, heteroaryl, heterocycloalkyl groups are phenyl, pyridinyl, thiazolyl and tetrazolyl groups, 3-fluoro-5-hydroxyphenyl, 2-amino-1,3-thiazol-5-yl, 5-hydroxypyridin-3yl, 1-methyl-1,2,3,6-tetrahydropyridin-4-yl; corresponding to the below reported structures (CHEMAXON 6.0.4 name to structure tool) are particularly preferred.

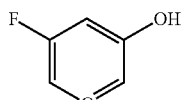
3-fluoro-5-hydroxyphenyl

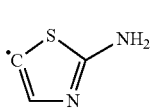
2-amino-1,3-thiazol-5-yl

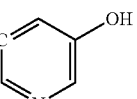
5-hydroxypyridin-3yl

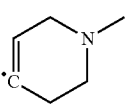
1-methyl-1,2,3,6-tetrahydropyridin-4yl

According to specific embodiments, the present invention provides the compounds listed in the table below and pharmaceutical acceptable salts thereof.

| Example | Chemical name |
|---|---|
| Example 1 | 5-{-[4-amino-3-(3-fluoro-5-hydroxyphenyl)-1H-pyrazolo[3,4-d]pyrimidin-1-yl]ethyl}-2-benzyl-6-phenyl-2,3-dihydropyridazin-3-one |
| Example 2 | 5-{1-[4-amino-3-(3-fluoro-5-hydroxyphenyl)-1H-pyrazolo[3,4-d]pyrimidin-1-yl]ethyl}-2-methyl-6-phenyl-2,3-dihydropyridazin-3-one |
| Example 3 | 5-{1-[4-amino-3-(3-fluoro-5-hydroxyphenyl)-1H-pyrazolo[3,4-d]pyrimidin-1-yl]ethyl}-6-phenyl-2-(propan-2-yl)-2,3-dihydropyridazin-3-one |
| Example 4 | 5-{1-[4-amino-3-(3-fluoro-5-hydroxyphenyl)-1H-pyrazolo[3,4-d]pyrimidin-1-yl]ethyl}-2-(cyclopropylmethyl)-6-phenyl-2,3-dihydropyridazin-3-one |
| Example 5 | 5-{1-[4-amino-3-(3-fluoro-5-hydroxyphenyl)-1H-pyrazolo[3,4-d]pyrimidin-1-yl]ethyl}-2,6-diphenyl-2,3-dihydropyridazin-3-one |
| Example 6 | 5-{1-[4-amino-3-(3-fluoro-5-hydroxyphenyl)-1H-pyrazolo[3,4-d]pyrimidin-1-yl]ethyl}-6-phenyl-2-(pyridin-2-ylmethyl)-2,3-dihydropyridazin-3-one |
| Example 7 | 5-{1-[4-amino-3-(3-fluoro-5-hydroxyphenyl)-1H-pyrazolo[3,4-d]pyrimidin-1-yl]ethyl}-2-benzyl-2,3-dihydropyridazin-3-one |
| Example 8 | 5-{1-[4-amino-3-(3-fluoro-5-hydroxyphenyl)-1H-pyrazolo[3,4-d]pyrimidin-1-yl]ethyl}-2-phenyl-2,3-dihydropyridazin-3-one |
| Example 9 | 5-{1-[4-amino-3-(3-fluoro-5-hydroxyphenyl)-1H-pyrazolo[3,4-d]pyrimidin-1-yl]ethyl}-2-methyl-2,3-dihydropyridazin-3-one |
| Example 10 | 5-{1-[4-amino-3-(3-fluoro-5-hydroxyphenyl)-1H-pyrazolo[3,4-d]pyrimidin-1-yl]ethyl}-2-tert-butyl-4-phenyl-2,3-dihydropyridazin-3-one |
| Example 11 | 5-{1-[4-amino-3-(3-fluoro-5-hydroxyphenyl)-1H-pyrazolo[3,4-d]pyrimidin-1-yl]ethyl}-2-benzyl-4-phenyl-2,3-dihydropyridazin-3-one |
| Example 12 | 5-{1-[4-amino-3-(3-fluoro-5-hydroxyphenyl)-1H-pyrazolo[3,4-d]pyrimidin-1-yl]ethyl}-2-methyl-4-phenyl-2,3-dihydropyridazin-3-one |
| Example 13 | 5-{1-[4-amino-3-(3-fluoro-5-hydroxyphenyl)-1H-pyrazolo[3,4-d]pyrimidin-1-yl]ethyl}-2,4-diphenyl-2,3-dihydropyridazin-3-one |
| Example 14 | 5-{1-[4-amino-3-(3-fluoro-5-hydroxyphenyl)-1H-pyrazolo[3,4-d]pyrimidin-1-yl]ethyl}-2-[2-(morpholin-4-yl)ethyl]-4-phenyl-2,3-dihydropyridazin-3-one |
| Example 15 | 5-{1-[4-amino-3-(3-fluoro-5-hydroxyphenyl)-1H-pyrazolo[3,4-d]pyrimidin-1-yl]ethyl}-4-phenyl-2-(pyridin-3-yl)-2,3-dihydropyridazin-3-one |
| Example 16 | 5-{1-[4-amino-3-(3-fluoro-5-hydroxyphenyl)-1H-pyrazolo[3,4-d]pyrimidin-1-yl]ethyl}-2-benzyl-4-cyclopentyl-2,3-dihydropyridazin-3-one |
| Example 17 | 5-{1-[4-amino-3-(5-hydroxypyridin-3-yl)-1H-pyrazolo[3,4-d]pyrimidin-1-yl]ethyl}-2-benzyl-4-cyclopentyl-2,3-dihydropyridazin-3-one |
| Example 18 | 5-{[4-amino-3-(3-fluoro-5-hydroxyphenyl)-1H-pyrazolo[3,4-d]pyrimidin-1-yl]methyl}-2-benzyl-2,3-dihydropyridazin-3-one |
| Example 19 | 4-amino-6-{[1-(1-benzyl-6-oxo-3-phenyl-1,6-dihydropyridazin-4-yl)ethyl]amino}pyrimidine-5-carbonitrile |
| Example 20 | 4-amino-6-(1-(1-methyl-6-oxo-3-phenyl-1,6-dihydropyridazin-4-yl)ethylamino)pyrimidine-5-carbonitrile |
| Example 21 | 4-amino-6-({1-[6-oxo-3-phenyl-1-(propan-2-yl)-1,6-dihydropyridazin-4-yl]ethyl}amino)pyrimidine-5-carbonitrile |
| Example 22 | 4-amino-6-({1-[1-(cyclopropylmethyl)-6-oxo-3-phenyl-1,6-dihydropyridazin-4-yl]ethyl}amino)pyrimidine-5-carbonitrile |
| Example 23 | 4-amino-6-{[1-(6-oxo-1,3-diphenyl-1,6-dihydropyridazin-4-yl)ethyl]amino}pyrimidine-5-carbonitrile |
| Example 24 | 2-benzyl-6-phenyl-5-{1-[(9H-purin-6-yl)amino]ethyl}-2,3-dihydropyridazin-3-one |

The compounds of formula (I) including all the compounds here above listed can be generally prepared according to the procedure outlined in the following Schemes shown below using generally known methods.

Preparation of Examples

Experimental Procedure 1

According to the Reaction scheme 1, the compounds of Formula (Ia) can be prepared by reacting intermediate of Formula (II) and a suitable halide Cy-Hal (III), where all variables have the meaning above defined, and Cy-Hal is for example 6-bromopurine, 4-amino-6-chloropyrimidine-5-carbonitrile. Typically, the reaction is performed in a suitable polar solvent, such as t-BuOH, in the presence of a base, such as DIPEA, at an appropriate temperature ranging for example from 80° C. to 100° C. This scheme provides a synthetic route for the preparation of the compounds of Examples 19, 20, 21, 22, 23, and 24.

Reaction Scheme 1

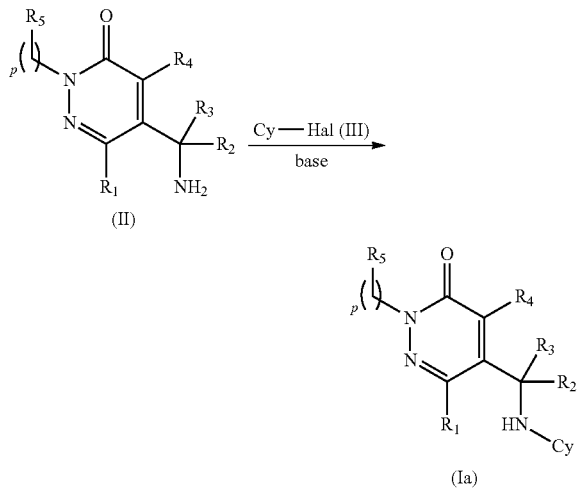

Experimental Procedure 2

According to the Reaction scheme 2, the compounds of Formula (IV) can be converted into compounds of Formula (V) by reaction with a nitrogen-based nucleophile of Formula (VI), under Mitsunobu reaction conditions. Compounds of Formula (V) were then converted into compounds of formula (Ib), where all variable has the meaning above defined, by Suzuki cross-coupling reaction with a suitable boronic acid or ester of Formula (VII). Wherein Het(Aryl) stands for any substituent group like aryl, heteroaryl.

Reaction Scheme 2

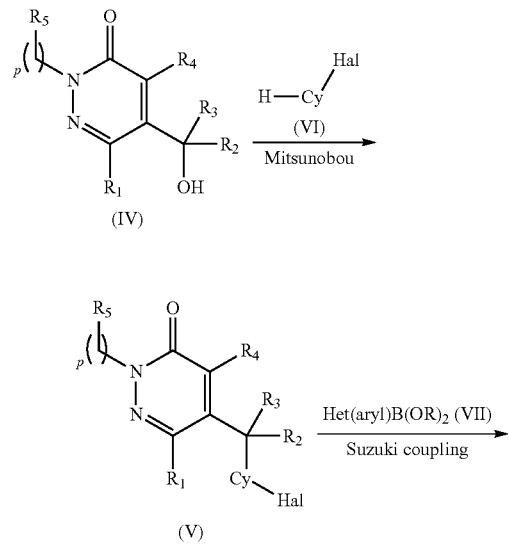

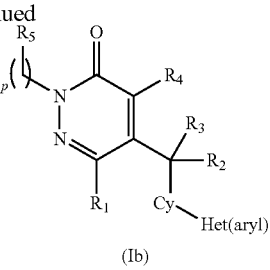

Typical Mitsunobu coupling is performed by reaction of a compound of formula (IV) with nitrogen-based nucleophile (VI), such as for example 3-iodo-1H-pyrazolo[3,4-d]pyrimidin-4-amine in a polar aprotic solvent, such as THF, in the presence of a dialkyl azodicarboxylate, such as DIAD and a triaryl phosphine, such as triphenylphosphine, at an appropriate temperature, such as, for example, at r.t. (room temperature). Typical Suzuki cross-coupling conditions comprise reacting a compound of formula (V) with a suitable boronic acid or boronic ester (VII), in the presence of a Pd catalyst, such as $Pd(PPh_3)_4$, using a base, such as aqueous sodium bicarbonate, in a mixture of polar solvents, such as DME and EtOH, at an appropriate temperature, ranging from r.t. to 80° C. Boronic acid and esters of formula (VII) are commercially available. This scheme provides a synthetic route for the preparation of the compound of Examples 1, 2, 3, 4, 5, 6, 7, 8, 9, 10, 11, 12, 13, 14, 15, 16, 17, and 18.

Preparation of Intermediates

Experimental Procedure 3

According to the Reaction scheme 3, intermediates of Formula (IV) can be converted into intermediates of formula (II) by preparation of azide (VIII) followed by reduction under Staudinger conditions.

Reaction Scheme 3

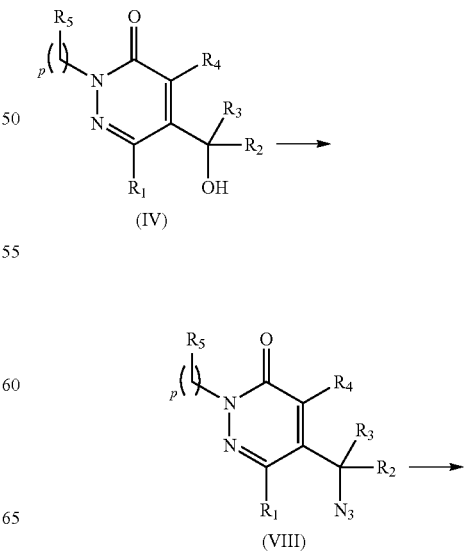

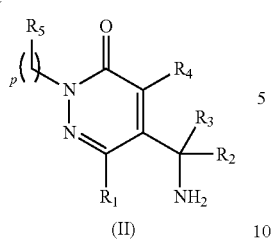

(II)

Typical reaction conditions comprise reacting a compound of formula (IV) with diphenylphosphorylazide in the presence of a base, such as DBU, in a polar aprotic solvent, such as THF, at an appropriate temperature, such as r.t. Typical Staudinger reduction conditions comprise reacting a compound of formula (VIII) with a triaryl phosphine, such as triphenylphosphine, in a suitable polar aprotic solvent, such as THF, at an appropriate temperature, such as, for example r.t., followed by water and stirring at an appropriate temperature, such as, for example, ranging from 50° C. to 60° C.

Experimental Procedure 4

According to the Reaction scheme 4, intermediate of Formula (IVa), wherein $R_2$=Me, $R_3$, $R_4$=H and $R_1$=Ph, can be prepared from commercially available intermediate (IXa), wherein $R_4$=H and $R_1$=Ph and Hal is bromide.

Reaction Scheme 4

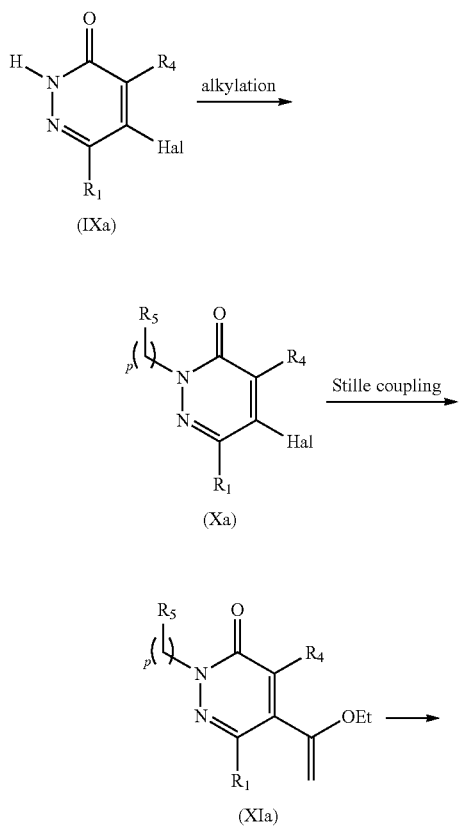

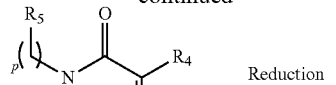

(XIIa)

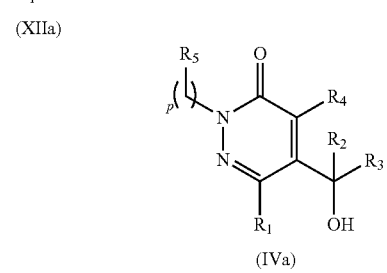

(IVa)

Intermediate of Formula (IXa) can be converted into intermediate of Formula (Xa) by alkylation with an alkyl halide in the presence of a base, or with dimethylformamide dimethyl acetal. Typical alkylation conditions comprise reacting a compound of formula (IXa) with a suitable alkyl halide (i.e. $R_5(CH_2)_p$-Hal) in the presence of a base, such as potassium carbonate, or with dimethylformamide dimethyl acetal, in a polar aprotic solvent, such as in DMF, at an appropriate temperature, for example at ranging from RT to 60° C. Intermediate of Formula (Xa) can be converted into intermediate of Formula (XIa) by means of Palladium catalysed cross-coupling reaction under Stille conditions with tributyl(1-ethoxyvinyl)tin. Typical reaction conditions comprise reacting a compound of formula (Xa) with tributyl (1-ethoxyvinyl)tin, in the presence of a Pd catalyst, such as bis(triphenylphosphine)palladium(II) dichloride, in a polar aprotic solvent, such as in toluene, at an appropriate temperature, such as for example at 110° C. Intermediate (XIa) was then deprotected into intermediate of Formula (XIIa) by treatment with conc. HCl, in a polar aprotic solvent, such as in toluene, at an appropriate temperature, for example at r.t. (for deprotection conditions see the general protocols reported in *Greene's Protective Groups in Organic Synthesis*, Peter G. M. Wuts, Theodora W. Greene; Wiley&Sons Editors, 4th Edition December 2006, which is incorporated herein by reference in its entirety). This deprotection step was used for the preparation of Examples 45, 46, and 103). Finally, an intermediate of formula (XIa) can be converted into alcohol (IVa). Typical reduction conditions comprise reacting a compound of formula (XIIa) with a reducing reagent, such as $NaBH_4$, in a mixture of polar aprotic and protic solvents, such as THF and MeOH, at an appropriate temperature, for example at r.t. The crude obtained from reduction of a compound of formula (XIIa) was partially oxidized with a suitable oxidant such as $CuCl_2$ in a polar aprotic solvent, such as $CH_3CN$, at an appropriate temperature, such as at 85° C., or sodium 3-nitrobenzenesulfonate in aqueous NaOH, at an appropriate temperature, such as heating to reflux.

Experimental Procedure 5

According to the Reaction scheme 5, intermediate of Formula (XIIa), wherein $R_2$=Me, $R_4$=H and $R_1$=Ph, can be alternatively prepared from commercially available intermediate (IXa), wherein $R_4$=H and $R_1$=Ph and Hal is bromide.

Reaction Scheme 5

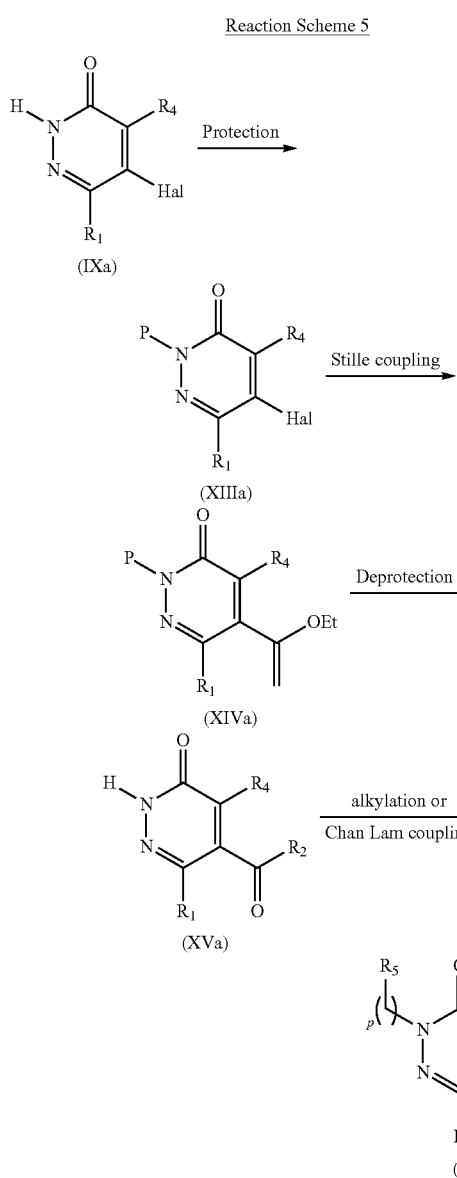

reflux. Intermediate of Formula (XVa) was finally converted into intermediate of Formula (XIIa) with an alkylation reaction with an alkyl halide, or in a Chan Lam reaction with a suitable boronic acid or ester (VII). Typical alkylation conditions comprise reacting a compound of formula (XVa) with a suitable alkyl halide in the presence of a base, such as potassium carbonate, in a polar aprotic solvent, such as in DMF, at an appropriate temperature, for example at r.t. Typical Chan Lam reaction conditions comprise reacting a compound of formula (XVa) with a suitable boronic acid (VII), such as phenylboronic acid, in the presence of copper (II) acetate and pyridine, in a mixture of polar aprotic solvents, such as DCM and DMF, at an appropriate temperature, for example at r.t., in the open air.

Experimental Procedure 6

According to the Reaction scheme 6, intermediate of Formula (IVb), wherein $R_2$=Me, $R_1$, $R_3$=H, can be prepared from commercially available intermediate (XVI), wherein $R_1$=H.

Reaction Scheme 6

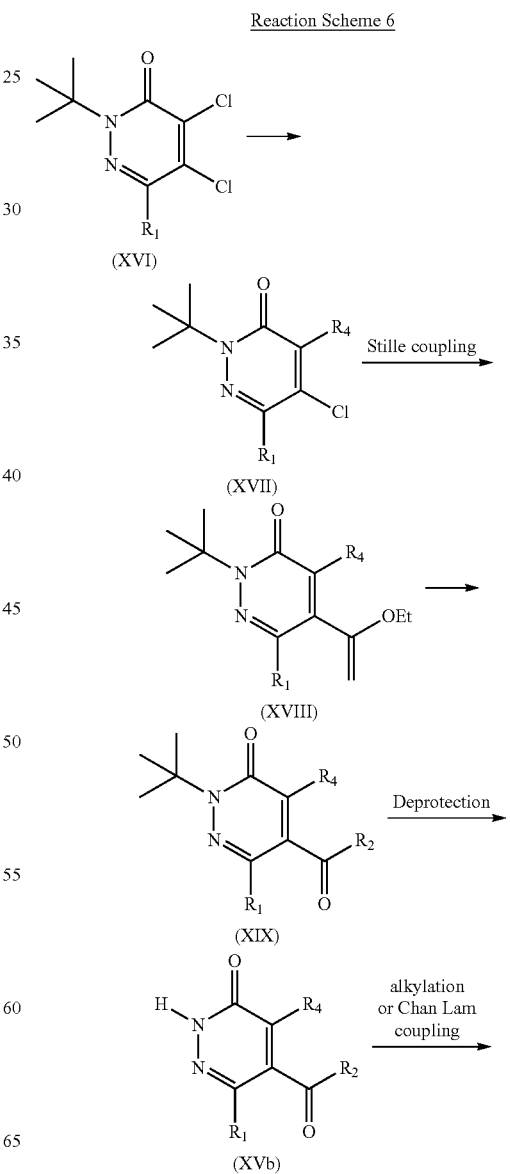

Intermediate of Formula (IXa) is protected by means of a suitable protecting group, such as for example THP. Typical reaction conditions comprise reacting a compound of formula (IXa) with 3,4-dihydro-2H-pyran, in the presence of an acid, such as pyridinium p-toluenesulfonate, in a suitable solvent, such as THF, at an appropriate temperature, for example, ranging from 60° C. to 90° C. Intermediate of Formula (XIIIa) may be converted into intermediate of Formula (XIVa) by means of Palladium catalyzed cross-coupling reaction under Stille conditions with tributyl(1-ethoxyvinyl)tin. Typical reaction conditions comprise reacting a compound of Formula (XIVa) with tributyl(1-ethoxyvinyl)tin, in the presence of a Pd catalyst, such as bis(triphenylphosphine)-palladium(II) dichloride, in a polar aprotic solvent, such as in toluene, at an appropriate temperature, such as for example at 110° C. Intermediate (XIVa) was then deprotected into intermediate of Formula (XVa) by treatment with HCl. Typical reaction conditions comprise reacting a compound of Formula (XVa) with aqueous 6N HCl at an appropriate temperature, for example heating to

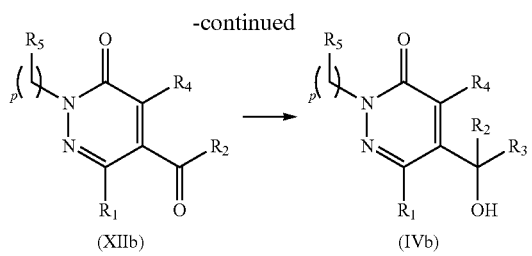

(XIIb) → (IVb)

An intermediate of Formula (XVI) can be converted into compound of Formula (XVII) by reaction with a suitable Grignard reagent. Typical reaction conditions comprise reacting a compound of Formula (XVI) with a suitable arylmagnesium halide or alkylmagnesium halide, such as phenylmagnesium bromide or cyclopentylmagnesium chloride, in a polar aprotic solvent, such as in THF, at an appropriate temperature, for example at 0° C. A compound of formula (XVI) wherein $R_1$=H could be prepared accordingly to the procedure reported in US2005/0191238 A1, which is incorporated herein by reference in its entirety. A compound of Formula (XVII) is then reacted with tributyl (1-ethoxyvinyl)tin under Stille cross-coupling conditions to give intermediate of formula (XVIII). Typical reaction conditions comprise reacting a compound of formula (XVII) with tributyl(1-ethoxyvinyl)tin, in the presence of a Pd catalyst, such as bis(triphenylphosphine)palladium(II) dichloride, in a polar aprotic solvent, such as in toluene, at an appropriate temperature, for example at 110° C. A compound of Formula (XVIII) can be hydrolyzed to give intermediate ketone of Formula (XIX) with HCl. Typical reaction conditions comprise reacting a compound of formula (XVIII) with conc. HCl, in a polar aprotic solvent, such as in toluene, at an appropriate temperature, for example at r.t. Intermediate ketones of Formula (XIX) were then converted into intermediate of Formula (XVb), wherein $R_2$=Me, $R_1$=H, with TFA. Typical reaction conditions comprise reaction of a compound of Formula (XIX) with TFA, at an appropriate temperature, for example at 120° C. under microwave (MW) irradiation. Intermediate of Formula (XVb), wherein $R_2$=Me, $R_1$=H, can then be used in an alkylation reaction with an alkyl halide, or in a Chan Lam reaction with a suitable boronic acid or ester (VII) to give intermediate (XIIb), wherein $R_2$=Me, $R_1$=H. Typical alkylation conditions comprise reacting a compound of formula (XVb) with a suitable alkyl halide in the presence of a base, such as potassium carbonate, in a polar aprotic solvent, such as in DMF, at an appropriate temperature, for example at ranging from r.t. to 50° C. Typical Chan Lam reaction conditions comprise reacting a compound of formula (XVb) with a suitable boronic acid, in the presence of copper (II) acetate and pyridine, in a mixture of polar aprotic solvents, such as DCM and DMF, at an appropriate temperature, for example at r.t., in the open air. Finally an intermediate of Formula (XIIb) may be reduced to give intermediate (IVb), wherein $R_2$=Me, $R_1$, $R_3$=H. Typical reaction conditions comprise a reaction of a compound of formula (XIIb) with a reducing reagent, such as NaBH$_4$, in a mixture of polar aprotic and protic solvents, such as THF and MeOH, at an appropriate temperature, for example ranging from 0° C. to r.t.

Experimental Procedure 7

According to the Reaction scheme 7, intermediate of Formula (XIIb), wherein $R_2$=Me, $R_1$=H, can be alternatively prepared from intermediate (XVII).

Reaction Scheme 7

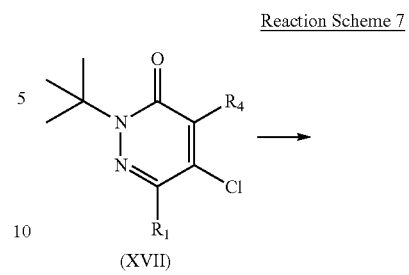

An intermediate of Formula (XX) can be prepared by deprotection of a compound of Formula (XVII) in sulphuric acid and nitric acid. Typical reaction conditions comprise reacting a compound of Formula (XVII) with conc. $H_2SO_4$ and conc. $HNO_3$, at an appropriate temperature, for example at r.t. Intermediate (XX) can be converted into intermediate of Formula (XXI) with an alkyl halide in the presence of a base. Typical alkylation conditions comprise reacting a compound of Formula (XX) with a suitable alkyl halide, such as benzylbromide, in the presence of a base, such as potassium carbonate, in a polar aprotic solvent, such as in DMF, at an appropriate temperature, for example at r.t. This intermediate of Formula (XXI) was then reacted with tributyl(1-ethoxyvinyl)tin under Stille cross-coupling conditions. Typical reaction conditions comprise reacting a compound of Formula (XXI) with tributyl(1-ethoxyvinyl)tin, in the presence of a Pd catalyst, such as bis(triphenylphosphine) palladium(II) dichloride, in a polar aprotic solvent, such as in toluene, at an appropriate temperature, for example at 110° C. Intermediate of Formula (XIb) was hydrolyzed to ketone of Formula (XIIb) with HCl. Typical reaction conditions comprise reacting a compound of Formula (XIb) with conc. HCl, in a polar aprotic solvent, such as in toluene, at an appropriate temperature, for example at r.t.

Experimental Procedure 8

According to the Reaction scheme 8, intermediate of Formula (IVc), wherein $R_1=R_3=R_4=H$, and $R_2=Me$, can be prepared from intermediate (IXc), wherein $R_1=R_4=H$ and Hal is Iodine.

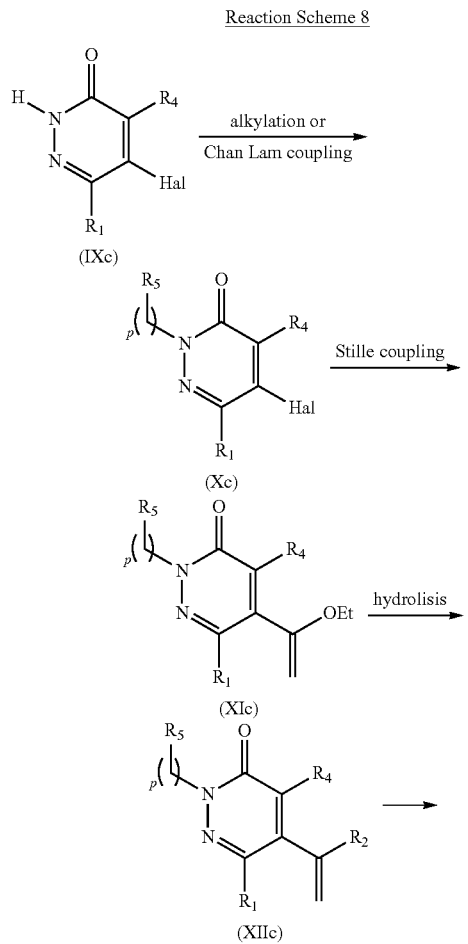

A compound of Formula (Xc) can be prepared reacting a compound of Formula (IXc) in an alkylation reaction with an alkyl halide (i.e. $R_5(CH_2)_p$-Hal), or in a Chan Lam reaction with a suitable boronic acid or ester (VII). Typical alkylation conditions comprise reacting a compound of formula (IXc) with a suitable alkyl halide, such as benzylbromide, in the presence of a base, such as potassium carbonate, in a polar aprotic solvent, such as in DMF, at an appropriate temperature, for example at r.t. Typical Chan Lam reaction conditions comprise reacting a compound of Formula (IXc) with a suitable boronic acid or ester (VII), such as phenylboronic acid, in the presence of copper (II) acetate and pyridine, in a mixture of polar aprotic solvents, such as DCM and DMF, at an appropriate temperature, for example at r.t., in the open air. A compound of formula (Xc) wherein $R_1=R_4=H$, $R_5=Me$, P=0, can be prepared accordingly to the procedure reported in *Tetrahedron*, 2004, 60, 12177-12189, which is incorporated herein by reference in its entirety. A compound of Formula (IXc) wherein $R_1=R_4=H$ and Hal is Iodine, can be prepared accordingly to the procedure reported in *Bioorg. Med. Chem.* 2012, 20, 3880-3886, which is incorporated herein by reference in its entirety. Intermediate of formula (Xc) was then reacted with tributyl(1-ethoxyvinyl)tin under Stille cross-coupling conditions. Typical reaction conditions comprise reacting a compound of Formula (Xc) with tributyl(1-ethoxyvinyl)tin, in the presence of a Pd catalyst, such as bis(triphenylphosphine)-palladium(II) dichloride, in a polar aprotic solvent, such as in toluene, at an appropriate temperature, for example at 110° C. Intermediate of Formula (XIc) was hydrolyzed to ketone of Formula (XIIc) with HCl. Typical reaction conditions comprise reacting a compound of Formula (XIc) with conc. HCl, in a polar aprotic solvent, such as in toluene, at an appropriate temperature, for example at r.t. Finally, an intermediate of formula (XIIc) can be converted into alcohol (IVc), wherein $R_1=R_3=R_4=H$, and $R_2=Me$. Typical reduction conditions comprise reacting a compound of formula (XIIc) with a reducing reagent, such as $NaBH_4$, in a mixture of polar aprotic and protic solvents, such as THF and MeOH, at an appropriate temperature, for example at r.t. The crude obtained from reduction of a compound of formula (XIIc) was partially oxidized with a suitable oxidant such as $CuCl_2$ in a polar aprotic solvent, such as $CH_3CN$, at an appropriate temperature, such as at 85° C., or sodium 3-nitrobenzenesulfonate in aqueous NaOH, at an appropriate temperature, such as heating to reflux.

Experimental Procedure 9

According to the Reaction scheme 9, intermediate of Formula (IVd), wherein $R_1$, $R_2$, $R_3$, $R_4=H$, can be prepared from intermediate (XXII), wherein $R_1=R_4=H$.

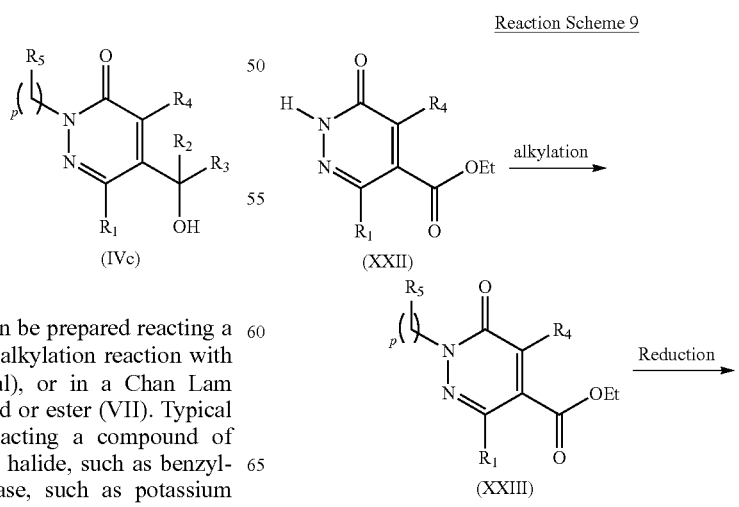

-continued

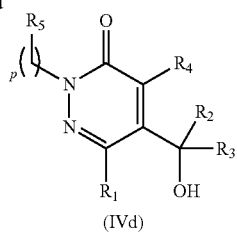

(IVd)

An intermediate of Formula (XXIII) can be prepared by reaction of a compound of formula (XXII) in an alkylation reaction. Typical alkylation conditions comprise reacting a compound of formula (XXII) with a suitable alkyl halide, such as benzyl bromide, in the presence of a base, such as potassium carbonate, in a polar aprotic solvent, such as DMF, at an appropriate temperature, for example at r.t. A compound of formula (XXII) can be prepared accordingly to the procedure reported in US2009/111821 A1, which is incorporated herein by reference in its entirety. An intermediate of Formula (IVd) may be prepared by reduction of a compound of formula (XXIII) followed by oxidation of the obtained crude. Typical reduction conditions comprise reacting a compound of formula (XXIII) with a reducing reagent, such as $NaBH_4$ in the presence of $CaCl_2$, in a mixture of polar aprotic and protic solvents, such as THF and MeOH, at an appropriate temperature, for example at r.t. Typical oxidation conditions comprise reacting the crude obtained from reduction of a compound of formula (XXIII) with an oxidation system, such as $CuCl_2$ in a polar aprotic solvent, such as $CH_3CN$, at an appropriate temperature, such as at 85° C.

The compounds of the present invention are inhibitors of kinase activity, in particular PI3-kinase activity. Generally speaking, compounds which are PI3K inhibitors may be useful in the treatment of many disorders associated with PI3K enzymes mechanisms.

In one embodiment, the disorders that can be treated by the compounds of the present invention include respiratory diseases selected from idiopathic chronic cough, cough-variant asthma, cough associated with thoracic tumour or lung cancer, viral or post-viral cough, upper airways cough syndrome (UACS), or post nasal drip cough, or cough associated with gastro-oesophageal reflux disease (both acid and non-acid reflux), asthma, chronic bronchitis, chronic obstructive pulmonary disease (COPD), interstitial lung disease, (such as idiopathic pulmonary fibrosis (IPF)), congestive heart disease, sarcoidosis, infections (such as whooping cough); viral infections (including viral respiratory tract infections and viral exacerbation of respiratory diseases; non-viral respiratory infections including aspergillosis and leishmaniasis; allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trauma), trigeminal neuralgia and central pain.

In another embodiment, the disorder that can be treated by the compound of the present invention is selected from the group consisting of idiopathic chronic cough, cough-variant asthma, cough associated with thoracic tumour or lung cancer, viral or post-viral cough, upper airways cough syndrome (UACS), post nasal drip cough, cough associated gastro-oesophageal reflux disease (both acid and non-acid reflux), asthma, chronic bronchitis, chronic obstructive pulmonary disease (COPD) and interstitial lung disease (such as idiopathic pulmonary fibrosis (IPF)).

In a further embodiment, the disorder is selected from the group of asthma, chronic obstructive pulmonary disease (COPD), idiopathic pulmonary fibrosis (IPF), cough, and chronic cough.

The methods of treatment of the present invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan. The compounds of formula (I) or pharmaceutically acceptable salts and or solvates thereof may be administered once or according to a dosing regimen wherein a number of doses are administered at varying intervals of time for a given period of time. Typical daily dosages may vary depending upon the particular route of administration chosen.

The invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A., which is incorporated herein by reference in its entirety.

Administration of the compounds of the present invention and their pharmaceutical compositions may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the present invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the present invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the present invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such suitable carriers, as are also known.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation. Inhalable preparations include inhalable powders, propellant-containing metering aerosols, or propellant-free inhalable formulations.

For administration as a dry powder, single- or multi-dose inhalers known from the prior art may be utilized. In that case, the powder may be filled in gelatine, plastic, or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the present invention.

Inhalation aerosols containing a propellant gas such as a hydrofluoroalkane may contain the compounds of the present invention either in solution or in dispersed form. The propellant-driven formulations may also contain other ingredients such as co-solvents, stabilizers and optionally other excipients.

The propellant-free inhalable formulations comprising the compounds of the present invention may be in form of solutions or suspensions in an aqueous, alcoholic, or hydroalcoholic medium and they may be delivered by jet or ultrasonic nebulizers known from the prior art or by soft-mist nebulizers such as Respimat®.

The compounds of the present invention can be administered as the sole active agent or in combination with other pharmaceutical active ingredients including those currently used in the treatment of respiratory disorders, e.g. beta$_2$-agonists, antimuscarinic agents, corticosteroids, mitogen-activated kinases (P38 MAP kinases) inhibitors, human neutrophil elastase (HNE) inhibitors, phosphodiesterase 4 (PDE4) inhibitors, leukotriene modulators, non-steroidal anti-inflammatory agents (NSAIDs), and mucus regulators.

The dosage of the compounds of the present invention depends upon a variety of factors including the particular disease to be treated, the severity of the symptoms, the route of administration, the frequency of the dosage interval, the particular compound utilized, and the efficacy, toxicology profile, and pharmacokinetic profile of the compound. Advantageously, the compounds of formula (I) can be administered for example, at a dosage of 0.001 to 1000 mg/day, preferably 0.1 to 500 mg/day. When the compounds of formula (I) are administered by inhalation route, they are preferably given at a dosage of 0.001 to 500 mg/day, preferably 0.1 to 200 mg/day.

Other features of the invention will become apparent in the course of the following descriptions of exemplary embodiments which are given for illustration of the invention and are not intended to be limiting thereof.

EXAMPLES

Preparation of Intermediates and Examples

Chemical Names of the compounds were generated with CHEMAXON 6.0.4 tool. Solutions of common inorganic salts used in workups are aqueous solutions.

| Abbreviations: | |
|---|---|
| EtOAc | Ethyl acetate |
| DCM | Dichloromethane |
| MeOH | Methanol |
| DMF | N,N-Dimethylformamide |
| MeCN | Acetonitrile |
| THF | Tetrahydrofuran |
| DMSO | Dimethyl sulfoxide |
| t-BuOH | tert-Butanol |
| EtOH | Ethanol |
| DME | 1,2-Dimethoxyethane |
| PdCl$_2$(PPh$_3$)$_2$ | Bis(triphenylphosphine)palladium(II) dichloride |
| Pd(OAc)$_2$ | Palladium(II) acetate |
| Pd(PPh$_3$)$_4$ | Tetrakis(triphenylphosphine)palladium(0) |
| PPH$_3$ | Triphenylphosphine |
| DPPA | Diphenyl phosphoryl azide |
| DBU | 1,8-Diazabicyclo[5.4.0]undec-7-ene |
| DIPEA | N,N-Diisopropylethylamine |
| MeMgBr | Methylmagnesium bromide |
| EtMgBr | Ethylmagnesium bromide |
| PhMgCl | Phenylmagnesium chloride |
| DIAD | Diisopropyl azodicarboxylate |
| TFA | Trifluoroacetic acid |
| MW | Microwave |
| SCX | Strong cation exchanger |
| Silica NH | Secondary amine functionalized silica cartridge |
| r.t./RT | Room temperature |
| Rt | Retention time |
| H | Hour |
| Min | Minutes |
| Conc | Concentrated |
| Eq | Equivalent |
| Sat | Saturated |
| MDAP | Mass directed autopurification |

General Experimental Details.
NMR Characterization:

Proton Magnetic Resonance ($^1$H NMR) spectra were collected using deuterated solvents (DMSO-d$_6$, CDCl$_3$) at 25° C. on Agilent VNMRS-500, Agilent VNMRS-400, and Bruker Avance 400. Chemical shifts are expressed in parts per million (ppm) downfield of tetramethylsilane (δ units). Multiplicity is indicated as follow: (s) singlet, (d) doublet, (dd) double doublet, (ddd) triple doublet, (t) triplet, (dt) double triplet, (q) quartet, (m) multiplet, (br s) broad signal. Coupling constants J are expressed in unit of hertz (Hz).
LC/UV/MS Analytical Methods:

LCMS may be recorded under the following conditions: diode array detector DAD chromatographic traces, mass chromatograms and mass spectra may be taken on UPLC/PDA/MS Acquity™ system coupled with Micromass ZQ™ or Waters SQD single quadrupole mass spectrometer operated in positive and/or negative electron spray ES ionization mode and/or Fractionlynx system used in analytical mode coupled with ZQ™ single quadrupole operated in positive and/or negative ES ionization mode.

Quality Control methods used were two: one operated under low pH conditions and the other one operated under high pH conditions:

Method A, low pH conditions: column: Acquity CSH C18, 1.7 µm, 2.1×50 mm, the column temperature was 40° C.; mobile phase solvent A was milliQ water+0.1% HCOOH, mobile phase solvent B MeCN+0.1% HCOOH.

The flow rate was 1 ml/min. The gradient table was t=0 min 97% A–3% B, t=1.5 min 0.1% A–99.9% B, t=1.9 min 0.1% A–99.9% B and t=2 min 97% A–3% B. The UV detection range was 210-350 nm and the ES+/ES− range was 100-1000 amu.

Method B, low pH conditions: column: Acquity UPLC BEH C18, 1.7 µm, 50 mm×2.1 mm, the column temperature was 40° C.; mobile phase solvent A was milliQ water+0.1% HCOOH, mobile phase solvent B MeCN+0.1% HCOOH. The flow rate was 1 ml/min. The gradient table was t=0 min 97% A–3% B, t=1.5 min 0.1% A–99.9% B, t=1.9 min 0.1% A–99.9% B and t=2 min 97% A–3% B. The UV detection range was 210-350 nm and the ES+/ES− range was 100-1000 amu.

Experiments performed under microwave irradiation were carried out using a Biotage Initiator 2.0 system.

Flash chromatography purifications were performed using Biotage Isolera or Biotage SP1 flash chromatography systems, both instruments working with Biotage KP-SIL cartridges and Biotage KP-NH cartridges, or were manually performed using Isolute Flash silica gel pre-packed cartridges, or Varian Bond Elut pre-packed cartridges.

Reverse phase flash chromatography was carried out over pre-packed Biotage C18 SNAP cartridges or Varan Bond Elut C18 cartridges.

SPE-SCX cartridges are ion exchange solid phase extraction columns supplied by Varian.

Many of the compounds described in the following examples have been prepared from stereochemically pure starting materials, for example 95% ee.

Brine refers to a saturated aqueous solution of NaCl, unless otherwise specified.

Where the preparation of starting materials is not described, these are known, commercially available, or readily obtainable using standard procedures.

The stereochemistry of the compounds in the examples, where indicated, has been assigned on the assumption that absolute configuration at resolved stereogenic centers of staring materials is maintained throughout any subsequent reaction conditions.

In the procedures that follow, after each starting material, reference to a compound number is sometimes provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Intermediate A1: 2-benzyl-5-bromo-6-phenyl-2,3-dihydropyridazin-3-one

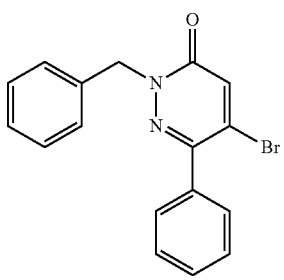 [SMILES: O=c1cc(Br)c(-c2ccccc2)nn1Cc1ccccc1]

To a solution of 5-bromo-6-phenyl-2,3-dihydropyridazin-3-one (1.0 g, 3.98 mmol) in DMF (20 mL), potassium carbonate (0.661 g, 4.78 mmol) was added followed by benzyl bromide (0.569 mL, 4.78 mmol) and the resulting mixture was stirred at r.t. for 2 h. The mixture was diluted with EtOAc and washed with water and then several times with brine. The organic phase was dried over sodium sulfate and the solvent was removed. The crude was purified by flash chromatography on silica gel Biotage SNAP cartridge (cyclohexane to cyclohexane:EtOAc=80:20) to afford title compound as a yellow solid (1.212 g, 3.55 mmol, 89% yield). MS/ESI$^+$ 341.1-343.1 [MH]$^+$, Rt=1.19 min (Method A).

Intermediate A2: 5-bromo-2-methyl-6-phenyl-2,3-dihydropyridazin-3-one

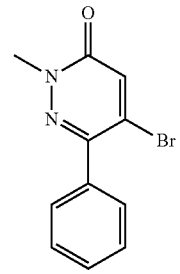

A mixture of 5-bromo-6-phenyl-2,3-dihydropyridazin-3-one (0.500 g, 1.99 mmol) and N,N-dimethylformamide dimethyl acetal (0.397 mL, 2.978 mmol) in DMF (20 mL) was refluxed for 2 h. The mixture was diluted with EtOAc and washed with water and then several times with brine. The organic phase was dried over sodium sulfate and the solvent was removed. The crude was purified by flash chromatography on silica gel Biotage cartridge (cyclohexane:EtOAc=90:10 to 50:50) to afford title compound as a white solid (0.279 g, 1.05 mmol, 53% yield). MS/ESI$^+$ 265.0-267.0 [MH]$^+$, Rt=0.92 min (Method A).

Intermediate A3: 5-bromo-6-phenyl-2-(propan-2-yl)-2,3-dihydropyridazin-3-one

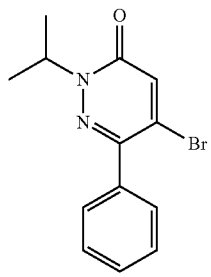 [SMILES: CC(C)n1nc(-c2ccccc2)c(Br)cc1=O]

To a solution of 5-bromo-6-phenyl-2,3-dihydropyridazin-3-one (0.700 g, 2.788 mmol) in DMF (12 mL), potassium carbonate (0.462 g, 3.345 mmol) was added followed by 2-bromopropane (0.314 mL, 3.345 mmol) and the resulting mixture heated at 60° C. for 2 h. The mixture was partitioned between EtOAc and water, the aqueous phase was extracted with EtOAc, and the combined organic layers were washed several times with brine. The organic phase was dried over sodium sulfate and the solvent was removed. The crude was purified by flash chromatography on silica gel Biotage cartridge (cyclohexane to cyclohexane:EtOAc=85:15) to afford title compound as a pale yellow solid (0.630 g, 2.149 mmol, 77% yield). MS/ESI$^+$ 293.1-295.1 [MH]$^+$, Rt=1.11 min (Method A).

Intermediate A4: 5-bromo-2-(oxan-2-yl)-6-phenyl-2,3-dihydropyridazin-3-one

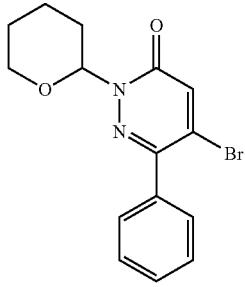 [SMILES: O=c1cc(Br)c(-c2ccccc2)nn1C1CCCCO1]

A mixture of 5-bromo-6-phenyl-2,3-dihydropyridazin-3-one (2.572 g, 10.24 mmol), 3,4-dihydro-2H-pyran (15 mL, 164.4 mmol) and pyridinium p-toluenesulfonate (0.489 g, 1.945 mmol), in THF (12 mL) was heated to reflux for 5 h. Additional 3,4-dihydro-2H-pyran (7.5 mL, 82.2 mmol) was added and the reaction was heated to reflux overnight. The mixture was concentrated in vacuo and the residue was taken up with EtOAc and washed with aqueous 2N sodium hydroxide. The organic phase was dried over sodium sulfate and concentrated in vacuo. The crude was purified by flash chromatography on Biotage silica gel cartridge (cyclohexane:EtOAc=90:10 60:40) to afford title compound as a yellow oil (3.4 g, 10.15 mmol, 99% yield). MS/ESI$^+$ 335.1-337.1 [MH]$^+$, Rt=1.08 min (Method A).

Intermediate B1: 2-benzyl-5-iodo-2,3-dihydropyridazin-3-one

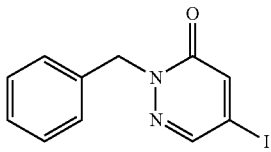 [SMILES: O=c1cc(I)cnn1Cc1ccccc1]

To a solution of 5-iodo-2,3-dihydropyridazin-3-one (prepared according to the procedure reported in *Bioorg. Med. Chem.* 2012, 20, 3880-3886, which is incorporated herein by reference in its entirety) (0.500 g) in DMF (5 mL), potassium carbonate (0.375 g, 2.71 mmol) was added followed by benzyl bromide (0.323 mL, 2.71 mmol) and the resulting mixture was stirred at r.t. for 18 h. The mixture was diluted with EtOAc and washed with water and then several times with brine. The organic phase was dried over sodium sulfate and the solvent was removed in vacuo. The crude was purified by flash chromatography on silica gel Biotage cartridge (cyclohexane to cyclohexane:EtOAc=80:20) to afford title compound as a white solid (0.504 g, 1.61 mmol). MS/ESI$^+$ 312.8 [MH]$^+$, Rt=0.97 min (Method A).

Intermediate B2: 5-iodo-2-phenyl-2,3-dihydropyridazin-3-one

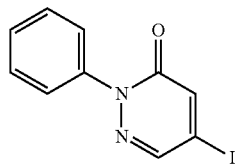 [SMILES: O=c1cc(I)cnn1-c1ccccc1]

To a solution of 5-iodo-2,3-dihydropyridazin-3-one (prepared according to the procedure reported in *Bioorg. Med. Chem.* 2012, 20, 3880-3886, which is incorporated herein by reference in its entirety) (0.500 g) in DCM (24 mL) and DMF (8 mL), copper (II) acetate (0.822 g, 4.52 mmol), phenylboronic acid (0.331 g, 2.71 mmol), pyridine (366 µL, 4.52 mmol) and activated 4 Å molecular sieves (1.200 g) were added and the resulting mixture was stirred at r.t. in the open air for 24 hours. Additional phenylboronic acid (0.331 g, 2.71 mmol) was added and the reaction was stirred for further 4 h. Concentrated NH$_4$OHaq. was added, the volatiles were removed under reduced pressure and the insoluble materials were filtered off; the crude was purified by flash chromatography on silica gel Biotage cartridge (cyclohexane:EtOAc=90:10 to 20:80) to afford title compound (0.513 g). MS/ESI$^+$ 298.8 [MH]$^+$, Rt=0.88 min (Method A).

Intermediate C1: 2-tert-butyl-5-chloro-4-phenyl-2,3-dihydropyridazin-3-one

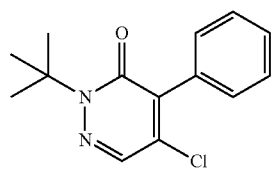 [SMILES: CC(C)(C)n1ncc(Cl)c(-c2ccccc2)c1=O]

To a solution of 2-tert-butyl-4,5-dichloro-2,3-dihydropyridazin-3-one (prepared according to the procedure reported in US2005/0191238 A1, which is incorporated herein by reference in its entirety) (2.00 g, 9.05 mmol) in THF (35 mL) cooled at 0° C., a 2M solution of PhMgCl in THF (5.65 mL, 11.3 mmol) was added and the resulting mixture was stirred at 0° C. for 30 min. Additional 2M PhMgCl in THF (5.65 mL, 11.3 mmol) was added at 0° C. and the mixture was stirred at the same temperature for 1 h. The reaction was quenched at 0° C. by drop-wise addition of aqueous 6M HCl (5 mL). The mixture was extracted with AcOEt, and the organic phase was washed with water and brine and then dried over sodium sulfate. The solvent was removed and the crude was purified by flash chromatography on Biotage silica gel cartridge (cyclohexane to cyclohexane:EtOAc=95:5) to afford title compound as a pale yellow oil (1.190 g, 4.53 mmol, 50% yield). MS/ESI$^+$ 263.2 [MH]$^+$, Rt=1.25 min (Method A).

Intermediate C2: 2-tert-butyl-5-chloro-4-cyclopentyl-2,3-dihydropyridazin-3-one

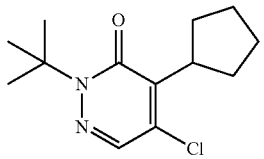 [SMILES: CC(C)(C)n1ncc(Cl)c(C2CCCC2)c1=O]

Prepared similarly to intermediate C1, starting from 2-tert-butyl-4,5-dichloro-2,3-dihydropyridazin-3-one (prepared according to the procedure reported in US2005/0191238 A1, which is incorporated herein by reference in its entirety) (2.00 g, 9.05 mmol) and 2.0 M cyclopentylmagnesium chloride in diethyl ether (5.65 mL, 11.3 mmol), stirring for 30 min, and purified by flash chromatography on Biotage silica gel cartridge (cyclohexane to cyclohexane:EtOAc=95:5) to afford title compound as a pale yellow oil (1.278 g, 5.03 mmol, 56% yield). MS/ESI$^+$ 255.2 [MH]$^+$, Rt=1.52 min (Method A).

Intermediate C3: 5-chloro-4-cyclopentyl-2,3-dihydropyridazin-3-one

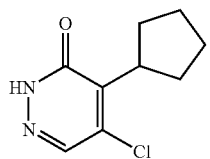 [SMILES: O=c1[nH]ncc(Cl)c1C1CCCC1]

2-tert-butyl-5-chloro-4-cyclopentyl-2,3-dihydropyridazin-3-one C2 (1.126 g, 4.43 mmol) was dissolved in conc. H$_2$SO$_4$ (22.2 mL) and conc. HNO$_3$ (7.4 mL) was added drop-wise maintaining the temperature below 30° C. and the mixture was stirred at r.t. for 1 h. Then the mixture was poured into ice water (20 ml), whereupon precipitated crystals were collected by filtration, washed with water and dried under reduced pressure to provide title compound (0.632 g, 3.19 mmol, 72% yield). MS/ESI$^+$ 199.1 [MH]$^+$, Rt=0.93 min (Method A).

Intermediate C4: 2-benzyl-5-chloro-4-cyclopentyl-2,3-dihydropyridazin-3-one

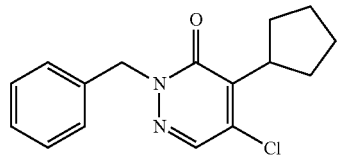 [SMILES: O=c1c(C2CCCC2)c(Cl)cnn1Cc1ccccc1]

To a solution of 5-chloro-4-cyclopentyl-2,3-dihydropyridazin-3-one C3 (0.350 g, 1.76 mmol) in DMF (12 mL), potassium carbonate (0.293 g, 2.12 mmol) was added followed by benzyl bromide (0.252 mL, 2.12 mmol) and the resulting mixture was stirred at r.t. for 3 h. The mixture was partitioned between EtOAc and water and the organic phase was washed several times with brine and dried over sodium sulfate. The solvent was removed and the crude was purified by flash chromatography on Biotage silica gel cartridge (cyclohexane to cyclohexane:EtOAc=80:20) to afford title compound as a white solid (0.389 g, 1.35 mmol, 77% yield). MS/ESI$^+$ 289.2 [MH]$^+$, Rt=1.39 min (Method A).

Intermediate D1: 2-benzyl-5-(1-ethoxyethenyl)-6-phenyl-2,3-dihydropyridazin-3-one

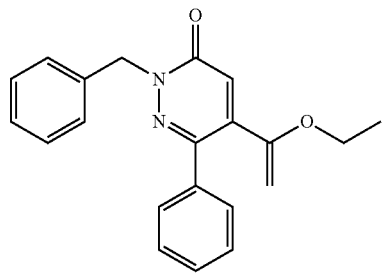 [SMILES: C=C(OCC)c1cc(=O)n(Cc2ccccc2)nc1-c1ccccc1]

To a solution of 2-benzyl-5-bromo-6-phenyl-2,3-dihydropyridazin-3-one A1 (1.212 g, 3.55 mmol) in toluene (15 mL), bis(triphenylphosphine)palladium(II) dichloride (0.125 g, 0.17 mmol) was added followed by tributyl(1-ethoxyvinyl)tin (1.3 mL, 3.9 mmol) and the resulting mixture was heated to reflux for 2 h. The mixture was allowed to cool to r.t. and then filtered through a celite pad. The filtrate was evaporated to dryness and the crude was purified by flash chromatography on silica gel Biotage cartridge (cyclohexane to cyclohexane:EtOAc=60:40) to afford title compound (1.17 g, 3.52 mmol, 99% yield). MS/ESI$^+$ 333.2 [MH]$^+$, Rt=1.28 min (Method A).

Intermediate D2: 5-(1-ethoxyethenyl)-2-methyl-6-phenyl-2,3-dihydropyridazin-3-one

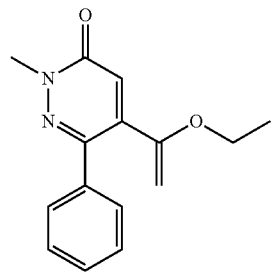 [SMILES: C=C(OCC)c1cc(=O)n(C)nc1-c1ccccc1]

Prepared similarly to intermediate D1 starting from 5-bromo-2-methyl-6-phenyl-2,3-dihydropyridazin-3-one A2 (0.279 g, 1.05 mmol), and purified by flash chromatography on silica gel Biotage cartridge (cyclohexane:EtOAc=93:7 to 40:60) to afford title compound (0.264 g, 1.03 mmol, 98% yield). MS/ESI$^+$ 257.2 [MH]$^+$, Rt=1.01 min (Method A).

Intermediate D3: 5-(1-ethoxyethenyl)-6-phenyl-2-(propan-2-yl)-2,3-dihydropyridazin-3-one

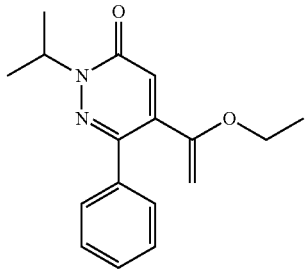 [SMILES: C=C(OCC)c1cc(=O)n(C(C)C)nc1-c1ccccc1]

Prepared similarly to intermediate D1 starting from 5-bromo-6-phenyl-2-(propan-2-yl)-2,3-dihydropyridazin-3-one A3 (0.625 g, 2.132 mmol), and purified by flash chromatography on silica gel Biotage cartridge (cyclohexane to cyclohexane:EtOAc=80:20); the obtained product was dissolved in EtOAc and vigorously stirred with aqueous sat. KF for 15 min. The phases were separated and the organic layer was evaporated to dryness to afford title compound as pale brown solid (0.555 g, 1.952 mmol, 91% yield). MS/ESI$^+$ 285.2 [MH]$^+$, Rt=1.20 min (Method A).

Intermediate D4: 5-(1-ethoxyethenyl)-2-(oxan-2-yl)-6-phenyl-2,3-dihydropyridazin-3-one

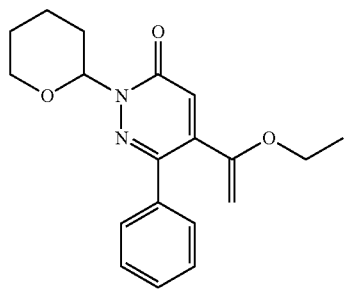 [SMILES: C=C(OCC)c1cc(=O)n(C2CCCCO2)nc1-c1ccccc1]

Prepared similarly to intermediate D1 starting from 5-bromo-2-(oxan-2-yl)-6-phenyl-2,3-dihydropyridazin-3-one A4 (3.4 g, 10.15 mmol), and purified by flash chromatography on silica gel Biotage cartridge (cyclohexane:EtOAc=93:7 to 40:60) to afford title compound (3.308 g, 10.15 mmol, quantitative yield). MS/ESI$^+$ 327.3 [MH]$^+$, Rt=1.16 min (Method A).

Intermediate D5: 2-benzyl-5-(1-ethoxyethenyl)-2,3-dihydropyridazin-3-one

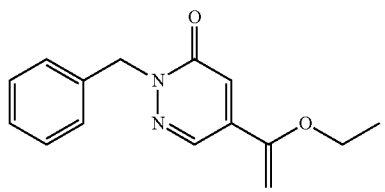 [SMILES: C=C(OCC)c1cnn(Cc2ccccc2)c(=O)c1]

Prepared similarly to intermediate D1 starting from 2-benzyl-5-iodo-2,3-dihydropyridazin-3-one B1 (0.504 g, 1.61 mmol), and purified by flash chromatography on silica gel Biotage cartridge (cyclohexane:EtOAc=93:7 to 40:60) to afford title compound (0.372 g, 1.45 mmol, 90% yield). MS/ESI$^+$ 257.0 [MH]$^+$, Rt=1.04 min (Method A).

Intermediate D6: 5-(1-ethoxyethenyl)-2-phenyl-2,3-dihydropyridazin-3-one

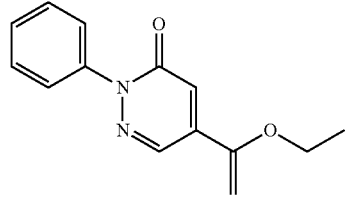 [SMILES: C=C(OCC)c1cnn(-c2ccccc2)c(=O)c1]

Prepared similarly to intermediate D1 starting from 5-iodo-2-phenyl-2,3-dihydropyridazin-3-one B2 (0.513 g), and purified by flash chromatography on silica gel Biotage cartridge (cyclohexane:EtOAc=93:7 to 40:60) to afford title compound (0.374 g, 1.55 mmol). MS/ESI$^+$ 243.0 [MH]$^+$, Rt=0.98 min (Method A).

Intermediate D7: 5-(1-ethoxyethenyl)-2-methyl-2,3-dihydropyridazin-3-one

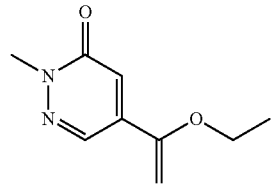

Prepared similarly to intermediate D1 starting from 5-iodo-2-methyl-2,3-dihydropyridazin-3-one (prepared according to the procedure reported in Tetrahedron, 2004, 60, 12177-12189, which is incorporated herein by reference in its entirety) (0.904 g), and purified by flash chromatography on silica gel Biotage cartridge (cyclohexane:EtOAc=93:7 to =40:60) to afford title compound (0.659 g, 3.66 mmol). MS/ESI$^+$ 181.1 [MH]$^+$, Rt=0.73 min (Method A).

Intermediate D8: 2-tert-butyl-5-(1-ethoxyethenyl)-4-phenyl-2,3-dihydropyridazin-3-one

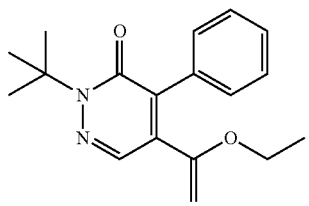 [SMILES: C=C(OCC)c1cnn(C(C)(C)C)c(=O)c1-c1ccccc1]

To a degassed solution of 2-tert-butyl-5-chloro-4-phenyl-2,3-dihydropyridazin-3-one C1 (1.190 g, 4.53 mmol) in toluene (20 mL), PdCl$_2$(PPh$_3$)$_2$ (0.159 g, 0.226 mmol) was added followed by tributyl(1-ethoxyvinyl)tin (1.683 mL, 4.98 mmol) and the resulting mixture was heated to reflux overnight. The mixture was allowed to cool to r.t. and then filtered through a celite pad. The filtrate was evaporated to dryness and the crude was purified by flash chromatography on silica gel Biotage cartridge (cyclohexane to cyclohexane: EtOAc=95:5) to afford title compound as a pale yellow oil (1.074 g, 3.60 mmol, 79% yield). MS/ESI$^+$ 299.3 [MH]$^+$, Rt=1.29 min (Method A).

Intermediate D9: 2-benzyl-4-cyclopentyl-5-(1-ethoxyethenyl)-2,3-dihydropyridazin-3-one

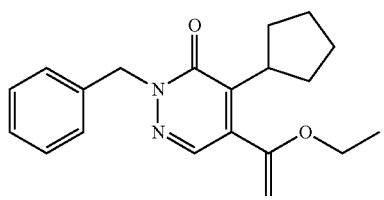 [SMILES: C=C(OCC)c1cnn(Cc2ccccc2)c(=O)c1C1CCCC1]

Prepared similarly to intermediate D8 starting from 2-benzyl-5-chloro-4-cyclopentyl-2,3-dihydropyridazin-3-one C4 (0.389 g, 1.35 mmol), and purified by flash chromatography on silica gel Biotage cartridge (cyclohexane to cyclohexane:EtOAc=90:10) to afford title compound as a pale yellow oil (0.410 g, 1.26 mmol, 94% yield). MS/ESI$^+$ 325.3 [MH]$^+$, Rt=1.42 min (Method A).

Intermediate E1: 5-acetyl-2-benzyl-6-phenyl-2,3-dihydropyridazin-3-one

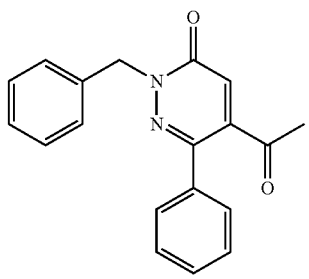 [SMILES: CC(=O)c1cc(=O)n(Cc2ccccc2)nc1-c1ccccc1]

To a solution of 2-benzyl-5-(1-ethoxyethenyl)-6-phenyl-2,3-dihydropyridazin-3-one D1 (1.17 g, 3.52 mmol) in toluene (15 mL), aqueous 37% HCl (0.75 mL) was added and the resulting mixture was stirred at r.t. for 12 h. The mixture was extracted with DCM, the organic phase was dried over sodium sulfate and the solvent evaporated to afford title compound (1.066 g, 3.5 mmol, 99% yield). MS/ESI$^+$ 305.2 [MH]$^+$, Rt=1.07 min (Method A).

Intermediate E2: 5-acetyl-2-methyl-6-phenyl-2,3-dihydropyridazin-3-one

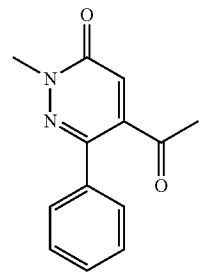 [SMILES: CC(=O)c1cc(=O)n(C)nc1-c1ccccc1]

Prepared similarly to intermediate E1 starting from 5-(1-ethoxyethenyl)-2-methyl-6-phenyl-2,3-dihydropyridazin-3-one D2 (0.264 g, 1.03 mmol), and purified by flash chromatography on silica gel Biotage cartridge (cyclohexane: EtOAc=90:10 to 20:80) to afford title compound (0.204 g, 0.894 mmol, 87% yield). MS/ESI$^+$ 229.1 [MH]$^+$, Rt=0.78 min (Method A).

Intermediate E3: 5-acetyl-6-phenyl-2-(propan-2-yl)-2,3-dihydropyridazin-3-one

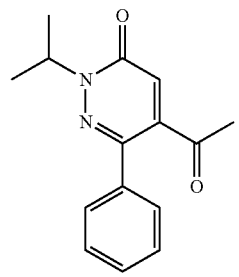 [SMILES: CC(=O)c1cc(=O)n(C(C)C)nc1-c1ccccc1]

Prepared similarly to intermediate E1 starting from 5-(1-ethoxyethenyl)-6-phenyl-2-(propan-2-yl)-2,3-dihydropyridazin-3-one D3 (0.515 g, 1.811 mmol), stirring for 2 h, to afford title compound as a beige solid (0.442 g, 1.724 mmol, 95% yield). MS/ESI$^+$ 257.2 [MH]$^+$, Rt=0.98 min (Method A).

Intermediate E4: 5-acetyl-6-phenyl-2,3-dihydropyridazin-3-one

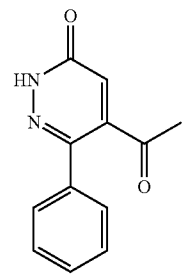 [SMILES: CC(=O)c1cc(=O)[nH]nc1-c1ccccc1]

A mixture of 5-(1-ethoxyethenyl)-2-(oxan-2-yl)-6-phenyl-2,3-dihydropyridazin-3-one D4 (3.308 g, 10.15 mmol)

in aqueous 6N HCl (30 mL) was heated to reflux for 2 h. The mixture was extracted with DCM, the organic layer was dried over sodium sulfate and the solvent evaporated. The crude was purified by flash chromatography on silica gel Biotage cartridge (cyclohexane:EtOAc=90:10 to =20:80) to afford an orange solid which was recrystallized from 2-propanol to afford title compound as a pale yellow solid (1.486 g, 6.9 mmol, 68% yield). The mother liquor was recovered to afford a second fraction of title compound which was used without any additional purification (0.771 g). MS/ESI+ 215.1 [MH]+, Rt=0.67 min (Method A).

Intermediate E5: 5-acetyl-2-(cyclopropylmethyl)-6-phenyl-2,3-dihydropyridazin-3-one

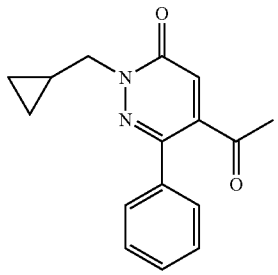 [SMILES: CC(=O)c1cc(=O)n(CC2CC2)nc1-c1ccccc1]

To a solution of 5-acetyl-6-phenyl-2,3-dihydropyridazin-3-one E4 (0.300 g) in DMF (6 mL), potassium carbonate (0.232 g, 1.68 mmol) was added followed by (bromomethyl) cyclopropane (0.163 mL, 1.68 mmol) and the resulting mixture was stirred at r.t. for 2 h. The mixture was diluted with EtOAc, washed with water and then several times with brine. The organic phase was dried over sodium sulfate and the solvent was removed in vacuo. The crude was purified by flash chromatography on silica gel Biotage cartridge (cyclohexane to cyclohexane:EtOAc=60:40) to afford title compound as a yellow oil (0.212 g, 0.79 mmol). MS/ESI+ 269.2 [MH]+, Rt=0.99 min (Method A).

Intermediate E6: 5-acetyl-2,6-diphenyl-2,3-dihydropyridazin-3-one

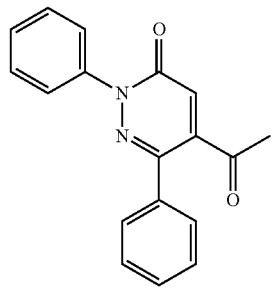 [SMILES: CC(=O)c1cc(=O)n(-c2ccccc2)nc1-c1ccccc1]

To a solution of 5-acetyl-6-phenyl-2,3-dihydropyridazin-3-one E4 (0.214 g) in DCM (12 mL) and DMF (4 mL), copper (II) acetate (0.363 g, 2 mmol), phenylboronic acid (0.146 g, 1.2 mmol), pyridine (0.162 mL, 2 mmol) and activated 4 Å molecular sieves (1.200 g) were added and the resulting mixture was stirred at r.t. in the open air for 24 h. Additional phenylboronic acid (0.146 g, 1.2 mmol) was added and the stirring was continued for further 4 h. Concentrated aqueous NH4OH was added, the solvents were evaporated under vacuum and the insoluble materials were filtered off; the crude was purified by flash chromatography on silica gel Biotage cartridge (cyclohexane:EtOAc=90:10 to =20:80) to afford title compound (0.290 g, 1 mmol). MS/ESI+ 291.1 [MH]+, Rt=1.01 min (Method A).

Intermediate E7: 5-acetyl-6-phenyl-2-(pyridin-2-ylmethyl)-2,3-dihydropyridazin-3-one

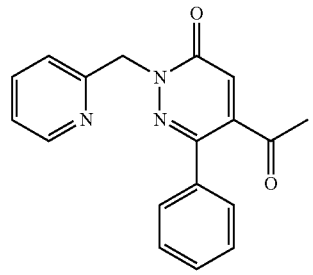 [SMILES: CC(=O)c1cc(=O)n(Cc2ccccn2)nc1-c1ccccc1]

To a solution of 5-acetyl-6-phenyl-2,3-dihydropyridazin-3-one E4 (0.300 g) in DMF (3 mL), potassium carbonate (0.518 g, 4.2 mmol) was added followed by 2-(bromomethyl)pyridine hydrobromide (0.709 g, 2.8 mmol) and the resulting mixture was stirred at r.t. for 1 h. The mixture was diluted with EtOAc and washed with water and then several times with brine. The organic phase was dried over sodium sulfate and the solvent was removed in vacuo. The crude was purified by flash chromatography on silica gel Biotage cartridge (cyclohexane:EtOAc=80:20 to 100% EtOAc) to afford title compound as a yellow oil (0.268 g, 0.878 mmol). MS/ESI+ 306.2 [MH]+, Rt=0.77 min (Method A).

Intermediate E8: 5-acetyl-2-benzyl-2,3-dihydropyridazin-3-one

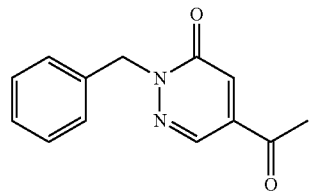 [SMILES: CC(=O)c1cnn(Cc2ccccc2)c(=O)c1]

Prepared similarly to intermediate E1 starting from 2-benzyl-5-(1-ethoxyethenyl)-2,3-dihydropyridazin-3-one D5 (0.372 g, 1.45 mmol) to afford title compound (0.288 g, 1.26 mmol, 87% yield). MS/ESI+ 229.0 [MH]+, Rt=0.81 min (Method A).

Intermediate E9: 5-acetyl-2-phenyl-2,3-dihydropyridazin-3-one

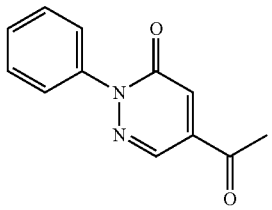 [SMILES: CC(=O)c1cnn(-c2ccccc2)c(=O)c1]

Prepared similarly to intermediate E1 starting from 5-(1-ethoxyethenyl)-2-phenyl-2,3-dihydropyridazin-3-one D6 (0.374 g, 1.55 mmol) to afford title compound (0.262 g, 1.22 mmol, 79% yield). MS/ESI$^+$ 214.9 [MH]$^+$, Rt=0.70 min (Method A).

Intermediate E10: 5-acetyl-2-methyl-2,3-dihydropyridazin-3-one

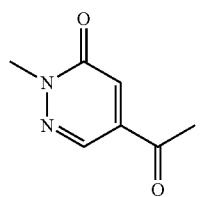

Prepared similarly to intermediate E1 starting from 5-(1-ethoxyethenyl)-2-methyl-2,3-dihydropyridazin-3-one D7 (0.735 g, 4.08 mmol) and purified by flash chromatography on silica gel Biotage cartridge (cyclohexane:EtOAc=90:10 to =20:80) to afford title compound (0.544 g, 3.57 mmol, 88% yield). MS/ESI$^+$ 153.1 [MH]$^+$, Rt=0.42 min (Method A).

Intermediate E11: 5-acetyl-2-tert-butyl-4-phenyl-2,3-dihydropyridazin-3-one

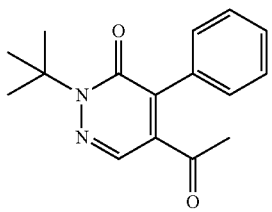 [SMILES: CC(=O)c1cnn(C(C)(C)C)c(=O)c1-c1ccccc1]

Prepared similarly to intermediate E1 starting from 2-tert-butyl-5-(1-ethoxyethenyl)-4-phenyl-2,3-dihydropyridazin-3-one D8 (1.074 g, 3.60 mmol), stirring for 2 h, to afford title compound as a pale yellow solid (0.847 g, 3.13 mmol, 87% yield). MS/ESI$^+$ 271.0 [MH]$^+$, Rt=1.10 min (Method A).

Intermediate E12: 5-acetyl-4-phenyl-2,3-dihydropyridazin-3-one

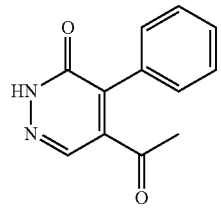 [SMILES: CC(=O)c1cn[nH]c(=O)c1-c1ccccc1]

5-acetyl-2-tert-butyl-4-phenyl-2,3-dihydropyridazin-3-one E11 (0.645 g, 2.386 mmol) was dissolved in TFA (16 mL), and the resulting mixture was heated to reflux overnight and then heated under MW irradiation at 120° C. for 8 h. The volatiles were removed under vacuum and the brown residue was triturated with EtOAc. The precipitate was collected by filtration to afford title compound as a pale yellow solid (0.275 g, 1.284 mmol, 54% yield). MS/ESI$^+$ 215.1 [MH]$^+$, Rt=0.65 min (Method A).

Intermediate E13: 5-acetyl-2-benzyl-4-phenyl-2,3-dihydropyridazin-3-one

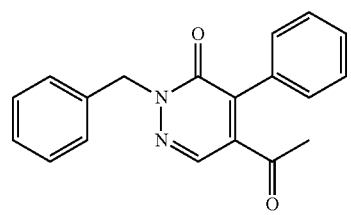 [SMILES: CC(=O)c1cnn(Cc2ccccc2)c(=O)c1-c1ccccc1]

To a solution of 5-acetyl-4-phenyl-2,3-dihydropyridazin-3-one E12 (0.092 g, 0.429 mmol) in DMF (3 mL), potassium carbonate (0.071 g, 0.515 mmol) was added followed by benzyl bromide (0.061 mL, 0.515 mmol) and the resulting mixture was stirred at r.t. for 4 h. The mixture was partitioned between EtOAc and water and the organic phase was washed several times with brine and dried over sodium sulfate. The solvent was removed and the crude was purified by flash chromatography on silica gel Biotage cartridge (cyclohexane to cyclohexane:EtOAc=80:20) to afford title compound as a white solid (0.105 g, 0.345 mmol, 80% yield). MS/ESI$^+$ 305.2 [MH]$^+$, Rt=1.08 min (Method A).

Intermediate E14: 5-acetyl-2-methyl-4-phenyl-2,3-dihydropyridazin-3-one

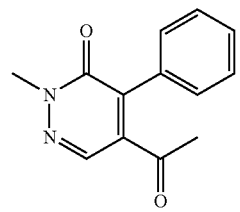 [SMILES: CC(=O)c1cnn(C)c(=O)c1-c1ccccc1]

To a solution of 5-acetyl-4-phenyl-2,3-dihydropyridazin-3-one E12 (0.090 g, 0.42 mmol) in DMF (3 mL), potassium carbonate (0.069 g, 0.50 mmol) was added followed by iodomethane (0.063 mL, 1.01 mmol) and the resulting mixture was stirred at r.t. for 8 h. The mixture was partitioned between EtOAc and water, the organic phase was extracted with EtOAc and the combined organic layers were washed several times with brine and dried over sodium sulfate. The solvent was removed and the crude was purified by flash chromatography on silica gel Biotage cartridge (cyclohexane to cyclohexane:EtOAc=65:35) to afford title compound as a pale orange solid (0.075 g, 0.329 mmol, 78% yield). MS/ESI$^+$ 229.1 [MH]$^+$, Rt=0.75 min (Method A).

Intermediate E15:
5-acetyl-2,4-diphenyl-2,3-dihydropyridazin-3-one

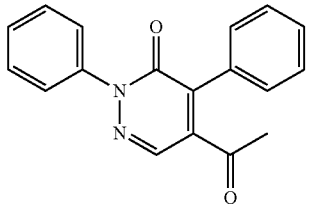 [SMILES: CC(=O)c1cnn(-c2ccccc2)c(=O)c1-c1ccccc1]

To a solution of 5-acetyl-4-phenyl-2,3-dihydropyridazin-3-one E12 (0.092 g, 0.429 mmol) in DCM (4.5 mL) and DMF (1.5 mL), copper (II) acetate (0.156 g, 0.859 mmol), phenylboronic acid (0.063 g, 0.515 mmol), pyridine (0.069 mL, 0.859 mmol) and activated 4 Å molecular sieves (0.228 g) were added and the resulting mixture was stirred at r.t. in the open air for 24 h. The mixture was diluted with DCM and aqueous concentrated NH$_4$OH was added. The mixture was filtered through a celite pad and the filtrate was evaporated to dryness. The residue was purified by flash chromatography on silica gel Biotage cartridge (cyclohexane to cyclohexane:EtOAc=80:20) to afford title compound as a pale yellow solid (0.092 g, 0.317 mmol, 74% yield). MS/ESI$^+$ 291.2 [MH]$^+$, Rt=1.00 min (Method A).

Intermediate E16: 5-acetyl-2-[2-(morpholin-4-yl)ethyl]-4-phenyl-2,3-dihydropyridazin-3-one

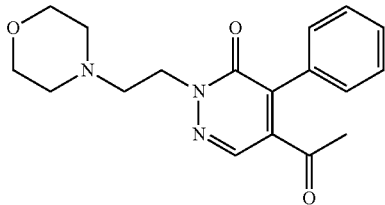 [SMILES: CC(=O)c1cnn(CCN2CCOCC2)c(=O)c1-c1ccccc1]

To a solution of 5-acetyl-4-phenyl-2,3-dihydropyridazin-3-one E11 (0.250 g, 1.17 mmol) in DMF (7.5 mL), potassium carbonate (0.388 g, 2.81 mmol) was added followed by 4-(2-chloroethyl)morpholine hydrochloride (0.260 g, 1.40 mmol) and the resulting mixture was stirred at r.t. for 7 h and then heated to 50° C. overnight. The mixture was partitioned between EtOAc and water and the organic phase was washed several times with brine and dried over sodium sulfate. The solvent was removed and the crude was purified by flash chromatography on silica gel Biotage cartridge (DCM to DCM:MeOH=95:5) to afford title compound as a yellow oil (0.380 g). MS/ESI$^+$ 328.2 [MH]$^+$, Rt=0.40 min (Method A).

Intermediate E17: 5-acetyl-4-phenyl-2-(pyridin-3-yl)-2,3-dihydropyridazin-3-one

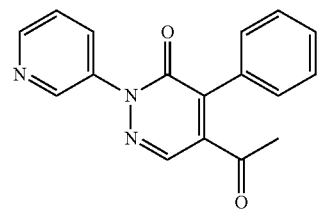 [SMILES: CC(=O)c1cnn(-c2cccnc2)c(=O)c1-c1ccccc1]

To a solution of 5-acetyl-4-phenyl-2,3-dihydropyridazin-3-one E12 (0.150 g, 0.7 mmol) in DCM (9 mL) and DMF (3 mL), copper (II) acetate (0.254 g, 1.4 mmol), 3-pyridinylboronic acid (0.103 g, 0.84 mmol), pyridine (0.11 mL, 1.4 mmol) and activated 4 Å molecular sieves (0.250 g) were added and the resulting mixture was stirred at r.t. in the open air for 4 days. Additional copper (II) acetate (0.150 g, 0.82 mmol) was added, and the reaction was stirred for further 72 h. The mixture was diluted with DCM and 7N NH$_3$ in MeOH was added until the solution turned from green to blue. The mixture was filtered through a celite pad and the filtrate was evaporated to dryness. The residue was purified by flash chromatography on a silica gel Biotage cartridge, (cyclohexane:EtOAc=70:30 to 40:60) to afford title compound as a white solid (0.141 g, 0.48 mmol, 57% yield). MS/ESI$^+$ 292.2 [MH]$^+$, Rt=0.77 min (Method A).

Intermediate E18: 5-acetyl-2-benzyl-4-cyclopentyl-2,3-dihydropyridazin-3-one

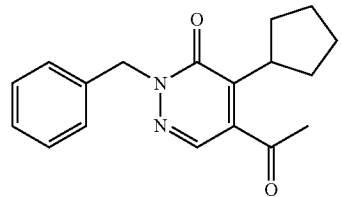 [SMILES: CC(=O)c1cnn(Cc2ccccc2)c(=O)c1C1CCCC1]

Prepared similarly to intermediate E1 starting from 2-benzyl-4-cyclopentyl-5-(1-ethoxyethenyl)-2,3-dihydropyridazin-3-one D9 (0.410 g, 1.26 mmol), stirring for 2 h, to afford title compound as a pale yellow solid (0.361 g, 1.219 mmol, 97% yield). MS/ESI$^+$ 297.2 [MH]$^+$, Rt=1.18 min (Method A).

Intermediate F: ethyl 1-benzyl-6-oxo-1,6-dihydropyridazine-4-carboxylate

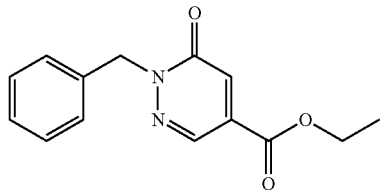 [SMILES: CCOC(=O)c1cnn(Cc2ccccc2)c(=O)c1]

To a solution of ethyl 6-oxo-1,6-dihydropyridazine-4-carboxylate (prepared according to the procedure reported in US2009/111821 A1, which is incorporated herein by reference in its entirety) (0.150 g, 0.89 mmol) in DMF (5 mL), potassium carbonate (0.149 g, 1.07 mmol) was added followed by benzyl bromide (0.127 mL, 1.07 mmol) and the resulting mixture was stirred at r.t. for 2 h. The mixture was diluted with EtOAc and washed with water and then several times with brine. The organic phase was dried over sodium sulfate and the solvent was removed in vacuo. The crude was purified by flash chromatography on silica gel Biotage cartridge (cyclohexane to cyclohexane:EtOAc=80:20) to afford title compound as a white solid (0.201 g, 0.778 mmol, 87% yield). MS/ESI$^+$ 259.1 [MH]$^+$, Rt=0.98 min (Method A).

Intermediate G1: 2-benzyl-5-(1-hydroxyethyl)-6-phenyl-2,3-dihydropyridazin-3-one

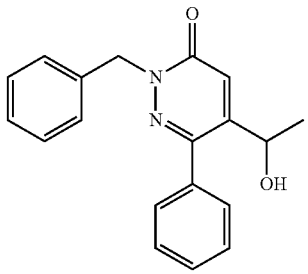 [SMILES: CC(O)c1cc(=O)n(Cc2ccccc2)nc1-c1ccccc1]

To a solution of 5-acetyl-2-benzyl-6-phenyl-2,3-dihydropyridazin-3-one E1 (1.066 g, 3.50 mmol) in THF (5 mL) and MeOH (5 mL), NaBH$_4$ (0.199 g, 5.25 mmol) was added and the resulting mixture was stirred at r.t. for 2 h. Water was added and the mixture was extracted with DCM; the organic layer was dried over sodium sulfate and the solvent was evaporated. The crude was dissolved in CH$_3$CN (30 mL), CuCl$_2$ (0.961 g, 7.14 mmol) was added and the reaction was refluxed overnight. The mixture was then poured into ice and extracted with DCM; the organic phase was dried over sodium sulfate and the solvent evaporated. The crude was purified by flash chromatography on a silica gel Biotage SNAP cartridge (cyclohexane:EtOAc=1:1) to afford title compound (0.525 g, 1.71 mmol, 49% yield). MS/ESI$^+$ 307.2 [MH]$^+$, RT=0.97 min (Method A).

Intermediate G2: 5-(1-hydroxyethyl)-2-methyl-6-phenyl-2,3-dihydropyridazin-3-one

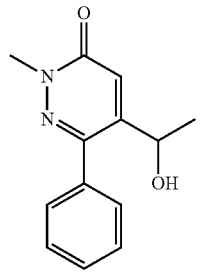 [SMILES: CC(O)c1cc(=O)n(C)nc1-c1ccccc1]

Prepared similarly to intermediate G1 starting from 5-acetyl-2-methyl-6-phenyl-2,3-dihydropyridazin-3-one E2 (0.204 g, 0.894 mmol) in THF (4 mL) and MeOH (1 mL) and purified by flash chromatography on silica gel Biotage SNAP cartridge (DCM to DCM:MeOH=98:2) to afford title compound (0.105 g, 0.456 mmol, 51% yield). MS/ESI$^+$ 231.1 [MH]$^+$, RT=0.69 min (Method A).

Intermediate G3: 5-(1-hydroxyethyl)-6-phenyl-2-(propan-2-yl)-2,3-dihydropyridazin-3-one

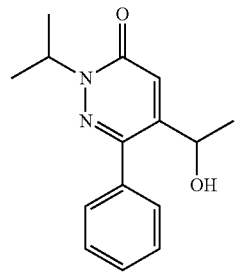 [SMILES: CC(O)c1cc(=O)n(C(C)C)nc1-c1ccccc1]

Prepared similarly to intermediate G1 starting from 5-acetyl-6-phenyl-2-(propan-2-yl)-2,3-dihydropyridazin-3-one E3 (0.440 g, 1.718 mmol) in THF (5 mL) and MeOH (1 mL), and purified by flash chromatography on Biotage silica NH cartridge (cyclohexane:EtOAc=80:20 to 100% EtOAc) to afford title compound as a white solid (0.132 g, 0.511 mmol, 30% yield). MS/ESI$^+$ 259.0 [MH]$^+$, RT=0.86 min (Method A).

Intermediate G4: 2-(cyclopropylmethyl)-5-(1-hydroxyethyl)-6-phenyl-2,3-dihydropyridazin-3-one

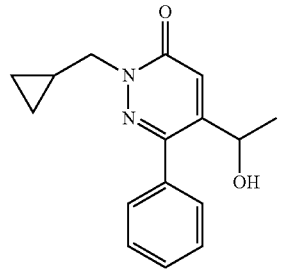 [SMILES: CC(O)c1cc(=O)n(CC2CC2)nc1-c1ccccc1]

Prepared similarly to intermediate 01 starting from 5-acetyl-2-(cyclopropylmethyl)-6-phenyl-2,3-dihydropyridazin-3-one E5 (0.212 g, 0.79 mmol) in THF (4 mL) and MeOH (1 mL), and purified by flash chromatography on silica gel Biotage cartridge (DCM to DCM:MeOH=98:2) to afford title compound (0.178 g). MS/ESI$^+$ 271.2 [MH]$^+$, RT=0.88 min (Method A).

Intermediate G5: 5-(1-hydroxyethyl)-2,6-diphenyl-2,3-dihydropyridazin-3-one

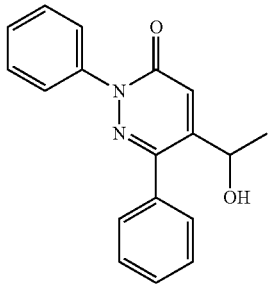 [SMILES: CC(O)c1cc(=O)n(-c2ccccc2)nc1-c1ccccc1]

Prepared similarly to intermediate G1 starting from 5-acetyl-2,6-diphenyl-2,3-dihydropyridazin-3-one E6 (0.370 g, 1.275 mmol) in THF (8 mL) and MeOH (2 mL), and purified by flash chromatography on silica gel Biotage cartridge (DCM to DCM:MeOH=98:2) to afford title compound (0.097 g, 0.33 mmol, 26% yield). MS/ESI$^+$ 293.2 [MH]$^+$, RT=0.90 min (Method A).

Intermediate G6: 5-(1-hydroxyethyl)-6-phenyl-2-(pyridin-2-ylmethyl)-2,3-dihydropyridazin-3-one

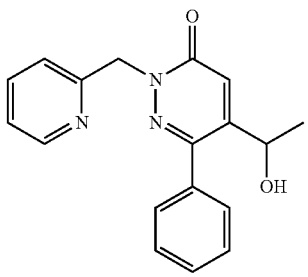 [SMILES: CC(O)c1cc(=O)n(Cc2ccccn2)nc1-c1ccccc1]

To a solution of 5-acetyl-6-phenyl-2-(pyridin-2-ylmethyl)-2,3-dihydropyridazin-3-one E7 (0.268 g, 0.878 mmol) in THF (4 mL) and MeOH (1 mL), NaBH$_4$ (0.050 g, 1.32 mmol) was added and the resulting mixture was stirred at r.t. for 2 h. Water was added and the mixture was extracted with DCM; the organic phase was dried over sodium sulfate and the solvent evaporated. The crude was suspended in aqueous 0.5M NaOH (15 mL), sodium 3-nitrobenzenesulfonate (0.190 g, 0.855 mmol) was added and the resulting mixture was refluxed for 1 h. The mixture was neutralized with aqueous 6M HCl and extracted with DCM. The combined organic layers were washed with brine and dried over sodium sulfate; the solvent was removed and the crude was purified by flash chromatography on silica gel Biotage cartridge (cyclohexane:AcOEt=90:10 to 60:40) to afford title compound (0.041 g, 0.133 mmol, 16% yield). MS/ESI$^+$ 308.2 [MH]$^+$, RT=0.67 min (Method A).

Intermediate G7: 2-benzyl-5-(1-hydroxyethyl)-2,3-dihydropyridazin-3-one

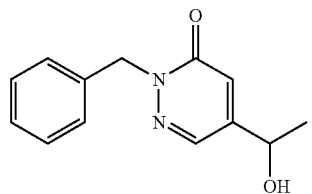 [SMILES: CC(O)c1cnn(Cc2ccccc2)c(=O)c1]

To a solution of 5-acetyl-2-benzyl-2,3-dihydropyridazin-3-one E8 (0.288 g, 1.26 mmol) in THF (5 mL) and MeOH (0.5 mL) cooled at 0° C., NaBH$_4$ (0.062 g, 1.64 mmol) was added and the resulting mixture was left to warm to r.t. stirring for 2 h. The mixture was quenched by addition of aqueous 1N HCl, the volatiles were removed in vacuo and the residue was suspended in DCM/MeOH 1:1. The insoluble materials were filtered off and solvent was removed to afford title compound (0.140 g). MS/ESI$^+$ 231.0 [MH]$^+$, RT=0.69 min (Method A).

Intermediate G8: 5-(1-hydroxyethyl)-2-phenyl-2,3-dihydropyridazin-3-one

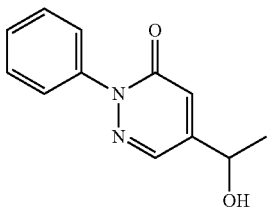 [SMILES: CC(O)c1cnn(-c2ccccc2)c(=O)c1]

Prepared similarly to intermediate G7 starting from 5-acetyl-2-phenyl-2,3-dihydropyridazin-3-one E9 (0.262 g, 1.22 mmol) and further purified by flash chromatography on Biotage silica cartridge (toluene:AcOEt=90:10 to 100% EtOAc) to afford title compound (0.080 g, 0.37 mmol, 30% yield). MS/ESI$^+$ 216.9 [MH]$^+$, RT=0.59 min (Method A).

Intermediate G9: 5-(1-hydroxyethyl)-2-methyl-2,3-dihydropyridazin-3-one

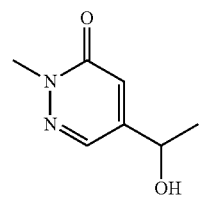

Prepared similarly to intermediate G1 starting from 5-acetyl-2-methyl-2,3-dihydropyridazin-3-one E10 (0.544 g, 3.57 mmol) in THF (8 mL) and MeOH (2 mL), and purified by flash chromatography on silica gel Biotage SNAP cartridge (DCM to DCM:MeOH=98:2) to afford title compound (0.220 g, 1.428 mmol, 40% yield). MS/ESI$^+$ 155.1 [MH]$^+$, RT=0.37 min (Method A).

Intermediate G10: 2-tert-butyl-5-(1-hydroxyethyl)-4-phenyl-2,3-dihydropyridazin-3-one

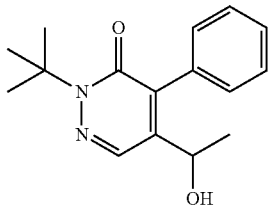 [SMILES: CC(O)c1cnn(C(C)(C)C)c(=O)c1-c1ccccc1]

To a solution of 5-acetyl-2-tert-butyl-4-phenyl-2,3-dihydropyridazin-3-one E11 (0.200 g, 0.740 mmol) in THF (5 mL) and MeOH (0.5 mL) cooled at 0° C., NaBH$_4$ (0.036 g, 0.962 mmol) was added and the resulting mixture was left to warm to r.t. stirring for 2 h. The mixture was partitioned between DCM and water and the aqueous phase was extracted with DCM. The combined organic layers were washed with brine and dried over sodium sulfate. The solvent was removed to afford title compound as a pale yellow solid (0.190 g, 0.698 mmol, 94% yield). MS/ESI$^+$ 273.0 [MH]$^+$, RT=0.93 min (Method A).

Intermediate G11: 2-benzyl-5-(1-hydroxyethyl)-4-phenyl-2,3-dihydropyridazin-3-one

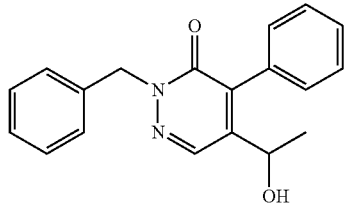 [SMILES: CC(O)c1cnn(Cc2ccccc2)c(=O)c1-c1ccccc1]

Prepared similarly to intermediate G10 starting from 5-acetyl-2-benzyl-4-phenyl-2,3-dihydropyridazin-3-one E13 (0.103 g, 0.338 mmol), stirring for 1 h, to afford title compound as a white solid (0.090 g, 0.294 mmol, 87% yield). MS/ESI$^+$ 307.3 [MH]$^+$, RT=0.93 min (Method A).

Intermediate G12: 5-(1-hydroxyethyl)-2-methyl-4-phenyl-2,3-dihydropyridazin-3-one

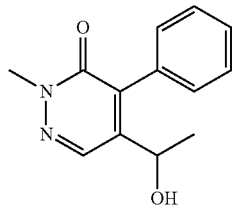 [SMILES: CC(O)c1cnn(C)c(=O)c1-c1ccccc1]

Prepared similarly to intermediate G10 starting from 5-acetyl-2-methyl-4-phenyl-2,3-dihydropyridazin-3-one E14 (0.073 g, 0.320 mmol), stirring for 1 h, to afford title compound as colorless amorphous (0.066 g, 0.287 mmol, 89% yield). MS/ESI$^+$ 231.1 [MH]$^+$, RT=0.61 min (Method A).

Intermediate G13: 5-(1-hydroxyethyl)-2,4-diphenyl-2,3-dihydropyridazin-3-one

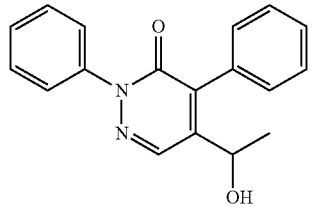 [SMILES: CC(O)c1cnn(-c2ccccc2)c(=O)c1-c1ccccc1]

Prepared similarly to intermediate G10 starting from 5-acetyl-2,4-diphenyl-2,3-dihydropyridazin-3-one E15 (0.090 g, 0.310 mmol), stirring for 1 h, to afford title compound as white solid (0.089 g, 0.304 mmol, 98% yield). MS/ESI$^+$ 293.2 [MH]$^+$, RT=0.85 min (Method A).

Intermediate G14: 5-(1-hydroxyethyl)-2-[2-(morpholin-4-yl)ethyl]-4-phenyl-2,3-dihydropyridazin-3-one

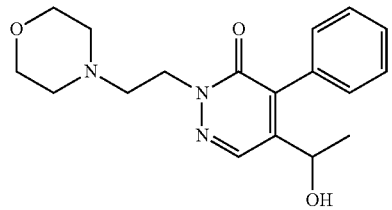 [SMILES: CC(O)c1cnn(CCN2CCOCC2)c(=O)c1-c1ccccc1]

Prepared similarly to intermediate G10 starting from 5-acetyl-2-[2-(morpholin-4-yl)ethyl]-4-phenyl-2,3-dihydropyridazin-3-one E16 (0.380 g) stirring for 1 h, to afford title compound as a yellow oil (0.372 g). MS/ESI$^+$ 330.3 [MH]$^+$, RT=0.36 min (Method A).

Intermediate G15: 5-(1-hydroxyethyl)-4-phenyl-2-(pyridin-3-yl)-2,3-dihydropyridazin-3-one

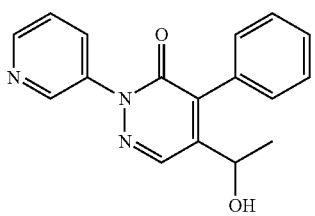 [SMILES: CC(O)c1cnn(-c2cccnc2)c(=O)c1-c1ccccc1]

Prepared similarly to intermediate G10 starting from 5-acetyl-4-phenyl-2-(pyridin-3-yl)-2,3-dihydropyridazin-3-one E17 (0.141 g, 0.45 mmol), stirring for 30 min, to afford title compound as white solid (0.121 g). MS/ESI$^+$ 294.3 [MH]$^+$, RT=0.64 min (Method A).

Intermediate G16: 2-benzyl-4-cyclopentyl-5-(1-hydroxyethyl)-2,3-dihydropyridazin-3-one

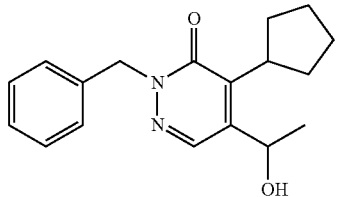 [SMILES: CC(O)c1cnn(Cc2ccccc2)c(=O)c1C1CCCC1]

Prepared similarly to intermediate G10 starting from 5-acetyl-2-benzyl-4-cyclopentyl-2,3-dihydropyridazin-3-one E18 (0.361 g, 1.219 mmol), stirring for 1 h, to afford title compound (0.358 g, 1.201 mmol, 98% yield). MS/ESI⁺ 299.2 [MH]⁺, RT=1.06 min (Method A).

Intermediate G17: 2-benzyl-5-(hydroxymethyl)-2,3-dihydropyridazin-3-one

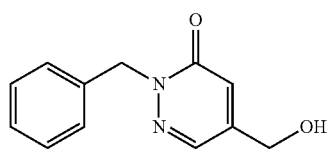 [SMILES: O=c1cc(CO)cnn1Cc1ccccc1]

CaCl$_2$ (0.173 g, 1.55 mmol) was added portion-wise to a stirred cooled mixture of ethyl 1-benzyl-6-oxo-1,6-dihydropyridazine-4-carboxylate F (0.201 g, 0.77 mmol) and NaBH$_4$ (0.118 g, 3.11 mmol) in THF (5 mL) and MeOH (5 mL), keeping the temperature around 30° C. After stirring at r.t. for 2 h the mixture was quenched with aqueous 1N HCl and extracted with EtOAc; the organic phase was dried over sodium sulfate and the solvent was removed in vacuo. The crude was dissolved in CH$_3$CN (10 mL), CuCl$_2$ (0.247 g, 1.83 mmol) was added and the resulting mixture was refluxed overnight. The mixture was poured into ice and extracted with DCM; the organic phase was dried over sodium sulfate and the solvent evaporated. The crude was purified by flash chromatography on silica gel Biotage cartridge (cyclohexane:EtOAc=1:1) to afford title compound (0.030 g, 0.138 mmol, 18% yield). MS/ESI⁺ 217.1 [MH]⁺, RT=0.66 min (Method A).

Intermediate H1: 5-(1-azidoethyl)-2-benzyl-6-phenyl-2,3-dihydropyridazin-3-one

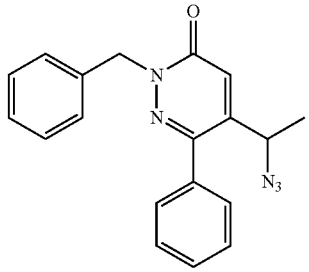 [SMILES: CC(N=[N+]=[N-])c1cc(=O)n(Cc2ccccc2)nc1-c1ccccc1]

DPPA (0.281 mL, 1.305 mmol), followed by DBU (0.195 mL, 1.305 mmol) were added to a solution of 2-benzyl-5-(1-hydroxyethyl)-6-phenyl-2,3-dihydropyridazin-3-one G1 (0.200 g, 0.652 mmol) in THF (10 mL) under nitrogen, and the mixture was stirred at r.t. overnight. The solvent was removed under vacuum and the residue was partitioned between EtOAc and water. The aqueous phase was extracted with EtOAc and the combined organic layers were washed with brine and dried over sodium sulfate. The solvent was removed and the crude was purified by flash chromatography on silica gel Biotage SNAP cartridge (cyclohexane:EtOAc=90:10 to 60:40) to afford title compound (0.130 g, 0.39 mmol, 60% yield). MS/ESI⁺ 333.2 [MH]⁺, RT=1.18 min (Method A).

Intermediate H2: 5-(1-azidoethyl)-2-methyl-6-phenyl-2,3-dihydropyridazin-3-one

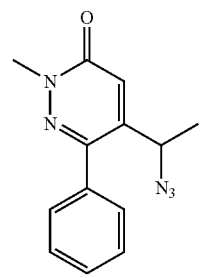 [SMILES: CC(N=[N+]=[N-])c1cc(=O)n(C)nc1-c1ccccc1]

Prepared similarly to intermediate H1, starting from 5-(1-hydroxyethyl)-2-methyl-6-phenyl-2,3-dihydropyridazin-3-one G2 (0.040 g, 0.17 mmol), and purified by flash chromatography on silica gel Biotage cartridge (cyclohexane:EtOAc=90:10 to 60:40) to afford title compound (0.036 g, 0.141 mmol, 83% yield). MS/ESI⁺ 256.1 [MH]⁺, RT=0.93 min (Method A).

Intermediate H3: 5-(1-azidoethyl)-6-phenyl-2-(propan-2-yl)-2,3-dihydropyridazin-3-one

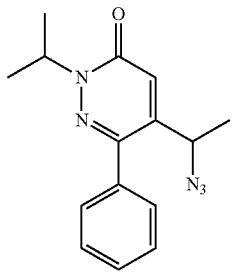 [SMILES: CC(N=[N+]=[N-])c1cc(=O)n(C(C)C)nc1-c1ccccc1]

Prepared similarly to intermediate H1, starting from 5-(1-hydroxyethyl)-6-phenyl-2-(propan-2-yl)-2,3-dihydropyridazin-3-one G3 (0.060 g, 0.232 mmol); after stirring at r.t. overnight additional DPPA (2 eq) and DBU (2 eq) were added and the mixture was stirred at r.t. for further 24 h. The crude was purified by flash chromatography on silica gel Biotage cartridge (cyclohexane to cyclohexane:EtOAc=80:20) to afford title compound as a colorless oil (0.038 g, 0.134 mmol, 58% yield). MS/ESI⁺ 284.2 [MH]⁺, RT=1.11 min (Method A).

Intermediate H4: 5-(1-azidoethyl)-2-(cyclopropylmethyl)-6-phenyl-2,3-dihydropyridazin-3-one

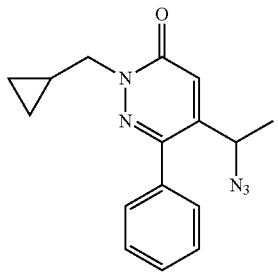 [SMILES: CC(N=[N+]=[N-])c1cc(=O)n(CC2CC2)nc1-c1ccccc1]

Prepared similarly to intermediate H1, starting from 2-(cyclopropylmethyl)-5-(1-hydroxyethyl)-6-phenyl-2,3-dihydropyridazin-3-one G4 (0.092 g) and purified by flash chromatography on silica gel Biotage cartridge (cyclohexane:AcOEt=90:10 to 60:40) to afford title compound (0.061 g, 0.206 mmol). MS/ESI$^+$ 296.2 [MH]$^+$, RT=1.12 min (Method A).

Intermediate H5: 5-(1-azidoethyl)-2,6-diphenyl-2,3-dihydropyridazin-3-one

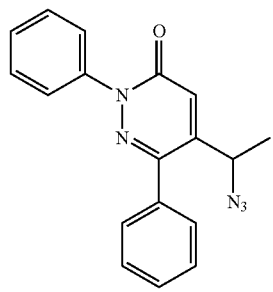 [SMILES: CC(N=[N+]=[N-])c1cc(=O)n(-c2ccccc2)nc1-c1ccccc1]

Prepared similarly to intermediate H1, starting from 5-(1-hydroxyethyl)-2,6-diphenyl-2,3-dihydropyridazin-3-one G5 (0.047 g, 0.16 mmol) and purified by flash chromatography on silica gel Biotage cartridge (cyclohexane:AcOEt=90:10 to 60:40) to afford title compound (0.028 g, 0.088 mmol, 55% yield). MS/ESI$^+$ 318.2 [MH]$^+$, RT=1.13 min (Method A).

Intermediate I1: 5-(1-aminoethyl)-2-benzyl-6-phenyl-2,3-dihydropyridazin-3-one

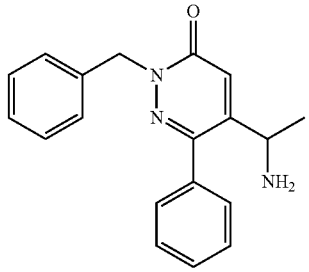 [SMILES: CC(N)c1cc(=O)n(Cc2ccccc2)nc1-c1ccccc1]

PPh$_3$ (0.206 g, 0.78 mmol) was added to a solution of 5-(1-azidoethyl)-2-benzyl-6-phenyl-2,3-dihydropyridazin-3-one H1 (0.130 g, 0.39 mmol) in THF (5 mL) under nitrogen, and the mixture was stirred at r.t. overnight. Water (1 mL) was added and the reaction was heated at 60° C. for 4 h. The solvent was removed under vacuum and the residue was dissolved in MeOH and charged on a SCX cartridge (2 g), washing with MeOH. The product was eluted with 2 M NH$_3$ in MeOH and the volatiles were removed under reduced pressure to afford title compound as brown oil which was used without any further purification (0.112 g, 0.366 mmol, 94% yield). MS/ESI$^+$ 306.2 [MH]$^+$, Rt=0.61 min (Method A).

Intermediate I2: 5-(1-aminoethyl)-2-methyl-6-phenyl-2,3-dihydropyridazin-3-one

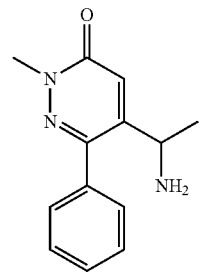 [SMILES: CC(N)c1cc(=O)n(C)nc1-c1ccccc1]

Prepared similarly to intermediate I1 starting from 5-(1-azidoethyl)-2-methyl-6-phenyl-2,3-dihydropyridazin-3-one H2 (0.036 g, 0.141 mmol) to afford title compound as brown oil which was used without any further purification (0.0324 g, 0.141 mmol, quantitative yield). MS/ESI$^+$ 230.2 [MH]$^+$, Rt=0.37 min (Method A).

Intermediate I3: 5-(1-aminoethyl)-6-phenyl-2-(propan-2-yl)-2,3-dihydropyridazin-3-one

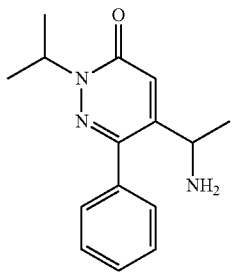 [SMILES: CC(N)c1cc(=O)n(C(C)C)nc1-c1ccccc1]

Prepared similarly to intermediate I1 starting from 5-(1-azidoethyl)-6-phenyl-2-(propan-2-yl)-2,3-dihydropyridazin-3-one H3 (0.038 g, 0.134 mmol), heating at 50° C. for 4 h after addition of water, to afford title compound as colorless amorphous which was used without any further purification (0.031 g, 0.120 mmol, 90% yield). MS/ESI$^+$ 258.2 [MH]$^+$, Rt=0.52 min (Method A).

Intermediate I4: 5-(1-aminoethyl)-2-(cyclopropylmethyl)-6-phenyl-2,3-dihydropyridazin-3-one

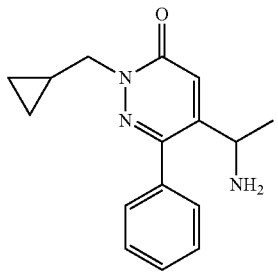 [SMILES: CC(N)c1cc(=O)n(CC2CC2)nc1-c1ccccc1]

Prepared similarly to intermediate I1 starting from 5-(1-azidoethyl)-2-(cyclopropylmethyl)-6-phenyl-2,3-dihydropyridazin-3-one H4 (0.061 g, 0.206 mmol), heating at 60° C. overnight after addition of water, to afford title compound as brown oil which was used without any further purification (0.043 g). MS/ESI⁺ 270.2 [MH]⁺, Rt=0.53 min (Method A).

Intermediate I5: 5-(1-aminoethyl)-2,6-diphenyl-2,3-dihydropyridazin-3-one

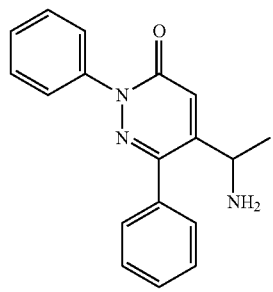 [SMILES: CC(N)c1cc(=O)n(-c2ccccc2)nc1-c1ccccc1]

Prepared similarly to intermediate I1 starting from 5-(1-azidoethyl)-2,6-diphenyl-2,3-dihydropyridazin-3-one H5 (0.028 g, 0.088 mmol) to afford title compound as brown oil which was used without any further purification (0.023 g). MS/ESI⁺ 292.2 [MH]⁺, Rt=0.55 min (Method A).

Intermediate and compound J1: 5-(1-{4-amino-3-iodo-1H-pyrazolo[3,4-d]pyrimidin-1-yl}ethyl)-2-benzyl-6-phenyl-2,3-dihydropyridazin-3-one

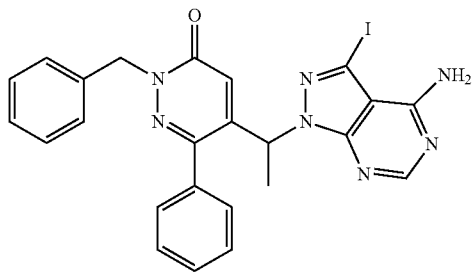 [SMILES: CC(c1cc(=O)n(Cc2ccccc2)nc1-c1ccccc1)n1nc(I)c2c(N)ncnc21]

To a mixture of 2-benzyl-5-(1-hydroxyethyl)-6-phenyl-2,3-dihydropyridazin-3-one G1 (0.100 g, 0.326 mmol), 3-iodo-1H-pyrazolo[3,4-d]pyrimidin-4-amine (0.111 g, 0.424 mmol) and PPh₃ (0.128 g, 0.489 mmol) in dry THF (9 mL), a solution of DIAD (0.083 mL, 0.424 mmol) in THF (1 mL) was added drop-wise at r.t. and the reaction was stirred for 3 h. The solvent was removed and the residue was purified by flash chromatography on Biotage silica gel cartridge (DCM to DCM:MeOH=98:2) to afford title compound (0.146 g, 0.265 mmol, 81% yield). MS/ESI⁺ 550.2 [MH]⁺, Rt 0.97 min (Method A).

Intermediate and compound J2: 5-(1-{4-amino-3-iodo-1H-pyrazolo[3,4-d]pyrimidin-1-yl}ethyl)-2-methyl-6-phenyl-2,3-dihydropyridazin-3-one

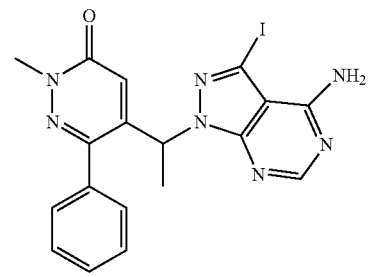 [SMILES: CC(c1cc(=O)n(C)nc1-c1ccccc1)n1nc(I)c2c(N)ncnc21]

Prepared similarly to intermediate J1 starting from 5-(1-hydroxyethyl)-2-methyl-6-phenyl-2,3-dihydropyridazin-3-one G2 (0.065 g, 0.26 mmol), stirring for 2 h, and purified by flash chromatography on Biotage silica gel cartridge (DCM to DCM:MeOH=98:2) to afford title compound (0.102 g). MS/ESI⁺ 474.2 [MH]⁺, Rt 0.71 min (Method A).

Intermediate and compound J3: 5-(1-{4-amino-3-iodo-1H-pyrazolo[3,4-d]pyrimidin-1-yl}ethyl)-6-phenyl-2-(propan-2-yl)-2,3-dihydropyridazin-3-one

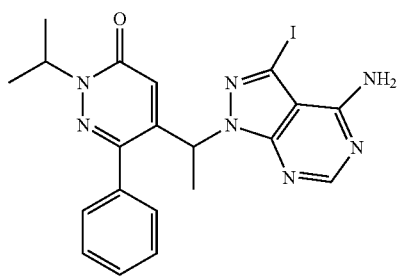 [SMILES: CC(C)n1nc(-c2ccccc2)c(C(C)n2nc(I)c3c(N)ncnc32)cc1=O]

Prepared similarly to intermediate J1 starting from 5-(1-hydroxyethyl)-6-phenyl-2-(propan-2-yl)-2,3-dihydropyridazin-3-one G3 (0.070 g, 0.271 mmol), stirring for 2 h, and purified by flash chromatography on Biotage silica-NH cartridge (DCM to DCM:EtOAc=85:15) to afford title compound as a white solid (0.101 g). MS/ESI⁺ 502.2 [MH]⁺, Rt 0.87 min (Method A).

Intermediate and compound J4: 5-(1-{4-amino-3-iodo-1H-pyrazolo[3,4-d]pyrimidin-1-yl}ethyl)-2-(cyclopropylmethyl)-6-phenyl-2,3-dihydropyridazin-3-one

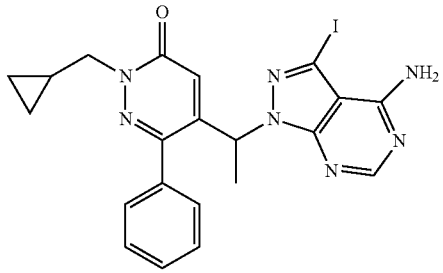 [SMILES: CC(c1cc(=O)n(CC2CC2)nc1-c1ccccc1)n1nc(I)c2c(N)ncnc21]

Prepared similarly to intermediate J1 starting from 2-(cyclopropylmethyl)-5-(1-hydroxyethyl)-6-phenyl-2,3-dihydropyridazin-3-one G4 (0.086 g), stirring for 2 h, and purified by flash chromatography on Biotage silica gel cartridge (DCM to DCM:MeOH=98:2) to afford title compound (0.105 g). MS/ESI⁺ 514.2 [MH]⁺, Rt 0.89 min (Method A).

Intermediate and compound J5: 5-(1-{4-amino-3-iodo-1H-pyrazolo[3,4-d]pyrimidin-1-yl}ethyl)-2,6-diphenyl-2,3-dihydropyridazin-3-one

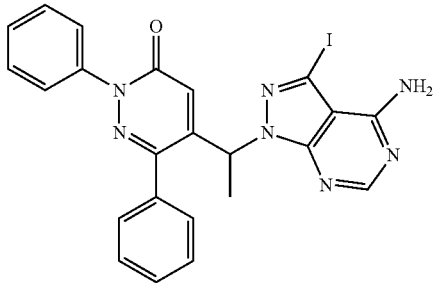 [SMILES: CC(c1cc(=O)n(-c2ccccc2)nc1-c1ccccc1)n1nc(I)c2c(N)ncnc21]

Prepared similarly to intermediate J1 starting from 5-(1-hydroxyethyl)-2,6-diphenyl-2,3-dihydropyridazin-3-one G5 (0.050 g, 0.17 mmol), stirring for 2 h, and purified by flash chromatography on Biotage silica gel cartridge (DCM to DCM:MeOH=98:2) followed by filtration through SCX cartridge (1 g), washing with MeOH and then eluting with 2M NH₃ in MeOH to afford title compound (0.033 g). MS/ESI⁺ 536.2 [MH]⁺, Rt 0.91 min (Method A).

Intermediate and compound J6: 5-(1-{4-amino-3-iodo-1H-pyrazolo[3,4-d]pyrimidin-1-yl}ethyl)-6-phenyl-2-(pyridin-2-ylmethyl)-2,3-dihydropyridazin-3-one

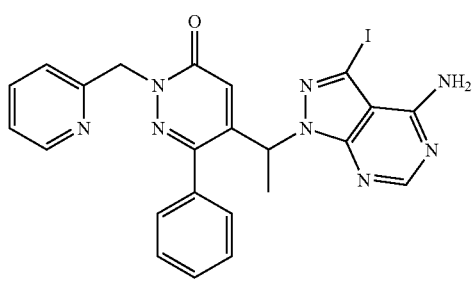 [SMILES: CC(c1cc(=O)n(Cc2ccccn2)nc1-c1ccccc1)n1nc(I)c2c(N)ncnc21]

Prepared similarly to intermediate J1 starting from 5-(1-hydroxyethyl)-6-phenyl-2-(pyridin-2-ylmethyl)-2,3-dihydropyridazin-3-one G6 (0.041 g, 0.133 mmol), stirring for 2 h, and purified by flash chromatography on Biotage silica gel cartridge (DCM to DCM:MeOH=98:2) to afford title compound, (0.031 g). MS/ESI⁺ 551.1 [MH]⁺, Rt 0.70 min (Method A).

Intermediate and compound J7: 5-(1-{4-amino-3-iodo-1H-pyrazolo[3,4-d]pyrimidin-1-yl}ethyl)-2-benzyl-2,3-dihydropyridazin-3-one

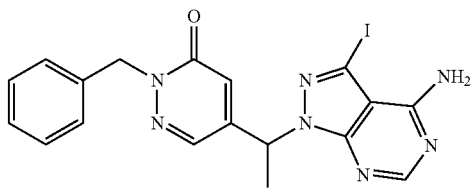 [SMILES: CC(c1cnn(Cc2ccccc2)c(=O)c1)n1nc(I)c2c(N)ncnc21]

Prepared similarly to intermediate J1 starting from 2-benzyl-5-(1-hydroxyethyl)-2,3-dihydropyridazin-3-one G7 (0.140 g), stirring for 2 h, and purified by flash chromatography on Biotage silica gel cartridge (DCM to DCM:MeOH=98:2) to afford title compound (0.287 g, 0.607 mmol). MS/ESI⁺ 474.0 [MH]⁺, Rt 0.84 min (Method A).

Intermediate and compound J8: 5-(1-{4-amino-3-iodo-1H-pyrazolo[3,4-d]pyrimidin-1-yl}ethyl)-2-phenyl-2,3-dihydropyridazin-3-one

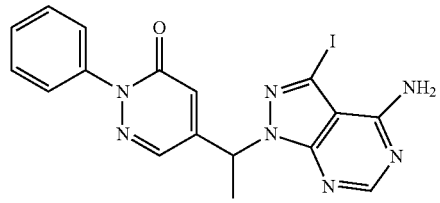 [SMILES: CC(c1cnn(-c2ccccc2)c(=O)c1)n1nc(I)c2c(N)ncnc21]

Prepared similarly to intermediate J1 starting from 5-(1-hydroxyethyl)-2-phenyl-2,3-dihydropyridazin-3-one G8 (0.080 g, 0.37 mmol), stirring for 2 h, and purified by flash chromatography on Biotage silica gel cartridge (DCM to DCM:MeOH=98:2) to afford title compound (0.170 g). MS/ESI⁺ 460.2 [MH]⁺, Rt 0.79 min (Method A).

Intermediate and compound J9: 5-(1-{4-amino-3-iodo-1H-pyrazolo[3,4-d]pyrimidin-1-yl}ethyl)-2-methyl-2,3-dihydropyridazin-3-one

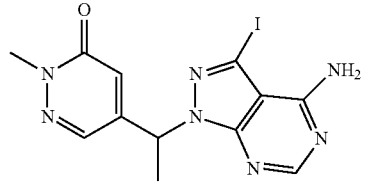 [SMILES: CC(c1cnn(C)c(=O)c1)n1nc(I)c2c(N)ncnc21]

Prepared similarly to intermediate J1 starting from 5-(1-hydroxyethyl)-2-methyl-2,3-dihydropyridazin-3-one G9 (0.100 g, 0.649 mmol), stirring for 2 h, and purified by flash chromatography on Biotage silica gel cartridge (DCM to DCM:MeOH=98:2) to afford title compound (0.115 g). MS/ESI⁺ 398.1 [MH]⁺, Rt 0.58 min (Method A).

Intermediate and compound J10: 5-(1-{4-amino-3-iodo-1H-pyrazolo[3,4-d]pyrimidin-1-yl}ethyl)-2-tert-butyl-4-phenyl-2,3-dihydropyridazin-3-one

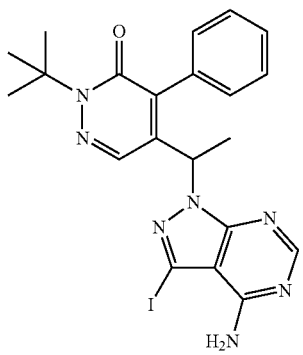 [SMILES: CC(c1cnn(C(C)(C)C)c(=O)c1-c1ccccc1)n1nc(I)c2c(N)ncnc21]

Prepared similarly to intermediate J1 starting from 2-tert-butyl-5-(1-hydroxyethyl)-4-phenyl-2,3-dihydropyridazin-3-one G10 (0.100 g, 0.367 mmol), stirring overnight, and purified by flash chromatography on Biotage silica-NH cartridge (DCM:MeOH=99:1 to 90:10) to afford title compound (0.135 g). MS/ESI⁺ 516.3 [MH]⁺, Rt 1.11 min (Method A).

Intermediate and compound J11: 5-(1-{4-amino-3-iodo-1H-pyrazolo[3,4-d]pyrimidin-1-yl}ethyl)-2-benzyl-4-phenyl-2,3-dihydropyridazin-3-one

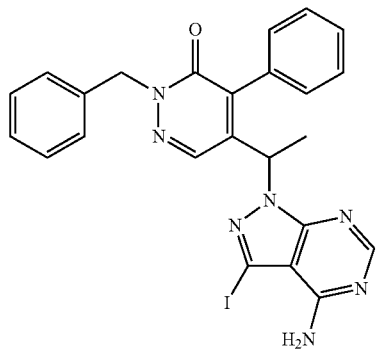 [SMILES: CC(c1cnn(Cc2ccccc2)c(=O)c1-c1ccccc1)n1nc(I)c2c(N)ncnc21]

Prepared similarly to intermediate J1 starting from 2-benzyl-5-(1-hydroxyethyl)-4-phenyl-2,3-dihydropyridazin-3-one G11 (0.088 g, 0.287 mmol), stirring overnight, and purified by flash chromatography on Biotage silica-NH cartridge (DCM to DCM:EtOAc=90:10). A further purification by flash chromatography on Biotage silica-NH cartridge (cyclohexane:EtOAc=90:10 to 50:50) was required to afford title compound as a colorless amorphous (0.095 g). MS/ESI⁺ 550.2 [MH]⁺, Rt 1.06 min (Method A).

Intermediate and compound J12: 5-(1-{4-amino-3-iodo-1H-pyrazolo[3,4-d]pyrimidin-1-yl}ethyl)-2-methyl-4-phenyl-2,3-dihydropyridazin-3-one

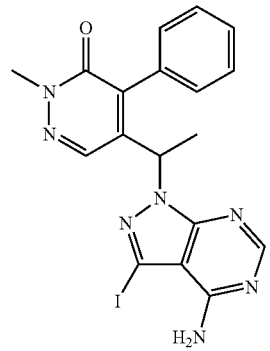 [SMILES: CC(c1cnn(C)c(=O)c1-c1ccccc1)n1nc(I)c2c(N)ncnc21]

Prepared similarly to intermediate J1 starting from 5-(1-hydroxyethyl)-2-methyl-4-phenyl-2,3-dihydropyridazin-3-one G12 (0.065 g, 0.282 mmol), stirring for 2 h; additional PPh₃ (0.3 eq.) was added followed by DIAD (0.3 eq.), and the reaction was stirred at r.t. for further 2 h. The crude was purified by flash chromatography on Biotage silica-NH cartridge (DCM to DCM:EtOAc=90:10) followed by filtration through SCX cartridge (5 g), washing with MeOH and then eluting with 1M NH₃ in MeOH to afford title compound as a white solid (0.070 g, 0.148 mmol, 52% yield). MS/ESI⁺ 474.2 [MH]⁺, Rt 0.77 min (Method A).

Intermediate and compound J13: 5-(1-{4-amino-3-iodo-1H-pyrazolo[3,4-d]pyrimidin-1-yl}ethyl)-2,4-diphenyl-2,3-dihydropyridazin-3-one

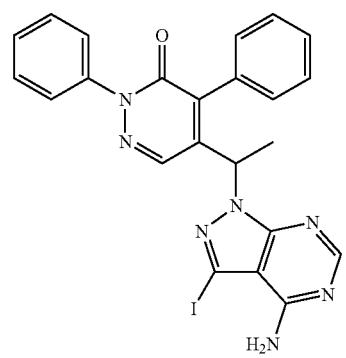 [SMILES: CC(c1cnn(-c2ccccc2)c(=O)c1-c1ccccc1)n1nc(I)c2c(N)ncnc21]

Prepared similarly to intermediate J1 starting from 5-(1-hydroxyethyl)-2,4-diphenyl-2,3-dihydropyridazin-3-one G13 (0.087 g, 0.298 mmol), stirring for 2 h and purified by flash chromatography on Biotage silica-NH cartridge (DCM to DCM:EtOAc=90:10) followed by filtration through SCX cartridge (2 g), washing with MeOH and then eluting with 1M NH₃ in MeOH. A further purification by flash chromatography on Biotage silica-NH cartridge (cyclohexane:EtOAc=80:20 to 40:60) was required to afford title compound as a white solid (0.080 g, 0.149 mmol, 50% yield). MS/ESI⁺ 536.2 [MH]⁺, Rt 1.00 min (Method A).

Intermediate and compound J14: 5-(1-{4-amino-3-iodo-1H-pyrazolo[3,4-d]pyrimidin-1-yl}ethyl)-2-[2-(morpholin-4-yl)ethyl]-4-phenyl-2,3-dihydropyridazin-3-one

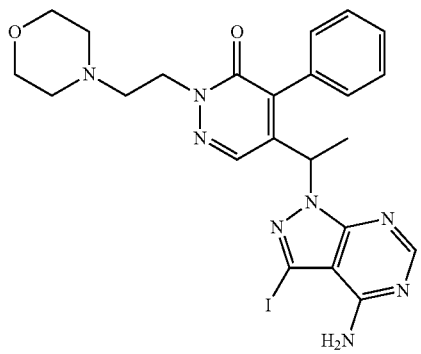 [SMILES: CC(c1cnn(CCN2CCOCC2)c(=O)c1-c1ccccc1)n1nc(I)c2c(N)ncnc21]

Prepared similarly to intermediate J1 starting from 5-(1-hydroxyethyl)-2-[2-(morpholin-4-yl)ethyl]-4-phenyl-2,3-dihydropyridazin-3-one G14 (0.372 g), stirring overnight and purified by flash chromatography on Biotage silica-NH cartridge (DCM to DCM:MeOH=95:5) to afford title compound as a yellow oil (0.114 g). MS/ESI+ 573.2 [MH]+, Rt 0.49 min (Method A).

Intermediate and compound J15: 5-(1-{4-amino-3-iodo-1H-pyrazolo[3,4-d]pyrimidin-1-yl}ethyl)-4-phenyl-2-(pyridin-3-yl)-2,3-dihydropyridazin-3-one

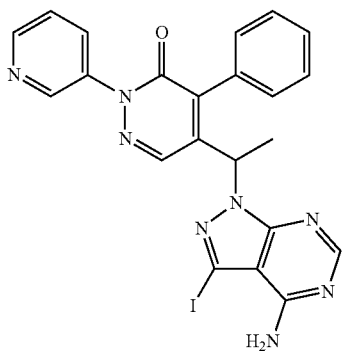 [SMILES: CC(c1cnn(-c2cccnc2)c(=O)c1-c1ccccc1)n1nc(I)c2c(N)ncnc21]

Prepared similarly to intermediate J1 starting from 5-(1-hydroxyethyl)-4-phenyl-2-(pyridin-3-yl)-2,3-dihydropyridazin-3-one G15 (0.121 g), stirring overnight; additional DIAD (1 eq.) was added and the reaction was stirred at r.t. overnight. The crude was purified by flash chromatography on silica gel (DCM:MeOH=99:1 to 97:3) afford title compound as a white solid (0.080 g). MS/ESI+ 536.9 [MH]+, Rt 0.79 min (Method A).

Intermediate and compound J16: 5-(1-{4-amino-3-iodo-1H-pyrazolo[3,4-d]pyrimidin-1-yl}ethyl)-2-benzyl-4-cyclopentyl-2,3-dihydropyridazin-3-one

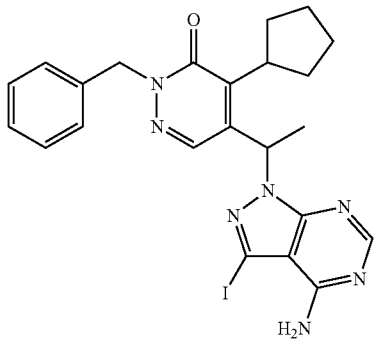 [SMILES: CC(c1cnn(Cc2ccccc2)c(=O)c1C1CCCC1)n1nc(I)c2c(N)ncnc21]

Prepared similarly to intermediate J1 starting from 2-benzyl-4-cyclopentyl-5-(1-hydroxyethyl)-2,3-dihydropyridazin-3-one G16 (0.358 g, 1.201 mmol), stirring overnight, and purified by flash chromatography on Biotage silica gel cartridge (cyclohexane:EtOAc=95:5 to 60:40) followed by filtration on SCX cartridge, washing with MeOH and then eluting with 2M NH$_3$ in MeOH, to afford title compound as a pale yellow solid (0.070 g, 0.148 mmol, 52% yield). MS/ESI+ 542.2 [MH]+, Rt 1.21 min (Method A).

Intermediate and compound J17: 5-({4-amino-3-iodo-1H-pyrazolo[3,4-d]pyrimidin-1-yl}methyl)-2-benzyl-2,3-dihydropyridazin-3-one

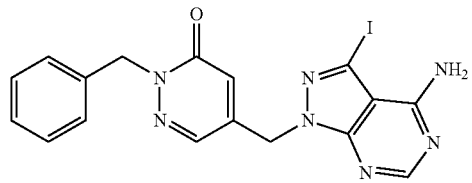 [SMILES: Nc1ncnc2c1c(I)nn2Cc1cnn(Cc2ccccc2)c(=O)c1]

Prepared similarly to intermediate J1 starting from 2-benzyl-5-(hydroxymethyl)-2,3-dihydropyridazin-3-one G17 (0.030 g, 0.138 mmol), stirring for 2 h, and purified by flash chromatography on Biotage silica gel cartridge (DCM to DCM:MeOH=98:2) to afford title compound (0.063 g). MS/ESI+ 460.2 [MH]+, Rt 0.80 min (Method A).

Example 1: 5-{1-[4-amino-3-(3-fluoro-5-hydroxyphenyl)-1H-pyrazolo[3,4-d]pyrimidin-1-yl]ethyl}-2-benzyl-6-phenyl-2,3-dihydropyridazin-3-one

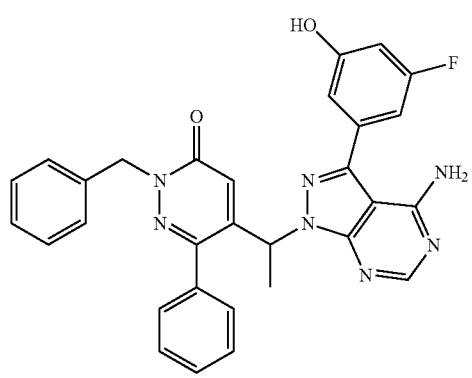 [SMILES: CC(c1cc(=O)n(Cc2ccccc2)nc1-c1ccccc1)n1nc(-c2cc(O)cc(F)c2)c2c(N)ncnc21]

A mixture of 5-(1-{4-amino-3-iodo-1H-pyrazolo[3,4-d]pyrimidin-1-yl}ethyl)-2-benzyl-6-phenyl-2,3-dihydropyridazin-3-one J1 (0.094 g, 0.17 mmol), (3-fluoro-5-hydroxyphenyl)boronic acid (0.029 g, 0.188 mmol) and Pd(PPh$_3$)$_4$ (10 mg, 0.008 mmol) in DME (12 mL), ethanol (2 mL) and saturated aqueous sodium carbonate (4 mL) was stirred at room temperature for 4 hours. The reaction was quenched by addition of water and extracted with DCM; the organic layer was dried over sodium sulfate, filtered and concentrated. The residue was purified by flash chromatography on Biotage silica-NH cartridge (DCM to DCM:MeOH=80:20) to afford title compound (32.2 mg, 0.06 mmol, 35% yield). MS/ESI$^+$ 534.3 [MH]$^+$, Rt 0.95 min (Method A).

$^1$H NMR (400 MHz, DMSO-d$_6$) δ ppm 10.20 (br. s., 1H), 8.08 (s, 1H), 7.21-7.36 (m, 10H), 6.98-7.00 (m, 1H), 6.83-6.87 (m, 1H), 6.74-6.80 (m, 1H), 6.64-6.69 (m, 1H), 6.04 (q, 1H), 6.00-8.00 (m, 2H), 5.19-5.34 (m, 2H), 1.66 (d, 3H).

Example 2: 5-{1-[4-amino-3-(3-fluoro-5-hydroxyphenyl)-1H-pyrazolo[3,4-d]pyrimidin-1-yl]ethyl}-2-methyl-6-phenyl-2,3-dihydropyridazin-3-one

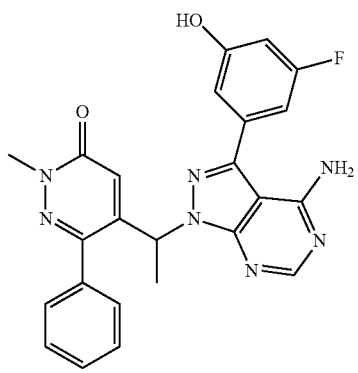 [SMILES: CC(c1cc(=O)n(C)nc1-c1ccccc1)n1nc(-c2cc(O)cc(F)c2)c2c(N)ncnc21]

A mixture of 5-(1-{4-amino-3-iodo-1H-pyrazolo[3,4-d]pyrimidin-1-yl}ethyl)-2-methyl-6-phenyl-2,3-dihydropyridazin-3-one J2 (0.102 g), (3-fluoro-5-hydroxyphenyl)boronic acid (0.037 g, 0.236 mmol), Pd(PPh$_3$)$_4$ (12 mg, 0.01 mmol) in DME (12 mL), ethanol (2 mL) and saturated aqueous sodium carbonate (4 mL) was heated at 80° C. for 4 hours. The reaction was quenched by addition of water and extracted with DCM; the organic layer was dried over sodium sulfate, filtered and concentrated. The residue was purified by flash chromatography on Biotage silica gel cartridge (DCM to DCM:MeOH=80:20) to afford title compound (10.5 mg, 0.022 mmol). MS/ESI$^+$ 458.3 [MH]$^+$, Rt 0.73 min (Method A).

$^1$H NMR (400 MHz, DMSO-d$_6$) δ ppm 10.20 (br. s., 1H), 8.09 (s, 1H), 7.24-7.31 (m, 5H), 6.90-6.93 (m, 1H), 6.84-6.88 (m, 1H), 6.77-6.82 (m, 1H), 6.64-6.69 (m, 1H), 6.25-7.50 (m, 2H), 6.01 (q, 1H), 3.66 (s, 3H), 1.65 (d, 3H).

Example 3: 5-{1-[4-amino-3-(3-fluoro-5-hydroxyphenyl)-1H-pyrazolo[3,4-d]pyrimidin-1-yl]ethyl}-6-phenyl-2-(propan-2-yl)-2,3-dihydropyridazin-3-one

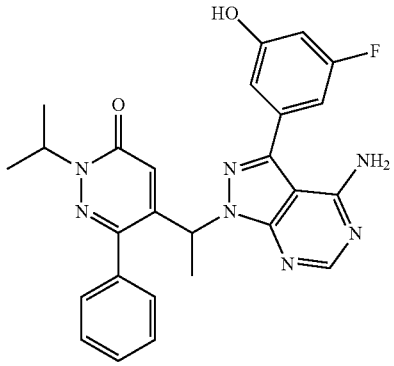 [SMILES: CC(C)n1nc(-c2ccccc2)c(C(C)n2nc(-c3cc(O)cc(F)c3)c3c(N)ncnc32)cc1=O]

Prepared similarly to Example 2, starting from 5-(1-{4-amino-3-iodo-1H-pyrazolo[3,4-d]pyrimidin-1-yl}ethyl)-6-phenyl-2-(propan-2-yl)-2,3-dihydropyridazin-3-one J3 (0.100 g), heating at 80° C. overnight; additional (3-fluoro-5-hydroxyphenyl)-boronic acid (0.5 eq) and Pd(PPh$_3$)$_4$ (0.05 eq) were added and the mixture was heated at the same temperature for further 7 h. The crude was purified by flash chromatography on Biotage silica gel cartridge (DCM to DCM:MeOH=95:5) to afford title compound as a pale yellow powder (0.045 g, 0.093 mmol). MS/ESI$^+$ 486.3 [MH]$^+$, Rt 0.88 min (Method A).

$^1$H NMR (400 MHz, DMSO-d$_6$) δ ppm 10.22 (br. s., 1H), 8.12 (s, 1H), 7.25-7.37 (m, 5H), 6.83-6.89 (m, 2H), 6.76-6.82 (m, 1H), 6.64-6.70 (m, 1H), 6.06 (q, 1H), 6.00-8.00 (m, 2H), 5.09-5.20 (m, 1H), 1.65 (d, 3H), 1.22-1.30 (m, 6H).

Example 4: 5-{1-[4-amino-3-(3-fluoro-5-hydroxyphenyl)-1H-pyrazolo[3,4-d]pyrimidin-1-yl]ethyl}-2-(cyclopropylmethyl)-6-phenyl-2,3-dihydropyridazin-3-one

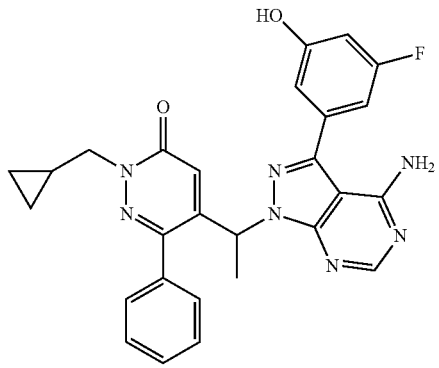 [SMILES: CC(c1cc(=O)n(CC2CC2)nc1-c1ccccc1)n1nc(-c2cc(O)cc(F)c2)c2c(N)ncnc21]

Prepared similarly to Example 2, starting from 5-(1-{4-amino-3-iodo-1H-pyrazolo[3,4-d]pyrimidin-1-yl}ethyl)-2-(cyclopropylmethyl)-6-phenyl-2,3-dihydropyridazin-3-one J4 (0.105 g), heating at 80° C. for 16 h, and purified by flash chromatography on Biotage silica gel cartridge (DCM to DCM:MeOH=80:20) to afford title compound (0.0153 g, 0.031 mmol). MS/ESI$^+$ 498.3 [MH]$^+$, Rt 0.89 min (Method A).

$^1$H NMR (500 MHz, DMSO-d$_6$) δ ppm 10.20 (s, 1H), 8.10 (s, 1H), 7.23-7.34 (m, 5H), 6.92 (s, 1H), 6.86 (s, 1H), 6.76-6.81 (m, 1H), 6.63-6.69 (m, 1H), 6.30-7.90 (m, 2H), 6.05 (q, 1H), 3.83-4.03 (m, 2H), 1.66 (d, 3H), 1.16-1.32 (m, 1H), 0.42-0.51 (m, 2H), 0.29-0.41 (m, 2H).

Example 5: 5-{1-[4-amino-3-(3-fluoro-5-hydroxyphenyl)-1H-pyrazolo[3,4-d]pyrimidin-1-yl]ethyl}-2,6-diphenyl-2,3-dihydropyridazin-3-one

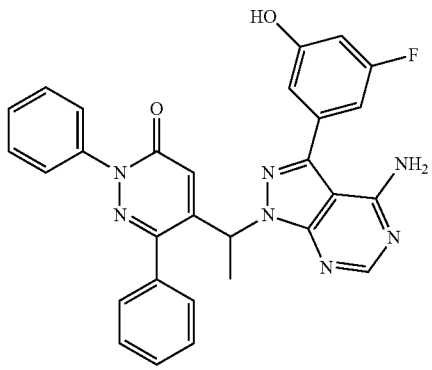 [SMILES: CC(c1cc(=O)n(-c2ccccc2)nc1-c1ccccc1)n1nc(-c2cc(O)cc(F)c2)c2c(N)ncnc21]

Prepared similarly to Example 2, starting from 5-(1-{4-amino-3-iodo-1H-pyrazolo[3,4-d]pyrimidin-1-yl}ethyl)-2,6-diphenyl-2,3-dihydropyridazin-3-one J5 (0.033 g), heating at 80° C. for 4 h, and purified by flash chromatography on Biotage silica gel cartridge (DCM to DCM:MeOH=80:20) to afford title compound (0.0142 g, 0.027 mmol). MS/ESI⁺ 520.3 [MH]⁺, Rt 0.91 min (Method A).

$^1$H NMR (500 MHz, DMSO-d$_6$) δ ppm 10.23 (s, 1H), 8.13 (s, 1H), 7.59-7.64 (m, 2H), 7.46-7.52 (m, 2H), 7.36-7.44 (m, 3H), 7.24-7.34 (m, 3H), 7.07 (s, 1H), 6.89 (s, 1H), 6.80-6.85 (m, 1H), 6.65-6.71 (m, 1H), 6.11 (q, 1H), 1.71 (d, 3H).

Example 6: 5-{1-[4-amino-3-(3-fluoro-5-hydroxyphenyl)-1H-pyrazolo[3,4-d]pyrimidin-1-yl]ethyl}-6-phenyl-2-(pyridin-2-ylmethyl)-2,3-dihydropyridazin-3-one

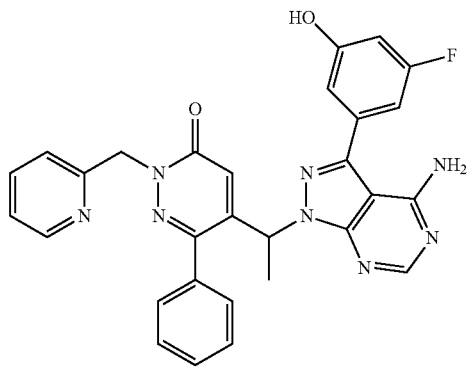 [SMILES: CC(c1cc(=O)n(Cc2ccccn2)nc1-c1ccccc1)n1nc(-c2cc(O)cc(F)c2)c2c(N)ncnc21]

Prepared similarly to Example 2, starting from 5-(1-{4-amino-3-iodo-1H-pyrazolo[3,4-d]pyrimidin-1-yl}ethyl)-6-phenyl-2-(pyridin-2-ylmethyl)-2,3-dihydropyridazin-3-one J6 (0.031 g), heating at 80° C. for 16 h, and purified by flash chromatography on Biotage silica gel cartridge (DCM to DCM:MeOH=80:20) to afford title compound (7.7 mg, 0.014 mmol). MS/ESI⁺ 535.3 [MH]⁺, Rt 0.73 min (Method A).

$^1$H NMR (400 MHz, DMSO-d$_6$) δ ppm 10.24 (s, 1H), 8.50 (d, 1H), 8.11 (s, 1H), 7.76 (td, 1H), 7.20-7.32 (m, 7H), 7.02 (s, 1H), 6.87 (s, 1H), 6.77-6.83 (m, 1H), 6.65-6.71 (m, 1H), 6.20-8.00 (m, 2H), 6.09 (q, 1H), 5.31-5.46 (m, 2H), 1.69 (d, 3H).

Example 7: 5-{1-[4-amino-3-(3-fluoro-5-hydroxyphenyl)-1H-pyrazolo[3,4-d]pyrimidin-1-yl]ethyl}-2-benzyl-2,3-dihydropyridazin-3-one

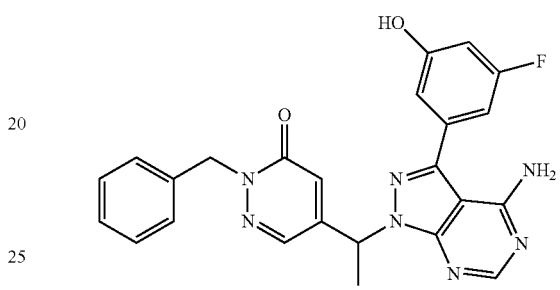

Prepared similarly to Example 2, starting from 5-(1-{4-amino-3-iodo-1H-pyrazolo[3,4-d]pyrimidin-1-yl}ethyl)-2-benzyl-2,3-dihydropyridazin-3-one J7 (0.287 g, 0.607 mmol), heating at 80° C. for 2 h, and purified by flash chromatography on Biotage silica-NH cartridge (DCM to DCM:MeOH=80:20) to afford title compound (0.026 g, 0.057 mmol, 9% yield). MS/ESI⁺ 458.0 [MH]⁺, Rt 0.85 min (Method A).

$^1$H NMR (400 MHz, DMSO-d$_6$) δ ppm 10.22 (br. s., 1H), 8.26 (s, 1H), 7.95 (d, J=2.1 Hz, 1H), 7.23-7.35 (m, 5H), 6.91-6.94 (m, 1H), 6.86-6.91 (m, 1H), 6.64-6.71 (m, 2H), 6.06 (q, J=7.0 Hz, 1H), 6.00-8.00 (m, 2H), 5.15-5.24 (m, 2H), 1.85 (d, J=7.2 Hz, 3H).

Example 8: 5-{1-[4-amino-3-(3-fluoro-5-hydroxyphenyl)-1H-pyrazolo[3,4-d]pyrimidin-1-yl]ethyl}-2-phenyl-2,3-dihydropyridazin-3-one

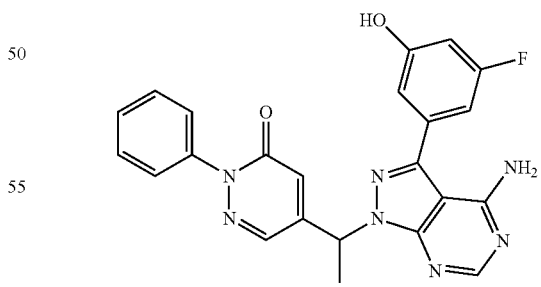

Prepared similarly to Example 2, starting from 5-(1-{4-amino-3-iodo-1H-pyrazolo[3,4-d]pyrimidin-1-yl}ethyl)-2-phenyl-2,3-dihydropyridazin-3-one J8 (0.170 g), heating at 80° C. for 2 h, and purified by flash chromatography on Biotage silica-NH cartridge (DCM to DCM:MeOH=80:20) to afford title compound (0.032 g, 0.072 mmol). MS/ESI⁺ 444.3 [MH]⁺, Rt 0.82 min (Method A).

¹H NMR (400 MHz, DMSO-d₆) δ ppm 10.23 (s, 1H), 8.29 (s, 1H), 8.09 (d, 1H), 7.38-7.54 (m, 5H), 6.94-6.97 (m, 1H), 6.89-6.94 (m, 1H), 6.77-6.80 (m, 1H), 6.65-6.71 (m, 1H), 6.25-8.00 (m, 2H), 6.13 (q, 1H), 1.91 (d, 3H).

Example 9: 5-{1-[4-amino-3-(3-fluoro-5-hydroxyphenyl)-1H-pyrazolo[3,4-d]pyrimidin-1-yl]ethyl}-2-methyl-2,3-dihydropyridazin-3-one

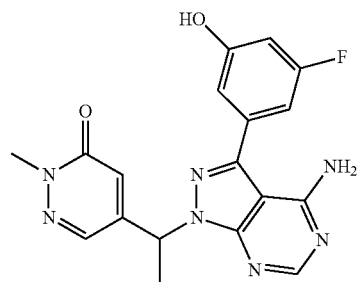 [SMILES: CC(c1cnn(C)c(=O)c1)n1nc(-c2cc(O)cc(F)c2)c2c(N)ncnc21]

Prepared similarly to Example 2, starting from 5-(1-{4-amino-3-iodo-1H-pyrazolo[3,4-d]pyrimidin-1-yl}ethyl)-2-methyl-2,3-dihydropyridazin-3-one J9 (0.115 g), heating at 80° C. for 4 h, and purified by flash chromatography on Biotage silica gel cartridge (DCM to DCM:MeOH=80:20) to afford title compound (0.067 g, 0.175 mmol). MS/ESI⁺ 382.3 [MH]⁺, Rt 0.62 min (Method A).

¹H NMR (400 MHz, DMSO-d₆) δ ppm 10.20 (s, 1H), 8.27 (s, 1H), 7.89 (d, 1H), 6.92-6.94 (m, 1H), 6.87-6.92 (m, 1H), 6.64-6.71 (m, 2H), 6.01-6.09 (m, 1H), 6.10-8.00 (m, 2H), 3.59 (s, 3H), 1.85 (d, 3H).

Example 10: 5-{1-[4-amino-3-(3-fluoro-5-hydroxyphenyl)-1H-pyrazolo[3,4-d]pyrimidin-1-yl]ethyl}-2-tert-butyl-4-phenyl-2,3-dihydropyridazin-3-one

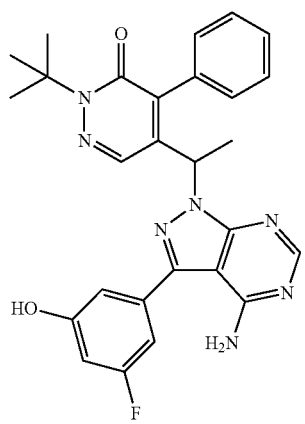 [SMILES: CC(c1cnn(C(C)(C)C)c(=O)c1-c1ccccc1)n1nc(-c2cc(O)cc(F)c2)c2c(N)ncnc21]

Prepared similarly to Example 2, starting from 5-(1-{4-amino-3-iodo-1H-pyrazolo[3,4-d]pyrimidin-1-yl}ethyl)-2-tert-butyl-4-phenyl-2,3-dihydropyridazin-3-one J10 (0.135 g), heating at 80° C. for 3 h, and purified by flash chromatography on Biotage silica-NH cartridge (EtOAc to EtOAc:MeOH=80:20) and dried to afford title compound as white solid (0.046 g, 0.092 mmol). MS/ESI⁺ 500.4 [MH]⁺, Rt 1.06 min (Method A).

¹H NMR (400 MHz, DMSO-d₆) δ ppm 10.28 (br. s., 1H), 8.18 (s, 1H), 8.10 (s, 1H), 7.41-7.52 (m, 3H), 7.30-7.38 (m, 2H), 6.94-6.98 (m, 1H), 6.89-6.94 (m, 1H), 6.66-6.73 (m, 1H), 6.20-7.80 (m, 2H), 5.82 (q, 1H), 1.78 (d, 3H), 1.57 (s, 9H).

Example 11: 5-{1-[4-amino-3-(3-fluoro-5-hydroxyphenyl)-1H-pyrazolo[3,4-d]pyrimidin-1-yl]ethyl}-2-benzyl-4-phenyl-2,3-dihydropyridazin-3-one

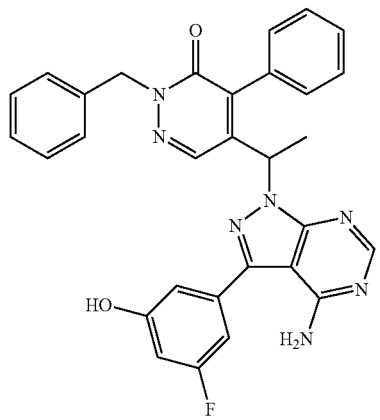 [SMILES: CC(c1cnn(Cc2ccccc2)c(=O)c1-c1ccccc1)n1nc(-c2cc(O)cc(F)c2)c2c(N)ncnc21]

Prepared similarly to Example 2, starting from 5-(1-{4-amino-3-iodo-1H-pyrazolo[3,4-d]pyrimidin-1-yl}ethyl)-2-benzyl-4-phenyl-2,3-dihydropyridazin-3-one J11 (0.93 g), and purified by flash chromatography on Biotage silica gel cartridge (DCM:MeOH=99:1 to 90:10) to afford title compound as a white solid (0.041 g, 0.077 mmol). MS/ESI⁺ 534.3 [MH]⁺, Rt 1.02 min (Method A).

¹H NMR (400 MHz, DMSO-d₆) δ ppm 10.23 (s, 1H), 8.20 (s, 1H), 8.15 (s, 1H), 7.42-7.50 (m, 3H), 7.27-7.37 (m, 7H), 6.88-6.95 (m, 2H), 6.66-6.71 (m, 1H), 6.40-8.05 (m, 2H), 5.83 (q, J=7.2 Hz, 1H), 5.16-5.31 (m, 2H), 1.78 (d, J=7.0 Hz, 3H).

Example 12: 5-{1-[4-amino-3-(3-fluoro-5-hydroxyphenyl)-1H-pyrazolo[3,4-d]pyrimidin-1-yl]ethyl}-2-methyl-4-phenyl-2,3-dihydropyridazin-3-one

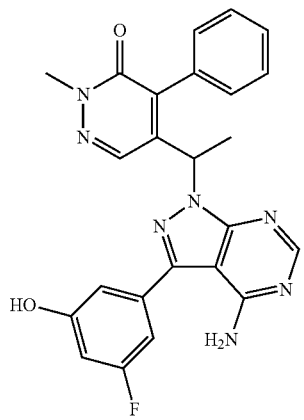 [SMILES: CC(c1cnn(C)c(=O)c1-c1ccccc1)n1nc(-c2cc(O)cc(F)c2)c2c(N)ncnc21]

Prepared similarly to Example 2, starting from 5-(1-{4-amino-3-iodo-1H-pyrazolo[3,4-d]pyrimidin-1-yl}ethyl)-2- methyl-4-phenyl-2,3-dihydropyridazin-3-one J12 (0.069 g, 0.146), heating at 80° C. for 2 h; additional (3-fluoro-5-hydroxyphenyl)boronic acid (1.1 eq) and Pd(PPh$_3$)$_4$ (0.05 eq) were added and the mixture was heated at the same temperature overnight. The crude was purified by flash chromatography on Biotage silica gel cartridge (DCM to DCM:MeOH=94:6) to afford title compound as an off-white solid (0.033 g, 0.072 mmol, 49% yield). MS/ESI$^+$ 458.2 [MH]$^+$, Rt 0.71 min (Method B).

$^1$H NMR (400 MHz, DMSO-d$_6$) δ ppm 10.22 (br. s., 1H), 8.15 (s, 1H), 8.11 (s, 1H), 7.41-7.50 (m, 3H), 7.30-7.36 (m, 2H), 6.92-6.95 (m, 1H), 6.87-6.92 (m, 1H), 6.65-6.71 (m, 1H), 6.10-7.80 (m, 2H), 5.77-5.84 (m, 1H), 3.64 (s, 3H), 1.77 (d, J=7.2 Hz, 3H).

Example 13: 5-{1-[4-amino-3-(3-fluoro-5-hydroxyphenyl)-1H-pyrazolo[3,4-d]pyrimidin-1-yl]ethyl}-2,4-diphenyl-2,3-dihydropyridazin-3-one

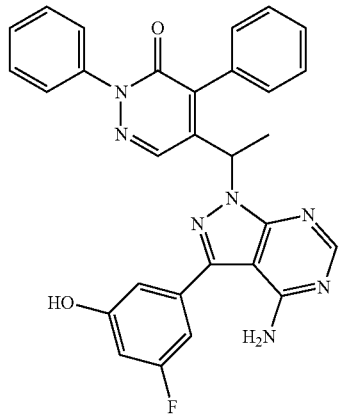 [SMILES: CC(c1cnn(-c2ccccc2)c(=O)c1-c1ccccc1)n1nc(-c2cc(O)cc(F)c2)c2c(N)ncnc21]

Prepared similarly to Example 2, starting from 5-(1-{4-amino-3-iodo-1H-pyrazolo[3,4-d]pyrimidin-1-yl}ethyl)-2,4-diphenyl-2,3-dihydropyridazin-3-one J13 (0.078 g, 0.146 mmol), heating at 80° C. for 2 h; additional (3-fluoro-5-hydroxyphenyl)boronic acid (1.1 eq) and Pd(PPh$_3$)$_4$ (0.05) were added and the mixture was heated at the same temperature overnight. The crude was purified by flash chromatography on Biotage silica gel cartridge (DCM to DCM:EtOAc=40:60) to afford title compound as a beige solid (0.037 g, 0.071 mmol, 49% yield). MS/ESI$^+$ 520.3 [MH]$^+$, Rt 0.97 min (Method A).

$^1$H NMR (400 MHz, DMSO-d$_6$) δ ppm 10.22 (s, 1H), 8.34 (s, 1H), 8.18 (s, 1H), 7.53-7.59 (m, 2H), 7.38-7.52 (m, 8H), 6.90-6.97 (m, 2H), 6.66-6.72 (m, 2H), 6.20-8.30 (m, 2H), 5.85-5.92 (m, 1H), 1.84 (d, 3H).

Example 14: 5-{1-[4-amino-3-(3-fluoro-5-hydroxyphenyl)-1H-pyrazolo[3,4-d]pyrimidin-1-yl]ethyl}-2-[2-(morpholin-4-yl)ethyl]-4-phenyl-2,3-dihydropyridazin-3-one

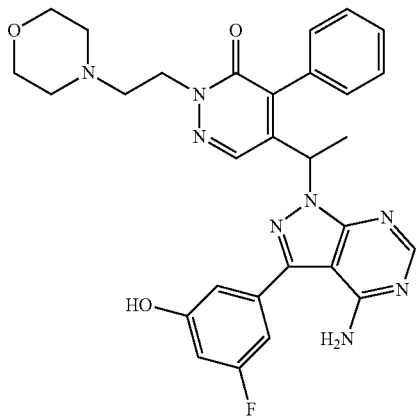 [SMILES: CC(c1cnn(CCN2CCOCC2)c(=O)c1-c1ccccc1)n1nc(-c2cc(O)cc(F)c2)c2c(N)ncnc21]

Prepared similarly to Example 2, starting from 5-(1-{4-amino-3-iodo-1H-pyrazolo[3,4-d]pyrimidin-1-yl}ethyl)-2-[2-(morpholin-4-yl)ethyl]-4-phenyl-2,3-dihydropyridazin-3-one J14 (0.114), heating at 80° C. overnight; additional (3-fluoro-5-hydroxyphenyl)boronic acid (1.1 eq) and Pd(PPh$_3$)$_4$ (0.05 eq) were added and the mixture was heated at the same temperature for further 2 h. The crude was purified by flash chromatography on Biotage silica-NH cartridge (DCM to DCM:MeOH to 90:10) to afford title compound as a white solid (0.056 g, 0.099 mmol). MS/ESI$^+$ 557.4 [MH]$^+$, Rt 0.54 min (Method A).

$^1$H NMR (500 MHz, DMSO-d$_6$) δ ppm 10.22 (br. s., 1H), 8.14-8.18 (m, 2H), 7.37-7.50 (m, 3H), 7.28-7.36 (m, 2H), 6.91-6.95 (m, 1H), 6.85-6.91 (m, 1H), 6.68 (dt, 1H), 5.93-8.36 (m, 2H), 5.82 (q, 1H), 4.10-4.23 (m, 2H), 3.45-3.53 (m, 4H), 2.63 (t, 2H), 2.34-2.44 (m, 4H), 1.78 (d, 3H).

Example 15: 5-{1-[4-amino-3-(3-fluoro-5-hydroxyphenyl)-1H-pyrazolo[3,4-d]pyrimidin-1-yl]ethyl}-4-phenyl-2-(pyridin-3-yl)-2,3-dihydropyridazin-3-one

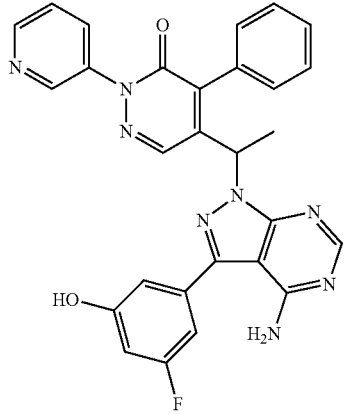 [SMILES: CC(c1cnn(-c2cccnc2)c(=O)c1-c1ccccc1)n1nc(-c2cc(O)cc(F)c2)c2c(N)ncnc21]

Prepared similarly to Example 2, starting from 5-(1-{4-amino-3-iodo-1H-pyrazolo[3,4-d]pyrimidin-1-yl}ethyl)-4-phenyl-2-(pyridin-3-yl)-2,3-dihydropyridazin-3-on J15

(0.080 g), heating at 65° C. overnight; additional (3-fluoro-5-hydroxyphenyl)-boronic acid (1.1 eq) and Pd(PPh₃)₄ (0.06) were added and the mixture was heated at 80° C. for 2 h. The crude was purified by flash chromatography on silica-NH cartridge (DCM:MeOH=99:1 to 90:10) to afford title compound as a white solid (0.024 g, 0.046 mmol). MS/ESI⁺ 521.3 [MH]⁺, Rt 0.81 min (Method A).

¹H NMR (400 MHz, DMSO-d₆) δ ppm 10.23 (br. s., 1H), 8.82 (d, 1H), 8.59 (dd, 1H), 8.41 (s, 1H), 8.19 (s, 1H), 8.03-8.09 (m, 1H), 7.42-7.57 (m, 6H), 6.91-6.99 (m, 2H), 6.66-6.73 (m, 1H), 6.00-8.00 (m, 2H), 5.91 (q, 1H), 1.85 (d, 3H).

Example 16: 5-{1-[4-amino-3-(3-fluoro-5-hydroxyphenyl)-1H-pyrazolo[3,4-d]pyrimidin-1-yl]ethyl}-2-benzyl-4-cyclopentyl-2,3-dihydropyridazin-3-one

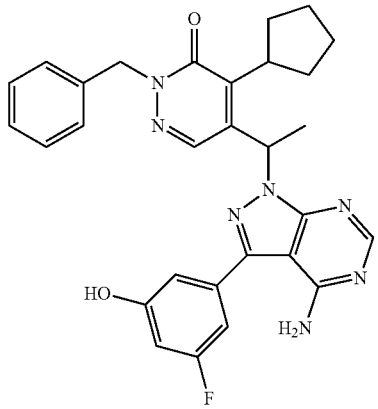 [SMILES: CC(c1cnn(Cc2ccccc2)c(=O)c1C1CCCC1)n1nc(-c2cc(O)cc(F)c2)c2c(N)ncnc21]

Prepared similarly to Example 2, starting from 5-(1-{4-amino-3-iodo-1H-pyrazolo[3,4-d]pyrimidin-1-yl}ethyl)-2-benzyl-4-cyclopentyl-2,3-dihydropyridazin-3-one J16 (0.200 g, 0.369 mmol), heating at 80° C. overnight, and purified by flash chromatography on Biotage silica gel cartridge (cyclohexane:EtOAc=90:10 to 100% EtOAc) to afford title compound as a white solid (0.107 g, 0.099 mmol, 55% yield). MS/ESI⁺ 526.4 [MH]⁺, Rt 1.17 min (Method A).

¹H NMR (400 MHz, DMSO-d₆) δ ppm 10.20 (s, 1H), 8.25 (s, 1H), 7.94 (s, 1H), 7.20-7.37 (m, 5H), 6.85-6.96 (m, 2H), 6.64-6.76 (m, 1H), 6.33-6.41 (m, 1H), 5.95-7.77 (m, 2H), 5.00-5.31 (m, 2H), 3.52 (quin, 1H), 1.32-2.13 (m, 11H).

Example 17: 5-{1-[4-amino-3-(5-hydroxypyridin-3-yl)-1H-pyrazolo[3,4-d]pyrimidin-1-yl]ethyl}-2-benzyl-4-cyclopentyl-2,3-dihydropyridazin-3-one

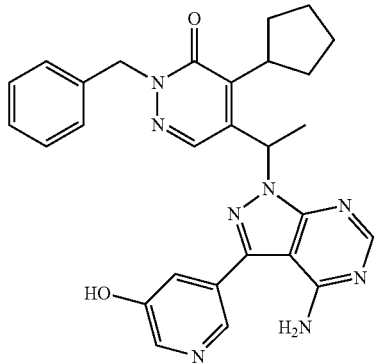 [SMILES: CC(c1cnn(Cc2ccccc2)c(=O)c1C1CCCC1)n1nc(-c2cncc(O)c2)c2c(N)ncnc21]

To a mixture of 5-(1-{4-amino-3-iodo-1H-pyrazolo[3,4-d]pyrimidin-1-yl}ethyl)-2-benzyl-4-cyclopentyl-2,3-dihy-dropyridazin-3-one J16 (0.214 g, 0.395 mmol), 5-(tetramethyl-1,3,2-dioxaborolan-2-yl)pyridin-3-ol (0.105 g, 0.474 mmol) in DME (20 mL), Pd(PPh₃)₄ (0.023 g, 0.019 mmol), ethanol (3 mL) and saturated aqueous sodium carbonate (5 mL) were added and the reaction was stirred at 80° C. for 3 h. The reaction was quenched by addition of water and extracted with DCM; the organic layer was dried over sodium sulfate, filtered and concentrated. The residue was purified by flash chromatography on Biotage silica gel cartridge (cyclohexane:EtOAc=98:2 to 80:20) to afford title compound (0.093 g, 0.183 mmol, 46% yield). MS/ESI⁺ 509.4 [MH]⁺, Rt 0.94 min (Method A).

1H NMR (400 MHz, DMSO-d₆) δ ppm 10.12-10.25 (m, 1H), 8.31 (d, 1H), 8.26 (s, 1H), 8.22 (d, 1H), 7.95 (s, 1H), 7.40 (dd, 1H), 7.22-7.35 (m, 5H), 6.96-7.65 (m, 2H), 6.37 (q, 1H), 5.09-5.26 (m, 2H), 3.53 (quin, 1H), 1.87 (d, 3H), 1.33-2.17 (m, 8H).

Example 18: 5-{[4-amino-3-(3-fluoro-5-hydroxyphenyl)-1H-pyrazolo[3,4-d]pyrimidin-1-yl]methyl}-2-benzyl-2,3-dihydropyridazin-3-one

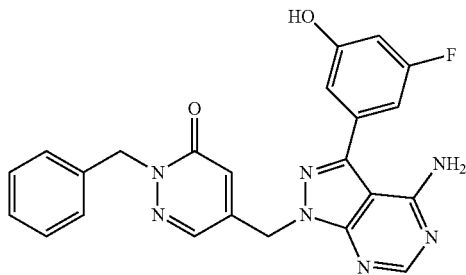 [SMILES: Nc1ncnc2c1c(-c1cc(O)cc(F)c1)nn2Cc1cnn(Cc2ccccc2)c(=O)c1]

Prepared similarly to Example 2, starting from 5-({4-amino-3-iodo-1H-pyrazolo[3,4-d]pyrimidin-1-yl}methyl)-2-benzyl-2,3-dihydropyridazin-3-one J17 (0.063 g), heating at 80° C. for 2 h, and purified by flash chromatography on Biotage silica NH-cartridge (DCM to DCM:MeOH=80:20) to afford title compound (0.015 g, 0.03 mmol). MS/ESI⁺ 444.2 [MH]⁺, Rt 0.82 min (Method A).

¹H NMR (400 MHz, DMSO-d₆) δ ppm 10.19 (br. s., 1H), 8.28 (s, 1H), 7.90 (d, J=2.01 Hz, 1H), 7.24-7.34 (m, 5H), 6.91-6.93 (m, 1H), 6.85-6.90 (m, 1H), 6.64-6.70 (m, 1H), 6.55-6.57 (m, 1H), 6.40-7.80 (m, 2H), 5.53 (s, 2H), 5.20 (s, 2H).

Example 19: 4-amino-6-{[1-(1-benzyl-6-oxo-3-phenyl-1,6-dihydropyridazin-4-yl)ethyl]amino}pyrimidine-5-carbonitrile

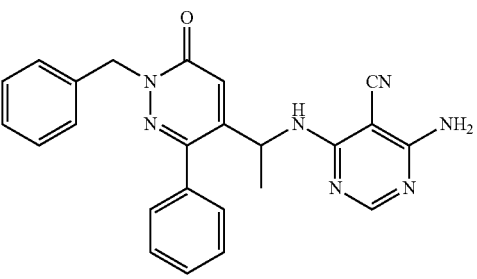 [SMILES: CC(Nc1ncnc(N)c1C#N)c1cc(=O)n(Cc2ccccc2)nc1-c1ccccc1]

To a solution of 5-(1-aminoethyl)-2-benzyl-6-phenyl-2,3-dihydropyridazin-3-one I1 (0.056 g, 0.183 mmol) in t-BuOH (2 mL), 4-amino-6-chloropyrimidine-5-carbonitrile (0.028 g, 0.183 mmol) was added followed by DIPEA (0.064 mL, 0.366 mmol) and the resulting mixture was heated to reflux overnight. The solvent was removed under reduced pressure and the crude was purified by flash chromatography on Biotage silica gel cartridge (DCM:MeOH=99:1 to 90:10) to afford title compound (0.044 g, 0.10 mmol, 57% yield). MS/ESI$^+$ 424.3 [MH]$^+$, Rt 0.98 min (Method A).

$^1$H NMR (400 MHz, DMSO-d$_6$) δ ppm 7.96 (s, 1H), 7.77 (d, 1H), 7.55-7.59 (m, 2H), 7.43-7.50 (m, 3H), 7.24-7.37 (m, 7H), 7.04 (s, 1H), 5.20-5.30 (m, 2H), 5.01-5.10 (m, 1H), 1.23 (d, 3H).

Example 20: 4-amino-6-(1-(1-methyl-6-oxo-3-phenyl-1,6-dihydropyridazin-4-yl)ethylamino)pyrimidine-5-carbonitrile

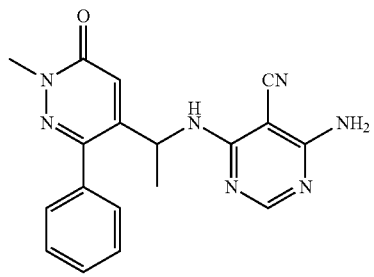 [SMILES: CC(Nc1ncnc(N)c1C#N)c1cc(=O)n(C)nc1-c1ccccc1]

Prepared similarly to Example 19 starting from 5-(1-aminoethyl)-2-methyl-6-phenyl-2,3-dihydropyridazin-3-one I2 (0.032 g, 0.141 mmol) and purified by flash chromatography on Biotage silica gel cartridge (DCM:MeOH=99:1 to 90:10) to afford title compound (0.033 g, 0.09 mmol, 67% yield). MS/ESI$^+$ 348.2 [MH]$^+$, Rt 0.73 min (Method A).

$^1$H NMR (400 MHz, DMSO-d$_6$) δ ppm 7.96 (s, 1H), 7.75 (d, 1H), 7.55-7.60 (m, 2H), 7.42-7.51 (m, 3H), 7.27 (br. s., 2H), 6.98 (s, 1H), 4.97-5.05 (m, 1H), 3.65 (s, 3H), 1.22 (d, 3H).

Example 21: 4-amino-6-({1-[6-oxo-3-phenyl-1-(propan-2-yl)-1,6-dihydropyridazin-4-yl]ethyl}amino)pyrimidine-5-carbonitrile

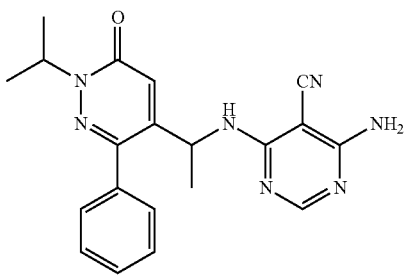 [SMILES: CC(Nc1ncnc(N)c1C#N)c1cc(=O)n(C(C)C)nc1-c1ccccc1]

Prepared similarly to Example 19 starting from 5-(1-aminoethyl)-6-phenyl-2-(propan-2-yl)-2,3-dihydropyridazin-3-one I3 (0.030 g, 0.116 mmol) and purified by flash chromatography on Biotage silica-NH SNAP cartridge (cyclohexane:EtOAc=80:20 to 40:60) to afford title compound as a white solid (0.029 g, 0.077 mmol, 67% yield). MS/ESI$^+$ 376.1 [MH]$^+$, Rt 0.87 min (Method A).

$^1$H NMR (400 MHz, DMSO-d$_6$) δ ppm 7.97 (s, 1H), 7.77 (d, 1H), 7.55-7.61 (m, 2H), 7.43-7.51 (m, 3H), 7.28 (br. s., 2H), 6.96 (s, 1H), 5.09-5.19 (m, 2H), 1.19-1.32 (m, 9H).

Example 22: 4-amino-6-({1-[1-(cyclopropylmethyl)-6-oxo-3-phenyl-1,6-dihydropyridazin-4-yl]ethyl}amino)pyrimidine-5-carbonitrile

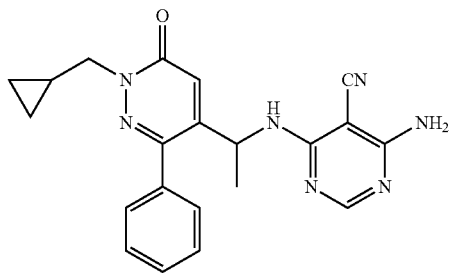 [SMILES: CC(Nc1ncnc(N)c1C#N)c1cc(=O)n(CC2CC2)nc1-c1ccccc1]

Prepared similarly to Example 19 starting from 5-(1-aminoethyl)-2-(cyclopropylmethyl)-6-phenyl-2,3-dihydropyridazin-3-one I4 (0.020 g) and purified by flash chromatography on Biotage silica gel cartridge (DCM:MeOH=99:1 to 90:10) to afford title compound (0.0187 g, 0.048 mmol). MS/ESI$^+$ 388.3 [MH]$^+$, Rt 0.90 min (Method A).

$^1$H NMR (400 MHz, DMSO-d$_6$) δ ppm 7.98 (s, 1H), 7.79 (d, 1H), 7.56-7.61 (m, 2H), 7.44-7.51 (m, 3H), 7.30 (br. s., 2H), 7.00 (s, 1H), 5.04-5.12 (m, 1H), 3.86-4.00 (m, 2H), 1.20-1.30 (m, 4H), 0.45-0.51 (m, 2H), 0.32-0.40 (m, 2H).

Example 23: 4-amino-6-{[1-(6-oxo-1,3-diphenyl-1,6-dihydropyridazin-4-yl)ethyl]amino}pyrimidine-5-carbonitrile

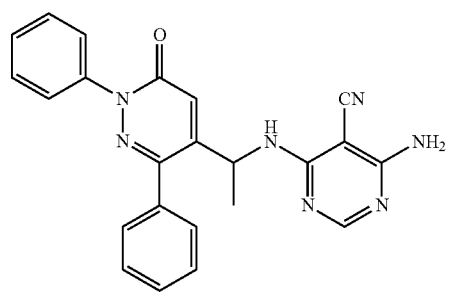 [SMILES: CC(Nc1ncnc(N)c1C#N)c1cc(=O)n(-c2ccccc2)nc1-c1ccccc1]

Prepared similarly to Example 19 starting from 5-(1-aminoethyl)-2,6-diphenyl-2,3-dihydropyridazin-3-one I5 (0.023 g) and purified by flash chromatography on Biotage silica gel cartridge (DCM:MeOH=99:1 to 90:10) to afford title compound (17.2 mg, 0.042 mmol). MS/ESI$^+$ 410.3 [MH]$^+$, Rt 0.93 min (Method A).

$^1$H NMR (400 MHz, DMSO-d$_6$) δ ppm 8.01 (s, 1H), 7.84 (d, 1H), 7.64-7.69 (m, 2H), 7.58-7.64 (m, 2H), 7.45-7.54 (m, 5H), 7.38-7.45 (m, 1H), 7.32 (br. s., 2H), 7.13 (s, 1H), 5.08-5.17 (m, 1H), 1.28 (d, 3H).

Example 24: 2-benzyl-6-phenyl-5-{1-[(9H-purin-6-yl)amino]ethyl}-2,3-dihydropyridazin-3-one

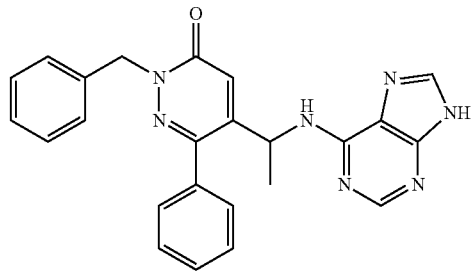 [SMILES: CC(Nc1ncnc2[nH]cnc12)c1cc(=O)n(Cc2ccccc2)nc1-c1ccccc1]

To a solution of 5-(1-aminoethyl)-2-benzyl-6-phenyl-2,3-dihydropyridazin-3-one I1 (0.056 g, 0.183 mmol) in t-BuOH (2 mL), 6-bromopurine (0.036 g, 0.183 mmol) was added followed by DIPEA (0.064 mL, 0.366 mmol) and the resulting mixture was heated to reflux overnight. The solvent was removed under reduced pressure and the crude was purified by flash chromatography on Biotage silica gel cartridge (DCM:MeOH=99:1 to 90:10) to afford title compound (0.0337 g, 0.079 mmol, 43% yield). MS/ESI⁺ 424.3 [MH]⁺, Rt 0.85 min (Method A).

$^1$H NMR (400 MHz, DMSO-$d_6$) δ ppm 13.01 (br. s., 1H), 8.05-8.48 (m, 3H), 7.69 (br. s., 2H), 7.44-7.57 (m, 3H), 7.24-7.39 (m, 5H), 7.04 (br. s., 1H), 5.08-5.34 (m, 3H), 1.27 (br. s., 3H).

Pharmacological Activity of the Compounds of the Present Invention.

In vitro Determination of the PI3K Enzyme Inhibitory Activity in the Cell Free Assay.

Human recombinant proteins PI3Kα, PI3Kβ, PI3Kγ, and PI3Kδ were purchased from Millipore Ltd (Billerica, Mass.). Compounds were dissolved at 0.5 mM in DMSO and were tested at different concentrations for their activity against PI3Ks using the ADP-Glo™ Kinase Assay (Promega, Madison Wis.) according to the manufacturer's instructions. Briefly, the kinase reactions were performed in 384-well white plates (Greiner Bio-One GmbH, Frickenhausen). Each well was loaded with 0.1 μl of test compound and 2.5 μl of 2× reaction buffer (40 mM Tris pH7.5, 0.5 mM EGTA, 0.5 mM Na₃VO₄, 5 mM β-glycerophosphate, 0.1 mg/ml BSA, 1 mM DTT), containing 50 μM PI and PS substrates (L-α-phosphatidylinositol sodium salt and L-α-phosphatidyl-L-serine, Sigma-Aldrich, St. Louis Mo.) and the PI3K recombinant proteins (PI3Kγ 0.25 ng/μl, PI3Kδ 1 ng/μl, PI3Kα 0.125 ng/μl, and PI3Kβ 1 ng/μl).

The reactions were started by adding 2.5 μl of 2×ATP solution to each well (final concentrations: PI3Kγ ATP 30 μM; PI3Kδ ATP 80 μM; PI3Kα ATP 50 μM; PI3Kβ ATP 100 μM) and incubated for 60 min at room temperature. Subsequently, each kinase reaction was incubated for 40 min with 5 μl ADP-Glo™ Reagent, allowing depletion of unconsumed ATP. Then, the Kinase Detection Reagent (10 μl) was added in each well to convert ADP to ATP and to allow the newly synthesized ATP to be measured using a luciferase/luciferin reaction. Following 60 min incubation, the luminescence signal was measured using a Wallac EnVision® multilabel reader (PerkinElmer, Waltham Mass.).

Curve fitting and IC50 calculation were carried out using a four-parameter logistic model in XLfit (IDBS, Guilford, UK) for Microsoft Excel (Microsoft, Redmont, Wash.). The compounds according to the present invention showed IC50 even lower than 100 nM, or even IC50<10 nM in the PI3Kdelta inhibitory assay herein above described. The results are provided in the Table below.

TABLE

Results of the in vitro determination of the PI3K enzyme inhibitory activity in the cell free assay.

| Compound of Example N. | PI3K delta inhibition | PI3K gamma inhibition | PI3K alpha inhibition | PI3K beta inhibition |
|---|---|---|---|---|
| 1 | ++ | + | + | ++ |
| 2 | ++ | ++ | + | ++ |
| 3 | ++ | + | + | ++ |
| 4 | ++ | + | + | ++ |
| 5 | ++ | ++ | + | ++ |
| 6 | ++ | + | + | ++ |
| 7 | +++ | ++ | ++ | +++ |
| 8 | +++ | ++ | ++ | +++ |
| 9 | +++ | ++ | ++ | ++ |
| 10 | +++ | + | + | ++ |
| 11 | +++ | + | + | ++ |
| 12 | +++ | ++ | + | ++ |
| 13 | ++ | ++ | ++ | ++ |
| 14 | +++ | + | + | + |
| 15 | +++ | ++ | + | ++ |
| 16 | +++ | + | + | ++ |
| 17 | +++ | ++ | + | ++ |
| 18 | +++ | ++ | ++ | ++ |
| 19 | + | + | + | + |
| 20 | ++ | + | + | + |
| 21 | + | + | + | + |
| 22 | + | + | + | + |
| 23 | + | + | + | + |
| 24 | + | + | + | + | wherein the compounds are classified in term of potency with respect to their inhibitory activity on PI3K -alpha, -beta, -gamma and -delta according to the following:
+++: IC50 < 10 nM
++: IC50 in the range 10-1000 nM
+: IC50 > 1000 nM Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

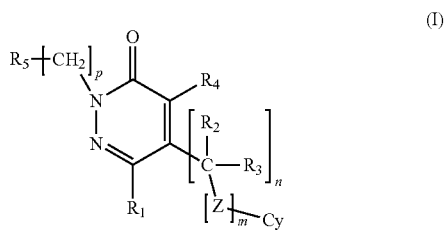

wherein $R_1$ and $R_4$ may be the same or different and are each independently H, halogen, —CN, —(CH$_2$)$_p$NR$_6$R$_7$, (C$_1$-C$_6$) alkyl, (C$_1$-C$_6$) haloalkyl, (C$_1$-C$_6$) hydroxyalkyl, ($C_1$-$C_6$) aminoalkyl, ($C_1$-$C_6$) alkanoyl, ($C_3$-$C_7$) cycloalkyl, ($C_2$-$C_6$) alkenyl, ($C_2$-$C_6$) alkynyl, aryl, heteroaryl, or heterocycloalkyl, wherein said aryl, heteroaryl, and heterocycloalkyl may be optionally and independently substituted by one or more of halogen, —OH, —($CH_2$)$_p$$NR_6R_7$, —CN, ($C_1$-$C_6$) alkyl, ($C_1$-$C_6$) haloalkyl, ($C_1$-$C_6$) hydroxyalkyl, ($C_2$-$C_6$) alkenyl, ($C_2$-$C_6$) alkynyl, or ($C_2$-$C_6$) hydroxyalkynyl;

$R_2$ and $R_3$ may be the same or different and are each independently H, ($C_1$-$C_6$) alkyl, or ($C_1$-$C_6$) haloalkyl;

$R_5$ is —$NR_6R_7$, ($C_1$-$C_6$) alkyl, ($C_1$-$C_6$) haloalkyl, ($C_1$-$C_6$) hydroxyalkyl, ($C_1$-$C_6$) aminoalkyl, ($C_1$-$C_6$) alkanoyl, ($C_3$-$C_7$) cycloalkyl, (C5-C7) cycloalkenyl, ($C_2$-$C_6$) alkenyl, and ($C_2$-$C_6$) alkynyl, aryl, heteroaryl, or heterocycloalkyl, wherein said aryl, heteroaryl, and heterocycloalkyl may be optionally and independently substituted by one or more of halogen, —OH, —CN, ($C_1$-$C_6$) alkyl, ($C_1$-$C_6$) haloalkyl, ($C_1$-$C_6$) hydroxyalkyl, ($C_2$-$C_6$) alkenyl, ($C_2$-$C_6$) alkynyl, or ($C_2$-$C_6$) hydroxyalkynyl;

Cy is a heteroaryl, which may be optionally and independently substituted by one or more of halogen, —OH, —($CH_2$)$_p$$NR_6R_7$; —CN, —CH═NOH, —C(O)$NR_6R_7$, —C(O)$OR_6$, ($C_1$-$C_6$) alkyl, ($C_1$-$C_6$) haloalkyl, ($C_1$-$C_6$) hydroxyalkyl, ($C_1$-$C_6$) alkanoyl, ($C_2$-$C_6$) alkenyl, ($C_2$-$C_6$) alkynyl, ($C_2$-$C_6$) hydroxyalkynyl, aryl, heteroaryl, or heterocycloalkyl, wherein said aryl, heteroaryl, and heterocycloalkyl may be optionally and independently substituted with one or more of —OH, halogen, —CN, —S(O)$_2$$NR_6R_7$, —$NR_6$S(O)$_2$$R_7$, —$NR_6R_7$, ($C_1$-$C_6$) alkyl, ($C_1$-$C_6$) haloalkyl, ($C_1$-$C_6$) hydroxyalkyl, or ($C_1$-$C_6$)alkoxy;

$R_6$, $R_7$ may be the same or different at each occurrence, and are at each occurrence independently —H, ($C_1$-$C_6$) alkyl, ($C_1$-$C_6$) haloalkyl, ($C_1$-$C_6$) hydroxyalkyl, ($C_1$-$C_6$) aminoalkyl, ($C_1$-$C_6$) alkanoyl, or aryl ($C_1$-$C_6$) alkanoyl or, when $R_6$ and $R_7$ are both linked to the same nitrogen atom, they may form, taken together with the nitrogen atom to which they are linked, a 4 to 6 membered heterocycle optionally containing one or more additional heteroatom or heteroatomic group selected from the group consisting of O, S, N, and NH;

Z, when present, is —O—, —NH—, —C(O)—, —NHC(O)—, —C(O)NH—, —S—, —S(O)—, or —S(O)$_2$—;

m is zero or 1;

n is 1 or 2;

p at each occurrence independently is zero or an integer ranging from 1 to 3;

or a pharmaceutically acceptable salt thereof.

2. A compound or pharmaceutically acceptable salt according to claim 1, which is in a form of a mixture of enantiomers or diastereoisomers.

3. A compound or pharmaceutically acceptable salt according to claim 1, wherein:
$R_2$ is H or ($C_1$-$C_6$) alkyl; and
$R_3$ is H.

4. A compound or pharmaceutically acceptable salt according to claim 1, wherein:
$R_2$ is H or ($C_1$-$C_6$) alkyl;
$R_3$ is H; and
Cy is 3H-purin-3-yl, 9H-purin-9-yl, 9H-purin-6-yl, 1H-pyrazolo[3,4-d]pyrimidin-1-yl, 6-oxo-5H-,6H,7H-pyrrolo[2,3-d]pyrimidin4-yl, pyrimidin-4-yl, pyrimidin-2-yl, pyrazin-2-yl, or 1,3,5-triazin-2-yl, each of which may be optionally and independently substituted by one or more of halogen, —OH, —($CH_2$)$_p$$NR_6R_7$; —CN, —CH═NOH, —C(O)$NR_6R_7$, —C(O)$OR_6$, ($C_1$-$C_6$) alkyl, ($C_1$-$C_6$) haloalkyl, ($C_1$-$C_6$) hydroxyalkyl, ($C_1$-$C_6$) alkanoyl, ($C_2$-$C_6$) alkenyl, ($C_2$-$C_6$) alkynyl, or ($C_2$-$C_6$) hydroxyalkynyl, or by a group selected from the group consisting of aryl, heteroaryl and heterocycloalkyl, which may be optionally and independently substituted with one or more of —OH, halogen, —CN, —S(O)$_2$$NR_6R_7$, —$NR_6$S(O)$_2$$R_7$, —$NR_6R_7$, ($C_1$-$C_6$) alkyl, ($C_1$-$C_6$) haloalkyl, ($C_1$-$C_6$) hydroxyalkyl, or ($C_1$-$C_6$)alkoxy.

5. A compound or pharmaceutically acceptable salt according to claim 4, wherein Cy is 1H-pyrazolo[3,4-d]pyrimidin-1-yl, optionally and independently substituted by one or more of halogen, —OH, —($CH_2$)$_p$$NR_6R_7$; —CN, —CH═NOH, —C(O)$NR_6R_7$, —C(O)$OR_6$, ($C_1$-$C_6$) alkyl, ($C_1$-$C_6$) haloalkyl, ($C_1$-$C_6$) hydroxyalkyl, ($C_1$-$C_6$) alkanoyl, ($C_2$-$C_6$) alkenyl, ($C_2$-$C_6$) alkynyl, or ($C_2$-$C_6$) hydroxyalkynyl, or by a group selected from the group consisting of aryl, heteroaryl and heterocycloalkyl, which may be optionally and independently substituted with one or more of —OH, halogen, —CN, —S(O)$_2$$NR_6R_7$, —$NR_6$S(O)$_2$$R_7$, —$NR_6R_7$, ($C_1$-$C_6$) alkyl, ($C_1$-$C_6$) haloalkyl, ($C_1$-$C_6$) hydroxyalkyl, or ($C_1$-$C_6$)alkoxy; and
m is zero.

6. A compound or pharmaceutically acceptable salt according to claim 5, wherein
$R_1$ and $R_4$ may be the same or different and are each independently H, cyclopentyl, or phenyl;
$R_2$ is H or methyl;
$R_3$ is H;
$R_5$ is methyl, isopropyl, tert-butyl, cyclopropyl, phenyl, pyridinyl, or morpholinyl;
Cy is 1H-pyrazolo[3,4-d]pyrimidin-1-yl, which may be optionally and independently substituted by one or more of iodine, —$NH_2$, phenyl, pyridinyl, wherein said phenyl and pyridinyl nay be optionally and independently substituted with one or more of —OH or fluorine;
$R_6$ and $R_7$ are —H
m is zero;
n is 1; and
p is at each occurrence independently 0 or 1 or 2.

7. A compound or pharmaceutically acceptable salt according to claim 4, wherein Cy is (I-6) is pyrimidin-4-yl, optionally substituted by one or more of halogen, —OH, —($CH_2$)$_p$$NR_6R_7$; —CN, —CH═NOH, —C(O)$NR_6R_7$, —C(O)$OR_6$, ($C_1$-$C_6$) alkyl, ($C_1$-$C_6$) haloalkyl, ($C_1$-$C_6$) hydroxyalkyl, ($C_1$-$C_6$) alkanoyl, ($C_2$-$C_6$) alkenyl, ($C_2$-$C_6$) alkynyl, or ($C_2$-$C_6$) hydroxyalkynyl, or by a group selected from the group consisting of aryl, heteroaryl, and heterocycloalkyl, which can be optionally and independently substituted with one or more of —OH, halogen, —CN, —S(O)$_2$$NR_6R_7$, —$NR_6$S(O)$_2$$R_7$, —$NR_6R_7$, ($C_1$-$C_6$) alkyl, ($C_1$-$C_6$) haloalkyl, ($C_1$-$C_6$) hydroxyalkyl, or ($C_1$-$C_6$)alkoxy; and
m is 1.

8. A compound or pharmaceutically acceptable salt according to claim 7, wherein
$R_1$ is phenyl and $R_4$ is H;
$R_2$ is methyl;
$R_3$ is H;
$R_5$ is methyl, isopropyl, cyclopropyl, or phenyl;
Cy is (I-6) is pyrimidin-4-yl substituted —$NH_2$ or —CN;
m is 1;
$R_6$ and $R_7$ are —H;
Z is —NH—;
n is 1; and
p is at each occurrence independently zero or 1.

9. A compound or pharmaceutically acceptable salt according to claim 1, which is a compound selected from the group consisting of:

- 5-{1-[4-amino-3-(3-fluoro-5-hydroxyphenyl)-1H-pyrazolo[3,4-d]pyrimidin-1-yl]ethyl}-2-benzyl-6-phenyl-2,3-dihydropyridazin-3-one;
- 5-{1-[4-amino-3-(3-fluoro-5-hydroxyphenyl)-1H-pyrazolo[3,4-d]pyrimidin-1-yl]ethyl}-2-methyl-6-phenyl-2,3-dihydropyridazin-3-one;
- 5-{1-[4-amino-3-(3-fluoro-5-hydroxyphenyl)-1H-pyrazolo[3,4-d]pyrimidin-1-yl]ethyl}-6-phenyl-2-(propan-2-yl)-2,3-dihydropyridazin-3-one;
- 5-{1-[4-amino-3-(3-fluoro-5-hydroxyphenyl)-1H-pyrazolo[3,4-d]pyrimidin-1-yl]ethyl}-2-(cyclopropylmethyl)-6-phenyl-2,3-dihydropyridazin-3-one;
- 5-{1-[4-amino-3-(3-fluoro-5-hydroxyphenyl)-1H-pyrazolo[3,4-d]pyrimidin-1-yl]ethyl}-2,6-diphenyl-2,3-dihydropyridazin-3-one;
- 5-{1-[4-amino-3-(3-fluoro-5-hydroxyphenyl)-1H-pyrazolo[3,4-d]pyrimidin-1-yl]ethyl}-6-phenyl-2-(pyridin-2-ylmethyl)-2,3-dihydropyridazin-3-one;
- 5-{1-[4-amino-3-(3-fluoro-5-hydroxyphenyl)-1H-pyrazolo[3,4-d]pyrimidin-1-yl]ethyl}-2-benzyl-2,3-dihydropyridazin-3-one;
- 5-{1-[4-amino-3-(3-fluoro-5-hydroxyphenyl)-1H-pyrazolo[3,4-d]pyrimidin-1-yl]ethyl}-2-phenyl-2,3-dihydropyridazin-3-one;
- 5-{1-[4-amino-3-(3-fluoro-5-hydroxyphenyl)-1H-pyrazolo[3,4-d]pyrimidin-1-yl]ethyl}-2-methyl-2,3-dihydropyridazin-3-one;
- 5-{1-[4-amino-3-(3-fluoro-5-hydroxyphenyl)-1H-pyrazolo[3,4-d]pyrimidin-1-yl]ethyl}-2-tert-butyl-4-phenyl-2,3-dihydropyridazin-3-one;
- 5-{1-[4-amino-3-(3-fluoro-5-hydroxyphenyl)-1H-pyrazolo[3,4-d]pyrimidin-1-yl]ethyl}-2-benzyl-4-phenyl-2,3-dihydropyridazin-3-one;
- 5-{1-[4-amino-3-(3-fluoro-5-hydroxyphenyl)-1H-pyrazolo[3,4-d]pyrimidin-1-yl]ethyl}-2-methyl-4-phenyl-2,3-dihydropyridazin-3-one;
- 5-{1-[4-amino-3-(3-fluoro-5-hydroxyphenyl)-1H-pyrazolo[3,4-d]pyrimidin-1-yl]ethyl}-2,4-diphenyl-2,3-dihydropyridazin-3-one;
- 5-{1-[4-amino-3-(3-fluoro-5-hydroxyphenyl)-1H-pyrazolo[3,4-d]pyrimidin-1-yl]ethyl}-2-[2-(morpholin-4-yl)ethyl]-4-phenyl-2,3-dihydropyridazin-3-one;
- 5-{1-[4-amino-3-(3-fluoro-5-hydroxyphenyl)-1H-pyrazolo[3,4-d]pyrimidin-1-yl]ethyl}-4-phenyl-2-(pyridin-3-yl)-2,3-dihydropyridazin-3-one;
- 5-{1-[4-amino-3-(3-fluoro-5-hydroxyphenyl)-1H-pyrazolo[3,4-d]pyrimidin-1-yl]ethyl}-2-benzyl-4-cyclopentyl-2,3-dihydropyridazin-3-one;
- 5-{1-[4-amino-3-(5-hydroxypyridin-3-yl)-1H-pyrazolo[3,4-d]pyrimidin-1-yl]ethyl}-2-benzyl-4-cyclopentyl-2,3-dihydropyridazin-3-one;
- 5-{[4-amino-3-(3-fluoro-5-hydroxyphenyl)-1H-pyrazolo[3,4-d]pyrimidin-1-yl]methyl}-2-benzyl-2,3-dihydropyridazin-3-one;
- 4-amino-6-{[1-(1-benzyl-6-oxo-3-phenyl-1,6-dihydropyridazin-4-yl)ethyl]amino}pyrimidine-5-carbonitrile;
- 4-amino-6-(1-(1-methyl-6-oxo-3-phenyl-1,6-dihydropyridazin-4-yl)ethylamino)pyrimidine-5-carbonitrile;
- 4-amino-6-({1-[6-oxo-3-phenyl-1-(propan-2-yl)-1,6-dihydropyridazin-4-yl]ethyl}amino)pyrimidine-5-carbonitrile;
- 4-amino-6-({1-[1-(cyclopropylmethyl)-6-oxo-3-phenyl-1,6-dihydropyridazin-4-yl]ethyl}amino)pyrimidine-5-carbonitrile;
- 4-amino-6-{[1-(6-oxo-1,3-diphenyl-1,6-dihydropyridazin-4-yl)ethyl]amino}pyrimidine-5-carbonitrile; and
- 2-benzyl-6-phenyl-5-{1-[(9H-purin-6-yl)amino]ethyl}-2,3-dihydropyridazin-3-one, or a pharmaceutically acceptable salt of said compound.

10. A pharmaceutical composition, comprising a compound or pharmaceutically acceptable salt according to claim 1 and one or more pharmaceutically acceptable carriers or excipients.

11. A pharmaceutical composition according to claim 10, further comprising one or more additional active ingredients.

* * * * *